(12) United States Patent
Luo et al.

(10) Patent No.: US 11,319,305 B2
(45) Date of Patent: May 3, 2022

(54) PYRIMIDINE SULFAMIDE DERIVATIVE AND PREPARATION METHOD AND MEDICAL APPLICATION THEREOF

(71) Applicant: SHIJIAZHUANG SAGACITY NEW DRUG DEVELOPMENT CO., LTD., Hebei (CN)

(72) Inventors: Yunfu Luo, Shanghai (CN); Maoyi Lei, Shanghai (CN); Junmiao Li, Shanghai (CN); Yu Xu, Shanghai (CN); Ran Wei, Shanghai (CN); Shuhui Chen, Shanghai (CN)

(73) Assignee: Shijiazhuang Sagacity New Drug Development Co., Ltd., Hebei (CN)

( * ) Notice: Subject to any disclaimer, the term of this patent is extended or adjusted under 35 U.S.C. 154(b) by 0 days.

(21) Appl. No.: 16/764,654

(22) PCT Filed: Nov. 19, 2018

(86) PCT No.: PCT/CN2018/116196
§ 371 (c)(1),
(2) Date: May 15, 2020

(87) PCT Pub. No.: WO2019/101039
PCT Pub. Date: May 31, 2019

(65) Prior Publication Data
US 2020/0283425 A1     Sep. 10, 2020

(30) Foreign Application Priority Data
Nov. 21, 2017 (CN) .......................... 201711168111.3

(51) Int. Cl.
*C07D 407/14* (2006.01)
*C07D 417/14* (2006.01)
*C07D 471/04* (2006.01)

(52) U.S. Cl.
CPC ......... *C07D 407/14* (2013.01); *C07D 417/14* (2013.01); *C07D 471/04* (2013.01)

(58) Field of Classification Search
CPC combination set(s) only.
See application file for complete search history.

(56) References Cited

U.S. PATENT DOCUMENTS

| 2004/0077670 A1 | 4/2004 | Bolli et al. |
| 2007/0167472 A1 | 7/2007 | Bolli et al. |
| 2008/0004298 A1 | 1/2008 | Bolli et al. |

FOREIGN PATENT DOCUMENTS

| CN | 1524079 A | 8/2004 |
| CN | 1711248 A | 12/2005 |
| CN | 101056872 A | 10/2007 |
| EP | 1072597 A1 | 1/2001 |
| EP | 1160248 | 12/2001 |
| WO | WO-2002053557 A1 | 7/2002 |

OTHER PUBLICATIONS

Extended European search report issued in European Patent Application No. 18881280.4, dated Mar. 24, 2021.
Oct. 25, 2021 First Office Action issued in Indian Patent Application No. 202027022016.
Nov. 29, 2021 First Office Action issued in Russian Patent Application No. 2020119900.
Feb. 20, 2019 International Search Report issued in International Patent Application No. PCT/CN2018/116196.
Feb. 20, 2019 Written Opinion of the International Searching Authority issued in International Patent Application No. PCT/CN2018/116196.
Sidharta, P.N. et al., "Macitentan: Entry-into-Humans Study with a New Endothelin Receptor Antagonist", Eur J Clin Pharmacol, vol. 67, May 4, 2011, pp. 977-984.
Bolli, M.H. et al., "The Discovery of N-[5-(4-Bromophenyl)-6-[2-[(5-bromo-2-pyrimidinyl)oxy]ethoxyl]-4-pyrimidinyl]-N'-propylsulfamide(Macitentan), an Orally Active. Potent Dual Endothelin Receptor Antagonist", Journal of Medicinal Chemistry, vol. 55, Aug. 3, 2012, pp. 7849-7861.
Sidharta, P.N. et al., "Clinical Pharmacokinetics and Pharmacodynamics of the Endothelin Receptor Antagonist Macitentan", Clin Pharmacokinet, vol. 54, Apr. 10, 2015, pp. 457-471.

*Primary Examiner* — Heidi Reese

(57) ABSTRACT

Disclosed are a series of pyrimidine sulfamide compounds and applications thereof in preparing a drug for a disease related to an $ET_A$ receptor antagonist. In particular, disclosed is a derived compound represented by formula (I) or a tautomer or pharmaceutically acceptable composition thereof.

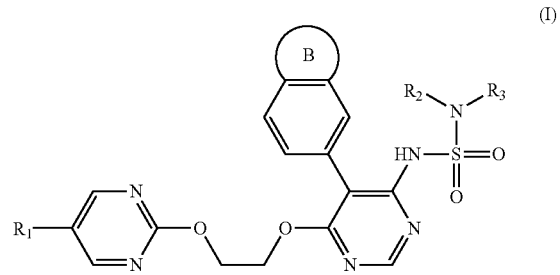

19 Claims, No Drawings

PYRIMIDINE SULFAMIDE DERIVATIVE AND PREPARATION METHOD AND MEDICAL APPLICATION THEREOF

CROSS-REFERENCE TO RELATED APPLICATIONS

This application is a 371 National Phase of International Application No. PCT/CN2018/116196, filed Nov. 19, 2018, which claims the benefit of Chinese Patent Application No. CN 201711168111.3, filed Nov. 21, 2017. The entire disclosures of the above applications are incorporated herein by reference.

FIELD OF THE INVENTION

The present disclosure relates to a class of pyrimidine sulfamide derived compounds and the use thereof in the manufacture of a medicament for an $ET_A$ receptor antagonist related disease. Specifically, disclosed is a derived compound of formula (I), a tautomer thereof, or a pharmaceutically acceptable composition thereof.

PRIOR ARTS

Endothelin (ET) is a family of isomeric peptide containing 21-amino acid, all of which have a hydrophobic C-terminal consisting of 6 identical amino acid residues and 2 intrachain disulfide bonds. There are three isoforms of endothelin encoded by different genes in human body, namely ET-1, ET-2 and ET-3. Among them, ET-1 has the strongest vasoconstrictor activity, with veins being 3 to 10 times higher than arteries, which is the major isoform causing disease. ET-1 is the most abundant type of endothelin family and it also has the most important function. It is mainly expressed in vascular endothelium, and is also distributed in non-vascular tissues such as heart, kidney, lung, adrenal gland and other organs.

ET does not only function as a vascular factor that modulates blood pressure, but also as a hormone that induces many cell progressions (such as proliferation, apoptosis and migration) which lead to tissue hypertrophy, remodeling, fibrosis and inflammation. ET-1 levels in plasma and tissue will increase in various diseases such as pulmonary arterial hypertension, hypertension, sepsis, atherosclerosis, acute myocardial infarction, congestive heart failure, migraine, asthma, and the like. Therefore, endothelin receptor antagonists are widely investigated as very potential therapeutic agents.

Endothelin receptors belong to G protein coupled receptors, which mainly have three types: $ET_A$, $ET_B$ and $ET_C$. They have different distributions in different tissues and organs, have different affinities for three endothelin subtypes, and have a large difference in physiological effects. Endothelin $ET_A$ receptors are mainly distributed on smooth muscle cells, and selectively bind to ET-1 and mediate the contraction of vascular smooth muscle. Endothelin $ET_B$ receptors are divided into two subtypes, namely $ET_{B1}$ and $ET_{B2}$, wherein the former is distributed in endothelial cells and mediates the release of endothelium-derived relaxing factor (EDRF), prostacyclin (PGI2) and nitric oxide (NO), thereby causing vasodilation, while the latter is located on vascular smooth muscle, the effect is the same as that of the $ET_A$ receptor to directly mediate the contraction of the venous blood vessel, and the affinity of the endothelin $ET_B$ receptor for ET-1, ET-2 and ET-3 is similar. $ET_C$ receptor is an ET-3 selective receptor, mainly distributed in neuronal cells, and functions as a neurotransmitter. ET-1 acts mainly through $ET_A$ and $ET_B$ receptors. The endothelin receptor antagonist can be divided into $ET_A$ receptor antagonist, $ET_B$ receptor antagonist, and $ET_A/ET_B$ dual antagonist, of which the pre-clinical and/or clinical effects in a variety of diseases such as subarachnoid hemorrhage, heart failure, pulmonary artery hypertension, primary hypertension, refractory hypertension, neurogenic inflammation, diabetic nephropathy, focal segmental glomerulosclerosis, renal failure, neurogenic inflammation, cerebral vasospasm after renal failure and myocardial infarction and the like have been proved. Highly selective $ET_A$ receptor antagonists inhibit the strong vasoconstrictor effect of ET-1, while avoiding some adverse response of non-selective $ET_A/ET_B$ receptor dual antagonists, thereby reducing clinical side effects.

Patent WO200205355 discloses a compound macitentan, which can be used for treating diseases associated with the action of endothelin.

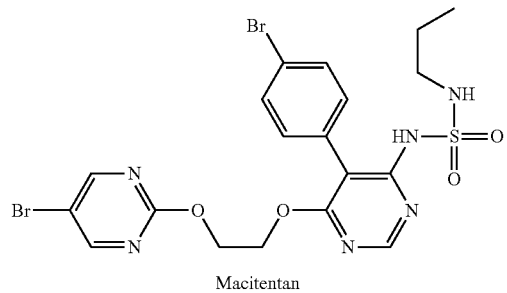 [SMILES: CCCNS(=O)(=O)Nc1ncnc(OCCOc2ncc(Br)cn2)c1-c1ccc(Br)cc1]

Macitentan

CONTENT OF THE PRESENT INVENTION

The present disclosure provides a compound of formula (I), an isomer thereof or a pharmaceutically acceptable salt thereof,

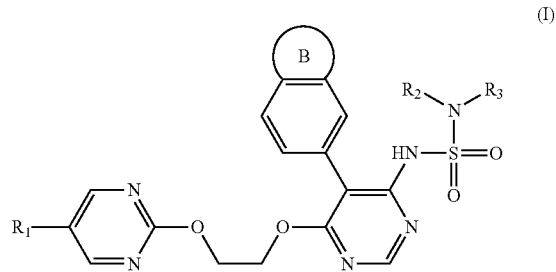

(I)

wherein, $R_1$ is selected from H, F, Cl, Br, I, OH and $NH_2$;

$R_2$ is selected from H and $C_{1-3}$ alkyl, wherein the $C_{1-3}$ alkyl is optionally substituted by one, two or three R;

$R_3$ is selected from H, $C_{1-6}$ alkyl, $C_{1-6}$ heteroalkyl, —$C_{1-3}$ alkyl-$C_{3-6}$ cycloalkyl, $C_{3-6}$ cycloalkyl and —$C_{1-3}$ alkyl-3-7 member heterocycloalkyl, wherein the $C_{1-6}$ alkyl, $C_{1-6}$ heteroalkyl, —$C_{1-3}$ alkyl-$C_{3-6}$ cycloalkyl, $C_{3-6}$ cycloalkyl or —$C_{1-3}$ alkyl-3-7-membered heterocycloalkyl is optionally substituted by one, two or three R;

or, $R_2$ and $R_3$ are connected to form a 3-8 membered ring optionally substituted by one, two or three R;

ring B is selected from 3-7 membered heterocycloalkyl and 5-6 membered heteroaryl, the 3-7 membered heterocycloalkyl or 5-6 membered heteroaryl is optionally substituted by one, two or three R;

R is independently selected from H, F, Cl, Br, I, OH, NH$_2$, CN, C$_{1-6}$ alkyl and C$_{1-6}$ heteroalkyl, wherein the C$_{1-6}$ alkyl or C$_{1-6}$ heteroalkyl is optionally substituted by one, two or three R;

R' is independently selected from F, Cl, Br, I, OH, NH$_2$, CN, Me, CH$_2$F, CHF$_2$, CF$_3$ and Et;

each of the C$_{1-6}$ heteroalkyl, 3-7 membered heterocycloalkyl and 5-6 membered heteroaryl contains one, two, three or four heteroatoms or heteroatom groups independently selected from N, —O—, —S—, —NH—, —S(=O)$_2$— and —S(=O)—.

In some embodiments of the present disclosure, R is selected from H, F, Cl, Br, I, OH, NH$_2$, CN, C$_{1-3}$ alkyl, C$_{1-3}$ alkyl-S(=O)$_2$— and C$_{1-3}$ alkyl-O—, wherein the C$_{1-3}$ alkyl, C$_{1-3}$ alkyl-S(=O)$_2$— or C$_{1-3}$ alkyl-O— is optionally substituted by one, two or three R', and other variables are as defined in the present disclosure.

In some embodiments of the present disclosure, R is selected from H, F, Cl, Br, I, OH, NH$_2$, CN, Me, Et,

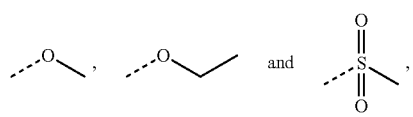

wherein the Me, Et,

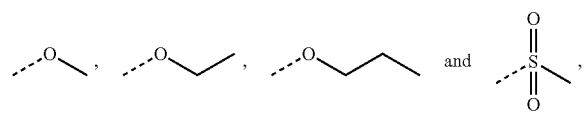

is optionally substituted by one, two or three R', and other variables are as defined in the present disclosure.

In some embodiments of the present disclosure, R is selected from H, F, Cl, Br, I, OH, NH$_2$, CN, Me, CH$_2$F, CHF$_2$, CF$_3$, Et,

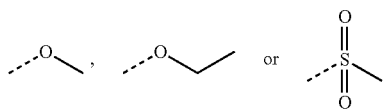

and other variables are as defined in the present disclosure.

In some embodiments of the present disclosure, R$_2$ is selected from H and Me, and other variables are as defined in the present disclosure.

In some embodiments of the present disclosure, R$_3$ is selected from H, C$_{1-4}$ alkyl, C$_{1-4}$ alkyl-O—C$_{1-4}$ alkyl, cyclobutyl, —C$_{1-3}$ alkyl-cyclobutyl, —C$_{1-3}$ alkyl-cyclopropyl, —C$_{1-3}$ alkyl-tetrahydrofuranyl and —C$_{1-3}$ alkyl-tetrahydropyranyl, wherein the C$_{1-4}$ alkyl, C$_{1-4}$ alkyl-O—C$_{1-4}$ alkyl, cyclobutyl, —C$_{1-3}$ alkyl-cyclobutyl, —C$_{1-3}$ alkyl-cyclopropyl, —C$_{1-3}$ alkyl-tetrahydrofuranyl or —C$_{1-3}$ alkyl-tetrahydropyranyl is optionally substituted by one, two or three R, and other variables are as defined in the present disclosure.

In some embodiments of the present disclosure, R$_3$ is selected from H, Me, Et,

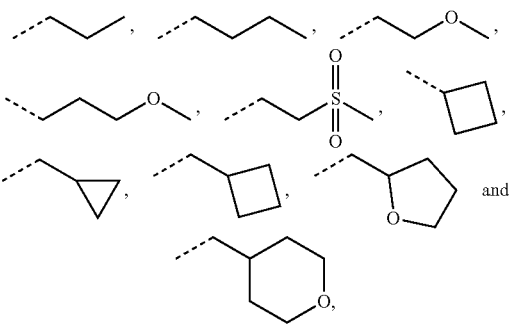

wherein the Me, Et,

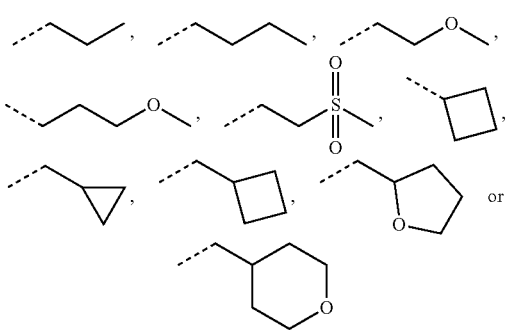

is optionally substituted by one, two or three R, and other variables are as defined in the present disclosure.

In some embodiments of the present disclosure, R$_3$ is selected from H, Me, Et,

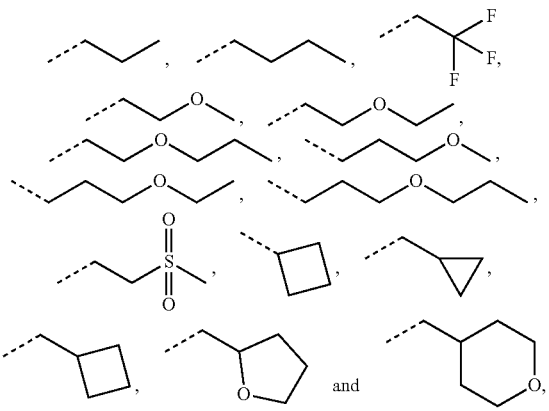

and other variables are as defined in the present disclosure.

In some embodiments of the present disclosure, R$_2$ and R$_3$ are connected to form a 6-8 membered heterocycloalkyl optionally substituted by one, two or three R.

In some embodiments of the present disclosure, the structural unit

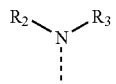

is selected from

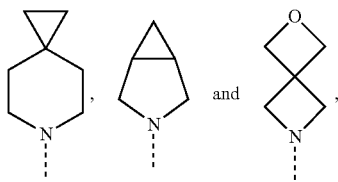

wherein the

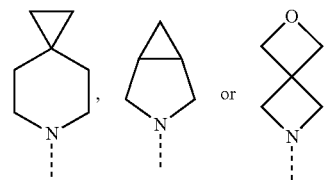

is optionally substituted by one, two or three R, and other variables are as defined in the present disclosure.

In some embodiments of the present disclosure, the structural unit

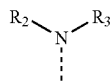

is selected from

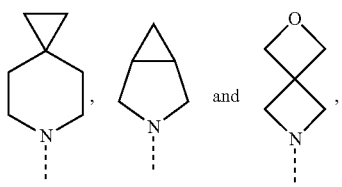

and other variables are as defined in the present disclosure.

In some embodiments of the present disclosure, ring B is selected from tetrahydrofuranyl, tetrahydrothienyl, 1,3-dioxolanyl, pyrrolidinyl, thiazolyl, pyrazolyl and imidazolyl, wherein the tetrahydrofuranyl, tetrahydrothienyl, 1,3-dioxolanyl, pyrrolidinyl, thiazolyl, pyrazolyl or imidazolyl is optionally substituted by one, two or three R, and other variables are as defined in the present disclosure.

In some embodiments of the present disclosure, the structural unit

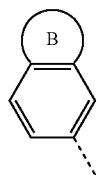

is selected from

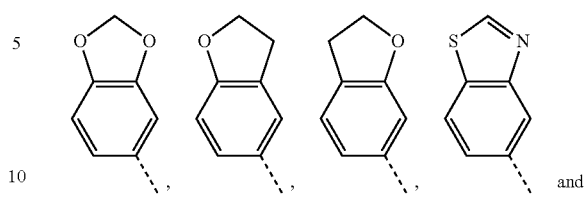

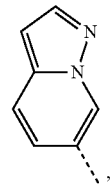

and other variables are as defined in the present disclosure.

Other embodiments of the present disclosure can be obtained by the arbitrary combination of variables.

In some embodiments of the present disclosure, the compound, the isomer thereof or the pharmaceutically acceptable salt thereof is selected from

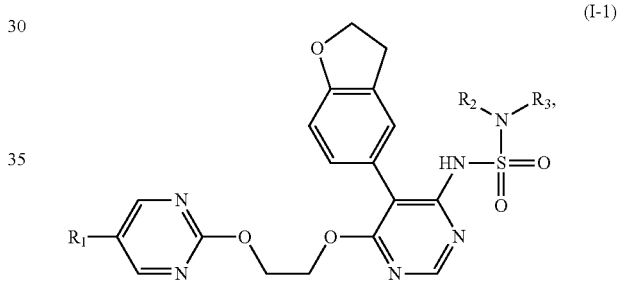

(I-1)

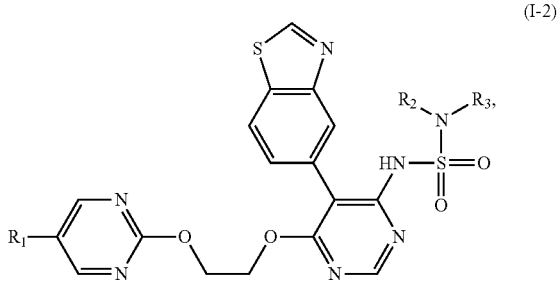

(I-2)

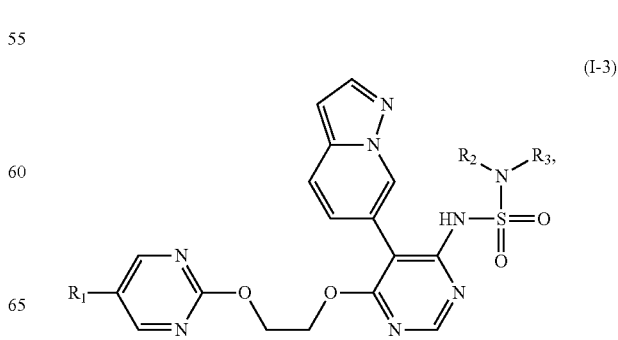

(I-3)

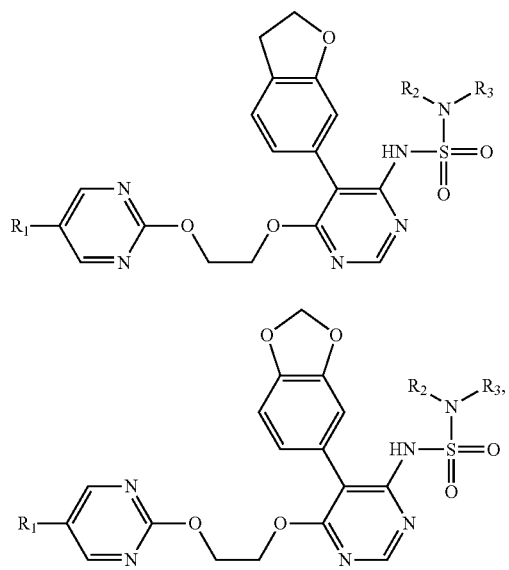
(I-4)
(I-5)
wherein,
R, R₁ or R₂ is as defined in the present disclosure.
The present disclosure also provides a compound, an isomer thereof or a pharmaceutically acceptable salt thereof, which is selected from
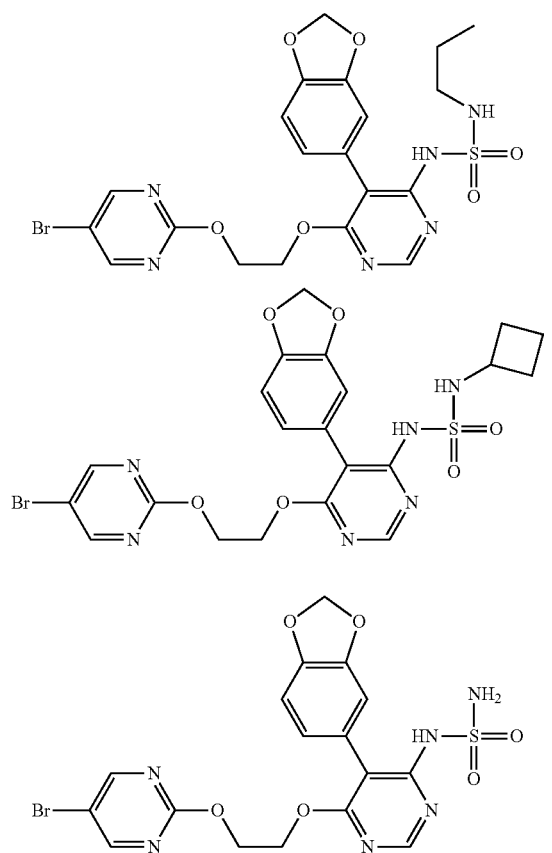
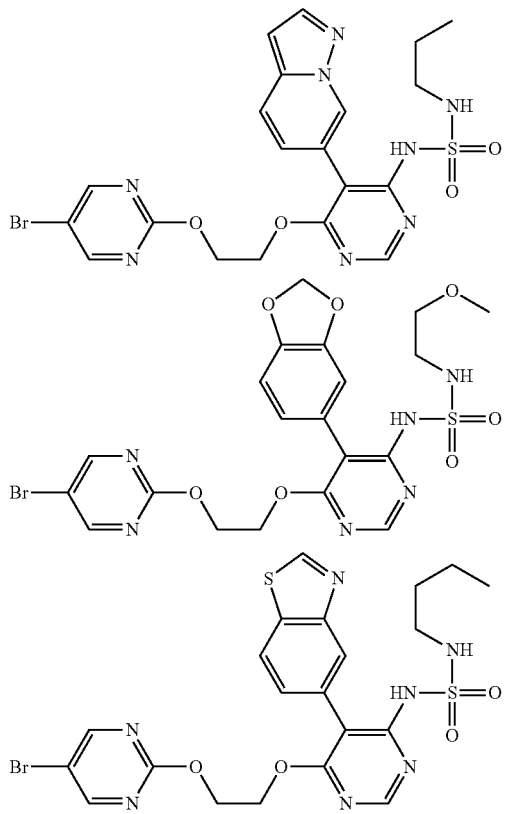
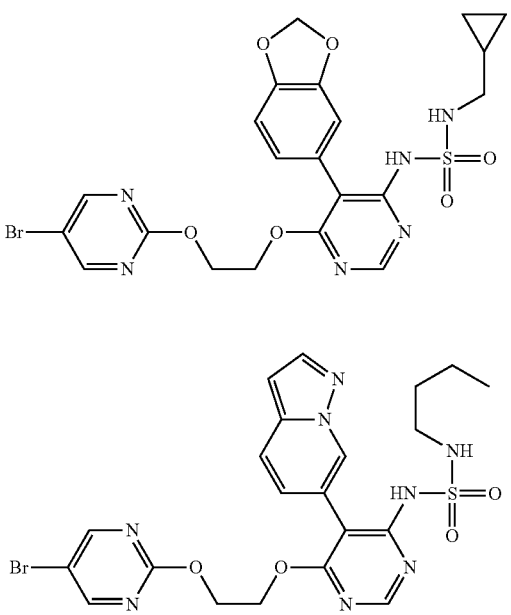

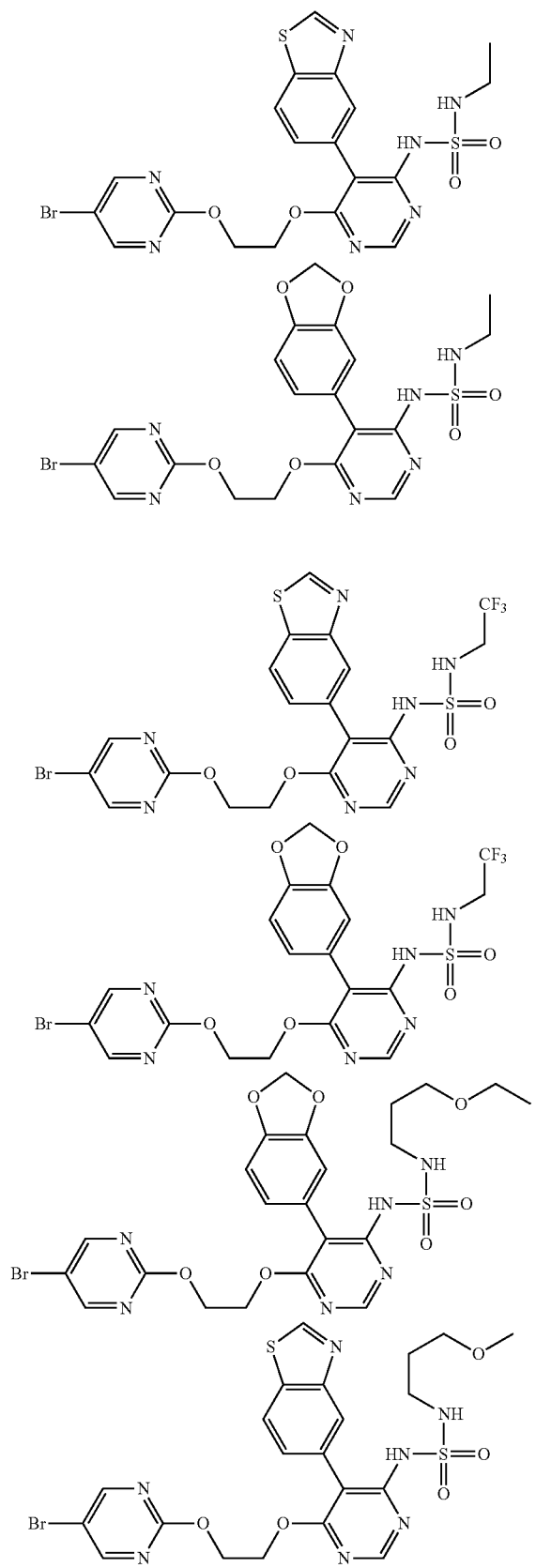
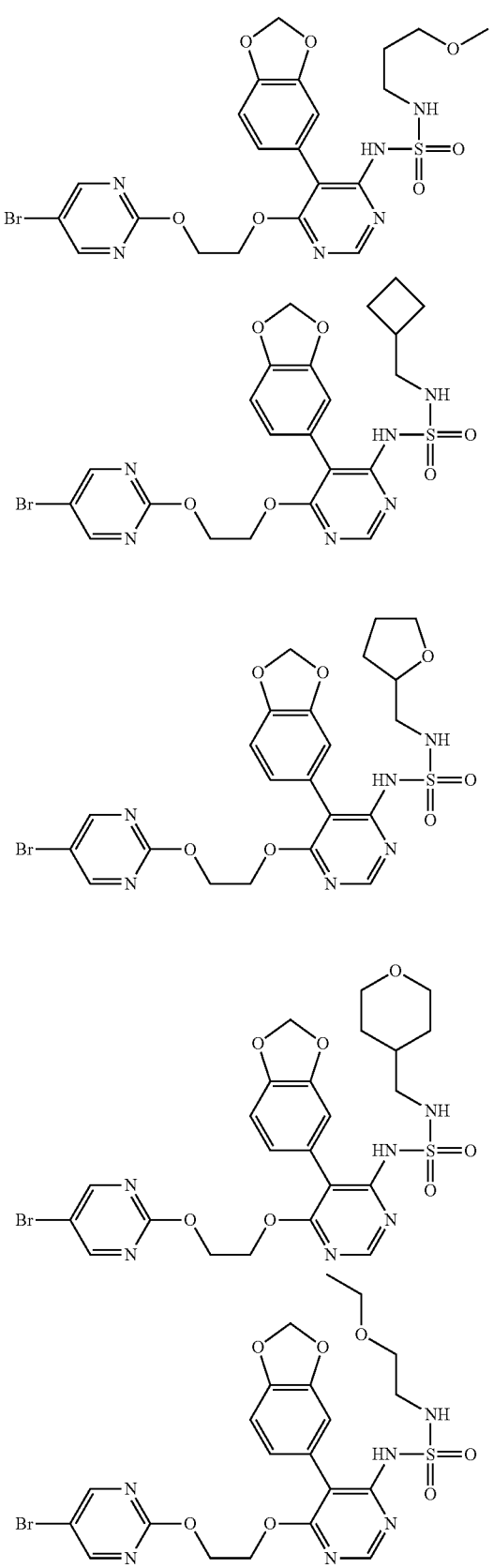

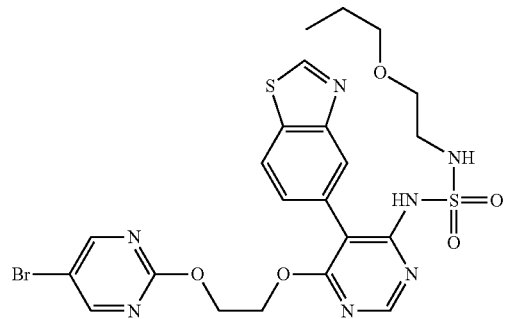
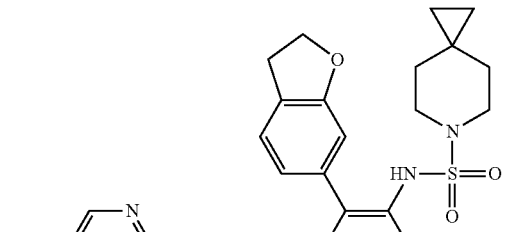
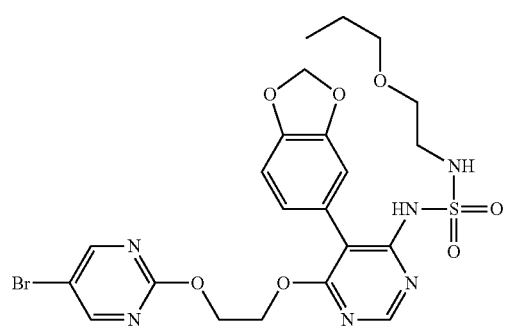
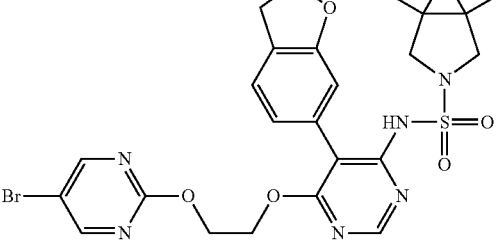
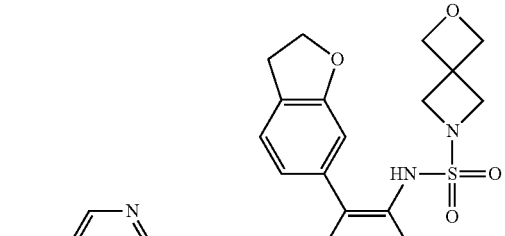
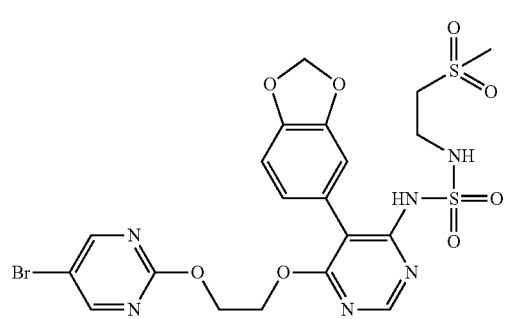
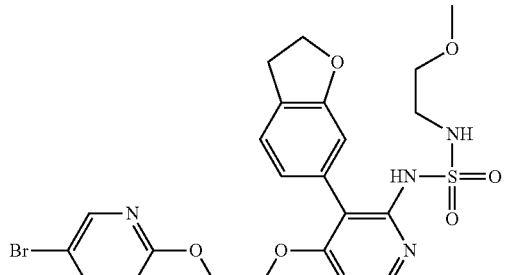
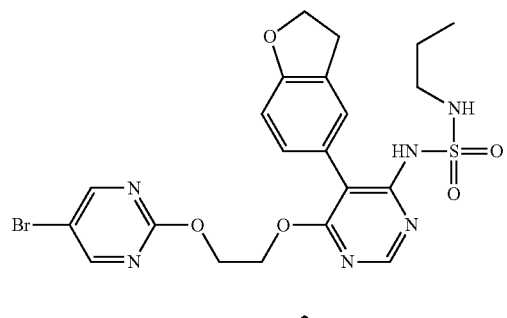
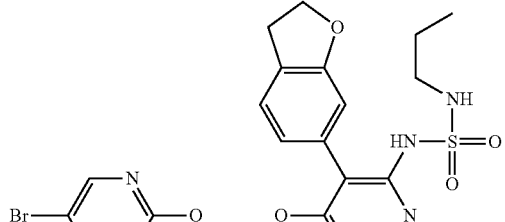
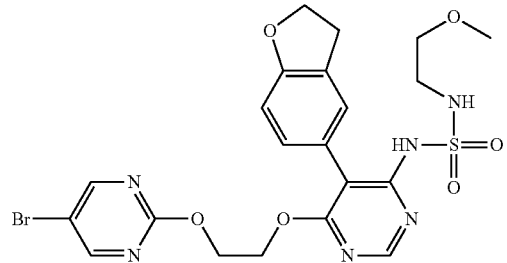
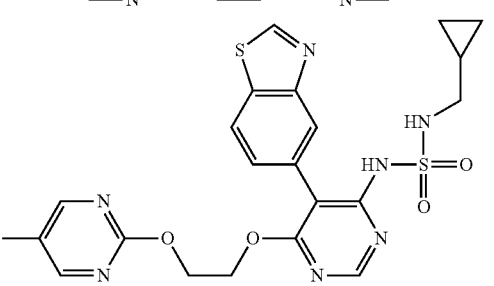 and

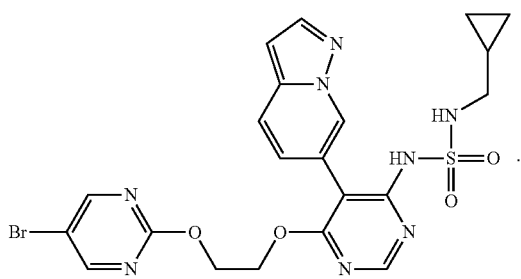 [SMILES: O=S(=O)(NCC1CC1)Nc1ncnc(OCCOc2ncc(Br)cn2)c1-c1ccc2ccnn2c1]

In some embodiments of the present disclosure, the compound, the isomer thereof or the pharmaceutically acceptable salt thereof is selected from

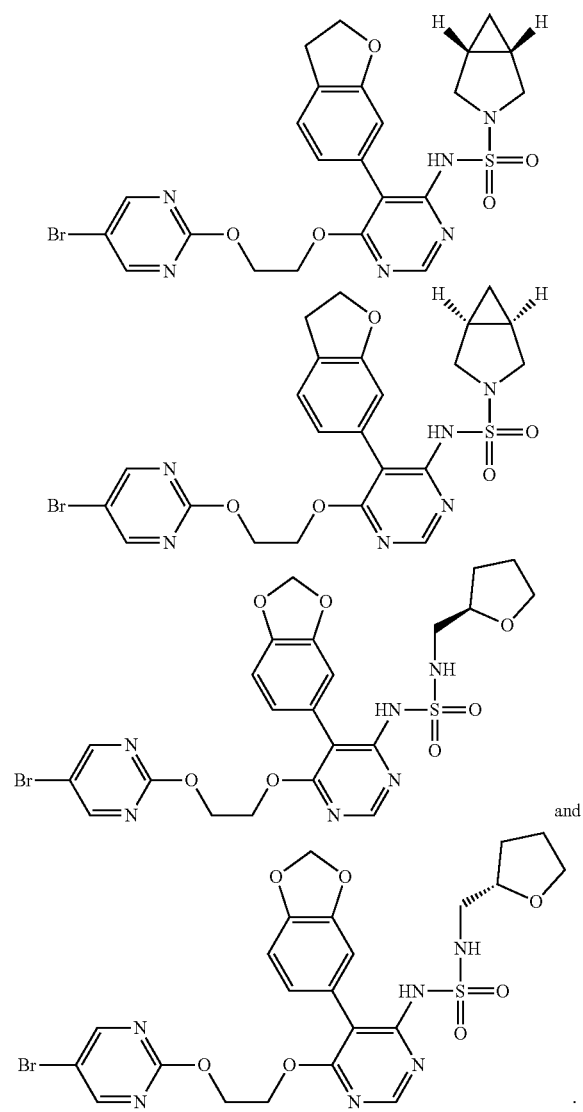

The disclosure also provides a pharmaceutical composition, which comprises a therapeutically effective amount of the compound or the pharmaceutically acceptable salt thereof as an active ingredient, and a pharmaceutically acceptable carrier.

The present disclosure also provides a use of the compound or the pharmaceutically acceptable salts thereof or the compositions in the manufacture of an $ET_A$ receptor antagonist related medicament.

In some embodiments of the present disclosure, the $ET_A$ receptor antagonist related medicament is a medicament for the indications such as pulmonary artery hypertension, primary hypertension, refractory hypertension, diabetic nephropathy and intracranial vasospasm.

DEFINITION AND DESCRIPTION

Unless otherwise indicated, the following terms when used in the descriptions and the claims of the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compound of the present disclosure may have a specific geometric or stereoisomeric form. The present disclosure contemplates all such compounds, including cis and trans isomer, (−)- and (+)-enantiomer, (R)- and (S)-enantiomer, diastereoisomer, (D)-isomer, (L)-isomer, and racemic mixture and other mixtures, for example, an enantiomer or diastereoisomer enriched mixture, all of which are encompassed within the scope of the present disclosure. The substituent such as alkyl may have an additional asymmetric carbon atom. All these isomers and mixtures thereof are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(D)" or "(+)" stands for dextrorotation, "(L)" or "(−)" stands for levorotation, "(DL)" or "(±)" stands for racemization.

Unless otherwise specified, the absolute configuration of a stereogenic center is represented by a wedged solid bond ( ▰ ) and a wedged dashed bond ( ▰ ) and the relative configuration of a stereogenic center is represented by a straight solid bond ( ▰ ) and a straight dashed bond ( ▰ ). A wave line ( ▰ ) represents a wedged solid bond ( ▰ ) or a wedged dashed bond ( ▰ ) or represents a straight solid bond ( ▰ ) or a straight dashed bond ( ▰ ).

The compounds of the disclosure may be present in particular. Unless otherwise indicated, the terms "tautomer" or "tautomeric form" refer to the fact that the different functional isomers are in dynamic equilibrium at room temperature and can be rapidly converted into each other. If tautomers are possible (as in solution), the chemical equilibrium of the isomers can be achieved. For example, proton tautomers (also known as prototropic tautomers) include interconversions by proton transfer, such as keto-enol isomerization and imine-enamine isomerization. The valence tautomer includes the mutual transformation of some bonding electrons. A specific example of keto-enol tautomerization is the interconversion between two tautomers of pentane-2,4-dione and 4-hydroxypent-3-en-2-one.

Unless otherwise specified, the terms "enriched in one isomer", "isomer enriched", "enriched in one enantiomer" or "enantiomer enriched" refer to the content of one of the isomers or enantiomers is less than 100%, and the content of the isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the terms "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (9-isomer, or D and L isomer can be prepared using chiral synthesis or chiral reagents or other conventional techniques. If one kind of enantiomer of certain compound of the present disclosure is to be obtained. The pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl). The compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^3H$), iodine-125 ($^{125}I$) or C-14 ($^{14}C$). For another example, hydrogen can be replaced by heavy hydrogen to form a deuterated drug, and the bond composed of barium and carbon is stronger than the bond composed of common hydrogen and carbon. Compared with undeuterated drugs, deuterated drugs have reduced side effects and increased drug stability, enhanced the efficacy and prolonged the biological half-life of the drug. All isotopic variations of the compound of the present disclosure, whether radioactive or not, are encompassed within the scope of the present disclosure.

"Optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variants, as long as the valence of the specific atom is normal and the substituted compound is stable. When the substituent is an oxygen (i.e. =O), it means two hydrogen atoms are substituted. Positions on an aromatic ring cannot be substituted with a ketone. The term "optionally substituted" means an atom can be substituted with a substituent or not, unless otherwise specified. The type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When the listed substituents are not indicated by which atom is attached to the substituted group, such a substituent may be bonded through any of its atoms, for example, the pyridyl group as a substituent may be bonded to the substituted group through any one of the carbon atoms on the pyridine ring. When the enumerative linking group does not indicate the direction for linking, the direction for linking is arbitrary, for example, the linking group L contained in

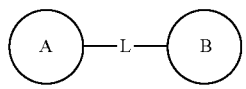

is -MW—, then -MW— can link ring A and ring B to form

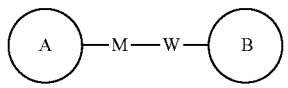

in the direction same as left-to-right reading order, and form

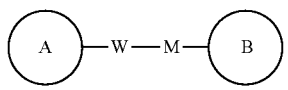

in the direction contrary to left-to-right reading order. Combinations of the linking groups, substituents and/or variants thereof are permissible only if such combinations result in stable compounds.

Unless otherwise specified, the term "hetero" represents a heteroatom or a heteroatomic group (e.g., an atomic group containing a heteroatom), including the atom except carbon (C) and hydrogen (H) and the atomic group containing heteroatom, for example, including oxygen (O), nitrogen (N), sulfur (S), silicon (Si), germanium (Ge), aluminum (Al), boron (B), —O—, —S—, =O, =S, —C(=O)O—, —C(=O)—, —C(=S)—, —S(=O), —S(=O)$_2$—, and the group consisting of —C(=O)N(H)—, —N(H)—, —C(=NH)—, —S(=O)$_2$N(H)— and —S(=O)N(H)—, each of which is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so called ring includes a single ring, a double ring, a spiral ring, a fused ring or a bridged ring. The number of the atom on the ring is usually defined as the member number of the ring, for example, a "5-7 membered ring" means that 5 to 7 atoms are arranged on a ring. Unless otherwise specified, the ring optionally contains 1 to 3 heteroatoms. Therefore, a "5-7 membered ring" includes, for example, phenyl, pyridinyl and piperidinyl; on the other hand. The term "5-7 membered heterocloalkyl ring" includes pyridyl and piperidinyl, but excluding phenyl. The term "ring" also includes a ring system containing at least one ring, wherein each ring independently meets definition.

Unless otherwise specified, the term "heterocycle" or "heterocyclo" refers to a stable monocyclic, bicyclic or tricyclic ring containing a heteroatom or a heteroatom group, which can be saturated, partially unsaturated or unsaturated (aromatic) and can contain carbon atoms and one, two, three or four ring heteroatoms independently selected from N, O and S, wherein any of heterocycle can be fused to a benzene ring to form a bicyclic ring. Nitrogen and sulfur heteroatoms can optionally be oxidized (i.e., NO and S(O)p, p is 1 or 2). Nitrogen atom can be substituted or unsubstituted (i.e., N or NR, wherein R is H or other substituents already defined herein). The heterocycle can be attached to the pendant group of any heteroatom or carbon atom to form a stable structure. If the resulting compound is stable, the heterocycle described herein may have a substitution at a carbon or nitrogen position. Nitrogen atom on the heterocycle is optionally quaternized. In a preferred embodiment, when the total number of S and O atom of the heterocycle is more than 1, the heteroatom is not adjacent to each other. In another preferred embodiment. The total number of S and O atom of the heterocycle is not more than 1. As used herein, the term "aromatic heterocyclic group" or "heteroaryl" refers to a stable 5-, 6- or 7-membered monocyclic or bicyclic or 7-, 8-, 9- or 10-membered bicyclic heterocyclic aromatic ring which contains carbon atoms and one, two, three or four ring heteroatoms independently selected from N, O and S. Nitrogen atom can be substituted or unsubstituted (i.e., N or NR, wherein R is H or other substituents already defined herein). Nitrogen and sulfur heteroatoms may optionally be oxidized (i.e., NO and S(O)$_p$, p is 1 or 2). It is worth noting that the total number of S and O atom of an aromatic heterocycle is not more than one. The bridged ring is also included in the definition of the heterocycle. A bridged ring is formed when one or more than one atom (i.e., C, O, N or S) link two non-adjacent carbon or nitrogen atoms. A preferred bridged ring includes, but not limited to one carbon atom. Two carbon atoms, one nitrogen atom, two nitrogen atoms and one carbon-nitrogen group. It is worth noting that a bridge always converts a monocyclic ring to a tricyclic ring. In a bridged ring, the substituent on the ring may also be present on the bridge.

Examples of the heterocyclic compound include, but are not limited to: acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzoisoxazolyl, benzoisothiazolyl, benzoimidazolinyl, carbazolyl, 4aH-carbazolyl, carbolinyl, chromanyl, chromene, cinnolinyl decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolinyl, isothiazolyl, isoxazolyl, methylenedioxyphenyl, morpholinyl, naphthyridinyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, hydroxindolyl, pyrimidinyl, phenanthridinyl, phenanthrolinyl, phenazine, phenothiazine, benzoxanthinyl, phenoloxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazolyl, pyrido-imidazolyl, pyrido-thiazolyl, pyridinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolylthienyl, thieno-oxazolyl, thieno-thiazolyl, thieno-imidazolyl, thienyl, triazinyl, 1H-1,2,3-triazolyl, 2H-1,2,4-triazolyl, 1H-1,2,4-triazolyl, 4H-1,2,4-triazolyl and xanthenyl. Also included are fused-ring compounds and spiro compounds.

Unless otherwise specified, the term "hydrocarbyl" or its hyponyms (e.g., alkyl, alkenyl, alkynyl, and aryl, etc.), by itself or as part of another substituent, refers to a linear, branched chain or cyclic hydrocarbon radical or any combination thereof, they can be fully saturated (e.g., alkyl), mono- or polyunsaturated (e.g., alkenyl, alkynyl, and aryl), can be mono-, di- or poly-substituted, can be monovalent (e.g., methyl), divalent (e.g., methylene) or multivalent (e.g., methenyl), can also include a divalent or multivalent group, have a specified number of carbon atom (for example, $C_1$-$C_{12}$ indicates 1 to 12 carbon atoms, $C_{1-12}$ is selected from $C_1$, $C_2$, $C_3$, $C_4$, $C_5$, $C_6$, $C_7$, $C_8$, $C_9$, $C_{10}$, $C_{11}$ and $C_{12}$; $C_{3-12}$ is selected from $C_3$, $C_4$, $C_5$, $C_6$, $C_7$, $C_8$, $C_9$, $C_{10}$, $C_{11}$ and $C_{12}$). The term "hydrocarbyl" includes, but is not limited to aliphatic hydrocarbyl and aromatic hydrocarbyl, the aliphatic hydrocarbyl includes linear and cyclic hydrocarbyl, specifically includes but not limited to alkyl, alkenyl, and alkynyl. The aromatic hydrocarbyl includes but is not limited to 6-12 membered aromatic hydrocarbyl such as phenyl, naphthyl and the like. In some embodiments, the term "hydrocarbyl" refers to a linear or branched group or a combination thereof which can be fully saturated, mono- or polyunsaturated, and can include a divalent or multivalent group. Examples of the saturated hydrocarbyl group include, but are not limited to, methyl, ethyl, n-propyl, isopropyl, n-butyl, tert-butyl, isobutyl, sec-butyl, cyclohexyl, (cyclohexyl)methyl, cyclopropylmethyl, and the homolog or isomer of n-amyl, n-hexyl, n-heptyl, n-octyl and other atom groups. The unsaturated hydrocarbyl has one or more than one double or triple bonds. Examples of the unsaturated alkyl include but are not limited to, vinyl, 2-propenyl, butenyl, crotyl, 2-isopentenyl, 2-(butadienyl), 2,4-pentadienyl, 3-(1,4-pentadienyl), ethynyl, 1- and 3-propynyl, 3-butynyl, and more higher homologs and isomers.

Unless otherwise specified, the term "heterohydrocarbyl" or its hyponyms (such as heteroalkyl, heteroalkenyl, heteroalkynyl, and heteroaryl, etc.), by itself or as part of another substituent, refers to a stable linear, branched or cyclic hydrocarbon group or any combination thereof, which has a specified number of carbon atoms and at least one heteroatom. In some embodiments, the term "heteroalkyl" by itself or in combination with another term refers to a stable linear chain, branched hydrocarbon radical or a combination thereof which has a specified number of carbon atoms and at least one heteroatom. In a specific embodiment, a heteroatom is selected from B, O, N and S, wherein nitrogen and sulfur atoms are optionally oxidized and the nitrogen atom is optionally quaternized. The heteroatom or heteroatom group can be located at any interior position of a heterohydrocarbyl, including the position where the hydrocarbyl attaches to the rest part of the molecule. But the terms "alkoxy", "alkylamino" and "alkylthio" (or thioalkyl) are used by the conventional meaning and refer to an alkyl group connected to the rest part of the molecule via an oxygen atom, an amino or a sulfur atom respectively. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$ and —CH=CH—N($CH_3$)—$CH_3$. Up to two consecutive heteroatoms can be present, such as, —$CH_2$—NH—$OCH_3$.

Unless otherwise specified, the term "cyclohydrocarbyl", "heterocyclohydrocarbyl" or its hyponyms (such as aryl, heteroaryl, cycloalkyl, heterocycloalkyl, cycloalkenyl, heterocycloalkenyl, cycloalkynyl, heterocycloalkynyl, etc.) by itself or in combination with another term refers to cyclized "hydrocarbyl" or "heterohydrocarbyl". Furthermore, for heterohydrocarbyl or heterocyclohydrocarbyl (e.g., heteroalkyl, and heterocycloalkyl), one heteroatom can occupy the position where the heterocycle attaches to the remainder position of the molecule. Examples of the cycloalkyl include, but are not limited to, cyclopentyl, cyclohexyl, 1-cyclohexenyl, 3-cyclohexenyl, cycloheptyl and the like. Non-limiting examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydro-thiophen-2-yl, tetrahydro-thiophen-3-yl, 1-piperazinyl and 2-piperazinyl.

Unless otherwise specified, the term "heterocycloalkyl" by itself or in combination with other terms denotes a cyclized "heteroalkyl", and in addition, with respect to the "heterocycloalkyl", the heteroatom may occupy the attachment position of the heterocycloalkyl group to the remainder of the molecule. In some embodiments, the heterocycloalkyl is 4-6 membered heterocycloalkyl; in other embodiments, the heterocycloalkyl is 5-6 membered heterocycloalkane. Examples of heterocycloalkyl groups include, but are not limited to, azetidinyl, oxetanyl, thietanyl, pyrrolidinyl, pyrazolidinyl, imidazolidinyl, tetrahydrothienyl, tetrahydrofuranyl, tetrahydropyranyl, piperidinyl, piperazinyl, morpholinyl, dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

Unless otherwise specified, the term "alkyl" refers to a linear chain or branched saturated hydrocarbon group, can be mono-substituted (e.g., —$CH_2F$) or poly-substituted (e.g., —$CF_3$), can be monovalent (e.g., methyl), divalent (e.g., methylene) or multivalent (e.g., methenyl). Examples of alkyl include methyl (Me), ethyl (Et), propyl (such as n-propyl and isopropyl), butyl (such as n-butyl, isobutyl, s-butyl, t-butyl), pentyl (such as n-pentyl, isopentyl, neopentyl) and the like.

Unless otherwise specified, cycloalkyl includes any stable cyclic or polycyclic hydrocarbyl, and any carbon atom is saturated, can be mono-substituted or poly-substituted, and can be monovalent, divalent or multivalent. Examples of cycloalkyl include, but are not limited to, cyclopropyl, norbornanyl, [2.2.2]bicyclooctane, [4.4.0]bicyclodecanyl and the like.

Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$) alkyl" is meant to include, but not limited to, trifluoromethyl, 2,2,2-trifluoroethyl, 4-chlorobutyl, 3-bromopropyl and the like. Examples of haloalkyl include, but not limited to trifluoromethyl, trichloromethyl, pentafluoroethyl and pentachloroethyl.

The term "alkoxy" represents any alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. Examples of alkoxy include, but not limited to methoxy, ethoxy, n-propoxy, isopropoxy, n-butoxy, sec-butoxy, tert-butoxy, n-pentyloxy and S-pentoxy.

Unless otherwise specified, the term "aryl" refers to a polyunsaturated aromatic substituent, can be mono-, di- or poly-substituted, can be a monovalent, divalent or multivalent, can be a single ring or a multiple ring (e.g., one to three rings; wherein at least one ring is aromatic), which are fused together or connected covalently. The term "heteroaryl" refers to an aryl (or ring) containing one to four heteroatoms. In an illustrative example, the heteroatom is selected from B, O, N and S, wherein nitrogen and sulfur atoms are optionally oxidized and nitrogen atom is optionally quaternized. A heteroaryl may attach to the rest part of a molecule via a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furanyl, thienyl, pyridyl, pyrimidinyl benzothiazolyl, purinyl, benzimidazolyl, indolyl, isoquinolyl, quinoxalinyl, quinolyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl. The substituent of any of aryl and heteroaryl ring system is selected from the acceptable substituent described below.

Unless otherwise specified, when aryl combines with other terms (such as aryloxy, arylthio, arylalkyl), the aryl includes the aryl and heteroaryl ring as defined above. Thus, the term "aralkyl" is meant to include the group (e.g., benzyl, phenethyl, pyridylmethyl, etc.) where an aryl is attached to an alkyl, including an alkyl where the carbon atom (e.g., methylene) has been replaced by an atom such as oxygen, for example, phenoxymethyl, 2-pyridyloxy, 3-(1-naphthyloxy)propyl, and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compound of the present disclosure can be prepared by a variety of synthetic methods well known to the skilled in the art, including the following enumerative embodiment, the embodiment formed by the following enumerative embodiment in combination with other chemical synthesis methods and the equivalent replacement well known to the skilled in the art. The preferred embodiment includes, but is not limited to the embodiment of the present disclosure.

The compounds of the present disclosure may have various uses or indications, including but not limited to the specific uses or indications listed in the present application.

The solvent used in the present disclosure is commercially available. The present disclosure employs the following abbreviations: aq stands for water; HATU stands for O-(7-azabenzotriazol-1-yl)-N,N,N',N'-tetramethyluronium hexafluoro-phosphate; EDC stands for N-(3-dimethylaminopropyl)-N'-ethylcarbodiimide hydrochloride; m-CPBA stands for 3-chloroperoxybenzoic acid; eq stands for equivalent, equivalent; CDI stands for carbonyldiimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc stands for acetic acid esters; EtOH stands for ethanol; MeOH for methanol; CBz stands for benzyloxycarbonyl, which is an amine protecting group; BOC stands for tert-butoxycarbonyl, which is an amine protecting group; HOAc stands for acetic acid; NaCNBH$_3$ stands for sodium cyanoborohydride; Rt stands for room temperature; O/N stands for overnight; THF stands for tetrahydrofuran; Boc$_2$O stands for di-tert-butyldicarbonate; TFA stands for trifluoroacetic acid; DIPEA stands for diisopropylethylamine; SOCl$_2$ stands for thionyl chloride; CS$_2$ stands for carbon disulfide; TsOH stands for p-toluenesulfonic acid; NFSI stands for N-fluoro-N-(phenylsulfonyl) benzenesulfonamide; NC S stands for 1-chloropyrrolidine-2,5-dione; n-Bu4NF stands for tetrabutylammonium; iPrOH stands for 2-propanol; mp stands for melting point; LDA stands for diisopropylamino lithium; DEA stands for diethylamine; ACN stands for acetonitrile.

Compounds are named manually or by ChemDraw® software, the commercially available compounds use their vendor directory names.

Technical effects: the compounds of the present disclosure all exhibit very high antagonist activity against the human ET$_A$ receptors in vitro, and the selectivity for ET$_A$/ET$_B$ is more than 10000-fold; the compounds of the disclosure are superior to the control compound macitentan in characterization experiments of PXR mediated induction of CYP3A expression. In characterizing experiments of the inhibitory effect on 5 major isozymes of human liver microsomal cytochrome P450, the compounds of the present disclosure are superior to macitentan; the inhibitory effect of the compounds of the present disclosure on bile salt export pumps is much weaker than macitentan, thereby significantly reducing the risk of developing hepatotoxicity. The compounds of the present disclosure have good pharmacokinetic properties in both SD rats and beagle dogs.

DETAILED DESCRIPTION OF THE PREFERRED EMBODIMENT

The following examples further illustrate the present disclosure, but the present disclosure is not limited thereto. The present disclosure has been described in detail in the text, and its specific embodiments have also been disclosed, for one skilled in the art, it is obvious to modify and improve the embodiments of the present disclosure within the spirit and scope of the present disclosure.

Reference Embodiment 1: Fragment BB-1

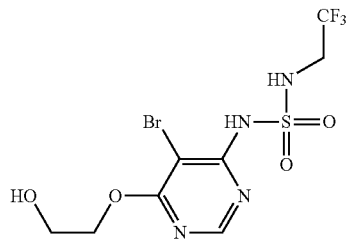 [SMILES: O=S(=O)(NCC(F)(F)F)Nc1ncnc(OCCO)c1Br]

Synthetic Route:

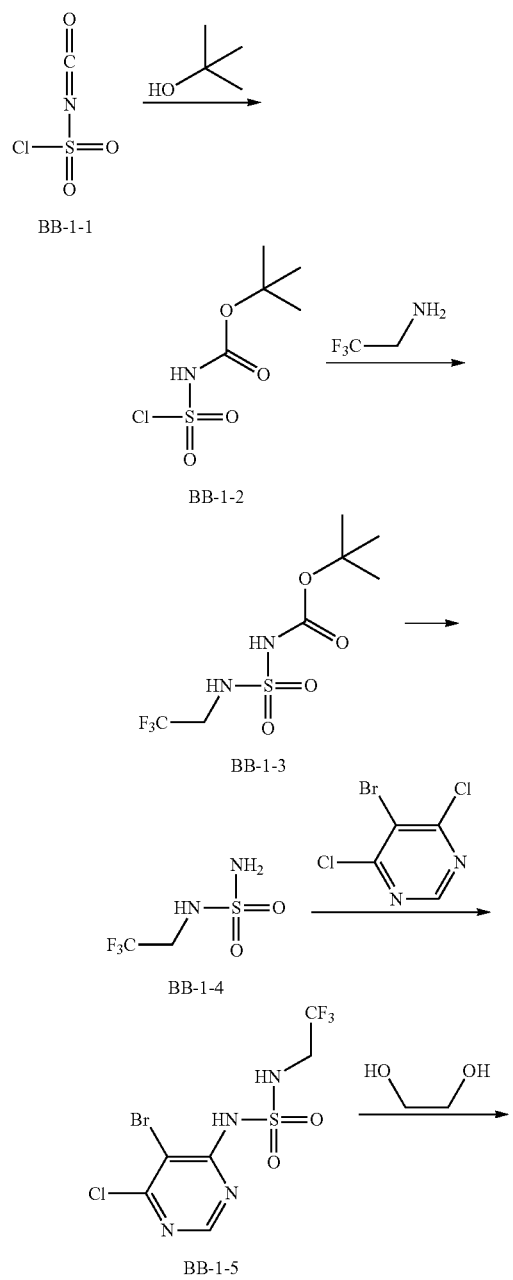

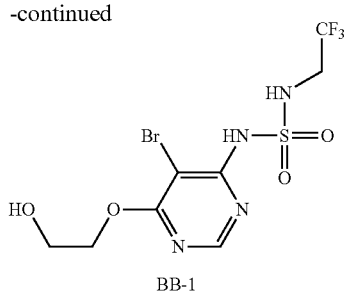

Step 1: Synthesis of Compound BB-1-2

At room temperature, compound BB-1-1 (30.00 g, 211.97 mmol, 18.40 mL) was dissolved in dichloromethane (200 mL), then the mixture was cooled to 0° C., a solution of tert-butanol (15.71 g, 211.97 mmol, 20.40 mL) in dichloromethane (100 mL) was slowly added dropwise (dropping time was about 1 hour), and the reaction mixture was warmed to room temperature and stirred for 1 hour. The target compound BB-1-2 (crude product) was retained in the reaction solvent dichloromethane and used directly in the next reaction.

Step 2: Synthesis of Compound BB-1-3

At room temperature, compound 2,2,2-trifluoroethylamine (8.00 g, 80.77 mmol, 6.35 mL) and triethylamine (24.52 g, 242.30 mmol, 33.59 mL) were dissolved in dichloromethane (100.00 mL), then the mixture was cooled to 0° C., and a solution of compound BB-1-2 (80.77 mmol, crude product) in dichloromethane was slowly added dropwise (dropping time was about 1 hour), and the reaction mixture was warmed to room temperature and stirred for 14 hours. After the reaction was completed, the solvent was removed under reduced pressure, the residue was added with water (150 mL), extracted with dichloromethane (100 mL), and the organic phase was discarded. The aqueous phase was adjusted to pH of 5-6 with 1M dilute hydrochloric acid and extracted with ethyl acetate (100 mL×3). The organic phases were combined, dried over anhydrous sodium sulfate, filtered, and the solvent was removed under reduced pressure to obtain the target compound BB-1-3 (white solid, 15.00 g, crude product). $^1$H NMR (400 MHz, DMSO_$d_6$) δ: 3.55 (q, J=9.8 Hz, 2H), 1.37 (s, 9H).

Step 3: Synthesis of Compound BB-1-4

At room temperature, the compound BB-1-3 (15.00 g, 53.91 mmol) was added to water (150.00 mL), and the reaction mixture was heated to 110° C. and stirred for 1 hour. After the reaction was completed, the reaction mixture was cooled to room temperature and extracted with ethyl acetate (100 mL×3). The organic phases were combined, washed with brine (100 mL), dried over anhydrous sodium sulfate, filtered, and the solvent of filtrate was removed under reduced pressure to obtain the target compound BB-1-4 (yellow solid, 7.50 g, crude product). $^1$H NMR (400 MHz, DMSO_$d_6$) δ: 7.51 (t, J=7.0 Hz, 1H), 6.83 (s, 2H), 3.69-3.54 (m, 2H). $^{19}$F NMR (400 MHz, DMSO_$d_6$) δ: −70.81 (s, 3F).

Step 4: Synthesis of Compound BB-1-5

At room temperature, the compound BB-1-4 (1.56 g, 8.78 mmol) and potassium tert-butoxide (1.97 g, 17.55 mmol) were dissolved in dimethyl sulfoxide (80.00 mL), and the reaction mixture was stirred for 1 hour under nitrogen atmosphere at room temperature. Then 5-bromo-4,6-dichloropyrimidine (2.00 g, 8.78 mmol) was added to reaction mixture, and the reaction mixture was further stirred at room temperature for 10 hours. After the reaction was completed, water (100 mL) was added, the pH was adjusted to 5-6 with 1 M diluted hydrochloric acid, and the mixture was extracted with ethyl acetate (50 mL×3). The organic phases were combined, washed with water (50 mL×2), dried over anhydrous sodium sulfate, filtered, and the solvent of filtrate was removed under reduced pressure. The residue was separated by column chromatography (eluent: petroleum ether/ethyl acetate=10/1-4/1, volume ratio) to obtain the target compound BB-1-5 (yellow solid, 1.90 g, yield: 58.56%). $^1$H NMR (400 MHz, DMSO_d$_6$) δ: 8.60 (s, 1H), 7.51 (t, J=7.0 Hz, 1H), 6.83 (s, 1H), 3.84 (q, J=9.6 Hz, 2H).

Step 5: Synthesis of Compound BB-1

At room temperature, potassium tert-butoxide (1.73 g, 15.42 mmol) was added to ethylene glycol (52.68 g, 848.46 mmol, 47.46 mL) and ethylene glycol dimethyl ether (10 mL), and the reaction mixture was heated to 40° C. under nitrogen atmosphere and stirred for 0.5 hour, a solution of compound BB-1-5 (1.90 g, 5.14 mmol) in ethylene glycol dimethyl ether (20 mL) was added to solution, and the reaction mixture was heated to 100° C. and stirred for 16 hours under nitrogen atmosphere. After the reaction was completed, the reaction solution was cooled to room temperature, water (100 mL) was added, the pH was adjusted to 5-6 with 2M dilute hydrochloric acid, then the mixture was extracted with ethyl acetate (60 mL×3). The organic phases were combined, dried over anhydrous sodium sulfate, filtered, and the solvent of filtrate was removed under reduced pressure. The residue was separated by column chromatography (eluent: petroleum ether/ethyl acetate=8/1-3/1, volume ratio) to obtain target compound BB-1 (yellow solid, 1.55 g, yield: 76.31%). MS-ESI m/z: 394.7 [M+H]$^+$, 396.7 [M+H+2]$^+$. $^1$H NMR (400 MHz, CDCl$_3$) δ: 8.33 (s, 1H), 6.04 (s, 1H), 4.53 (t, J=4.4 Hz, 2H), 3.93 (t, J=4.4 Hz, 2H), 3.67 (q, J=8.6 Hz, 2H). $^{19}$F NMR (400 MHz, CDCl$_3$) δ: −71.87 (s, 3F).

Reference Embodiment 2: Fragment BB-2

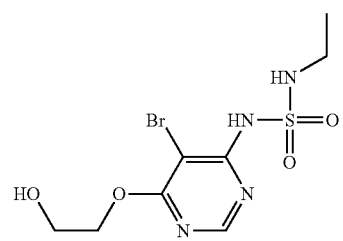 [SMILES: CCNS(=O)(=O)Nc1ncnc(OCCO)c1Br]

Synthetic Route:

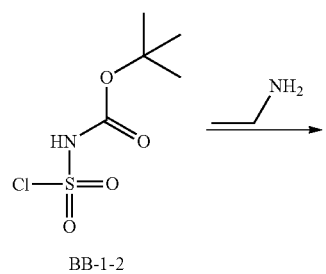

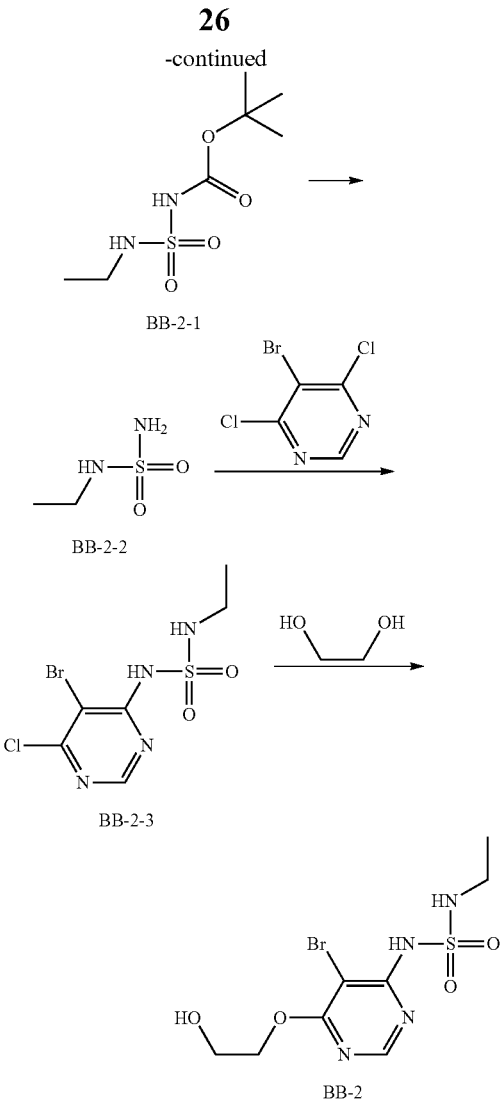

Step 1: Synthesis of Compound BB-2-1

At room temperature, ethylamine hydrochloride (5.00 g, 61.32 mmol) and triethylamine (18.61 g, 183.96 mmol, 25.49 mL) were added to dichloromethane (100.00 mL), then the reaction mixture was cooled to 0° C., and a solution of compound BB-1-2 (61.32 mmol, crude product) in dichloromethane was slowly added dropwise (dropping time was about 1 hour), and the reaction mixture was warmed to room temperature and stirred for 16 hours. After the reaction was completed, the solvent was removed under reduced pressure. The residue was added with water (150 mL), extracted with dichloromethane (100 mL), and the organic phase was discarded. The aqueous phase was adjusted to pH of 5-6 with 1M dilute hydrochloric acid and extracted with ethyl acetate (100 mL×3). The organic phases were combined, dried over anhydrous sodium sulfate, filtered, then the solvent was removed under reduced pressure to obtain the target compound BB-2-1 (white solid, 6.00 g, crude product). $^1$H NMR (400 MHz, CDCl$_3$) δ: 5.07 (t, J=5.6 Hz, 1H), 3.13-3.01 (m, 2H), 1.43 (s, 9H), 1.16 (t, J=7.3 Hz, 3H).

Step 2: Synthesis of Compound BB-2-2

At room temperature, the compound BB-2-1 (7.02 g, 31.30 mmol) was added to water (200.00 mL) and the reaction mixture was heated to 110° C. and stirred for 1 hour. After the reaction was completed, the reaction mixture was cooled to room temperature and extracted with ethyl acetate (100 mL×3). The organic phases were combined, washed with saturated brine (50 mL), dried over anhydrous sodium sulfate, filtered, and the solvent of filtrate was removed under reduced pressure to obtain the target compound BB-2-2 (yellow oil, 2.87 g, crude product). $^1$H NMR (400 MHz, CDCl$_3$) δ: 4.80 (s, 2H), 4.57 (s, 1H), 3.23-3.14 (m, 2H), 1.24 (t, J=7.3 Hz, 3H).

Step 3: Synthesis of Compound BB-2-3

At room temperature, the compound BB-2-2 (2.87 g, 23.12 mmol) and potassium tert-butoxide (5.19 g, 46.24 mmol) were added to dimethyl sulfoxide (80.00 mL), then 5-bromo-4,6-dichloropyrimidine (5.27 g, 23.12 mmol) was added to the reaction mixture, and the reaction mixture was stirred at room temperature for 10 hours under nitrogen atmosphere. After the reaction was completed, water (150 mL) was added, the pH was adjusted to 5-6 with 1M dilute hydrochloric acid, and the solution was extracted with ethyl acetate (100 mL×3). The organic phases were combined, washed with water (50 mL×2), dried over anhydrous sodium sulfate, filtered, and the solvent of filtrate was removed under reduced pressure. The residue was separated by column chromatography (eluent: petroleum ether/ethyl acetate=10/1-4/1, volume ratio) to obtain the target compound BB-2-3 (yellow solid, 2.40 g, yield: 32.89%). $^1$H NMR (400 MHz, DMSO_d$_6$) δ: 8.59 (s, 1H), 2.96 (q, J=7.1 Hz, 2H), 1.02 (t, J=7.0 Hz, 3H).

Step 4: Synthesis of Compound BB-2

At room temperature, potassium tert-butoxide (1.50 g, 13.41 mmol) was added to a mixture solution of ethylene glycol (33.30 g, 536.49 mmol, 30.00 mL) and ethylene glycol dimethyl ether (10 mL), the reaction mixture was heated to 40° C. and stirred for 0.5 hours under nitrogen atmosphere, then a solution of compound BB-2-3 (1.41 g, 4.47 mmol) in ethylene glycol dimethyl ether (20 mL) was added to the solution in one portion, and the reaction mixture was heated to 100° C. and stirred for 16 hours. After the reaction was completed, the reaction mixture was cooled to room temperature, water (100 mL) was added, pH was adjusted to 5-6 with 2M dilute hydrochloric acid, then the mixture was extracted with ethyl acetate (60 mL×3). The organic phases were combined, dried over anhydrous sodium sulfate, filtered, and the solvent of filtrate was removed under reduced pressure. The residue was separated by column chromatography (eluent: petroleum ether/ethyl acetate=8/1-3/1, volume ratio) to obtain the target compound BB-2 (yellow solid, 1.36 g, yield: 87.21%). MS-ESI m/z: 340.7 [M+H]$^+$, 342.7 [M+H+2]$^+$. $^1$H NMR (400 MHz, CDCl$_3$) δ: 8.38 (s, 1H), 7.66 (s, 1H), 5.54 (t, J=5.9 Hz, 1H), 4.60 (t, J=4.8 Hz, 2H), 4.00 (t, J=4.0 Hz, 2H), 3.19-3.03 (m, 2H), 2.45 (br s, 1H), 1.21 (t, J=7.2 Hz, 3H).

Reference Embodiment 3: Fragment BB-3

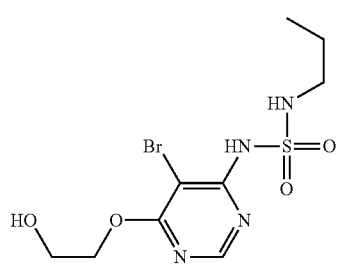 [SMILES: CCCNS(=O)(=O)Nc1ncnc(OCCO)c1Br]

Synthetic Route:

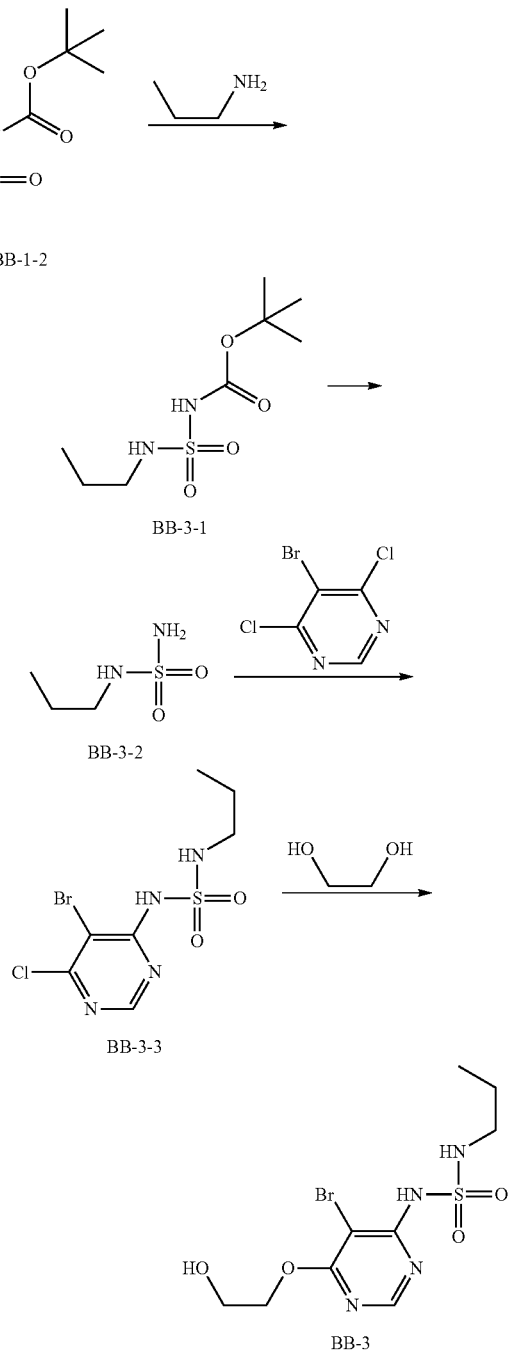

Step 1: Synthesis of Compound BB-3-1

At room temperature, n-propylamine (7.61 g, 128.70 mmol, 10.57 mL) and triethylamine (14.21 g, 140.40 mmol, 19.47 mL) were dissolved in dichloromethane (100.00 mL), then the mixture was cooled to 0° C., then a solution of the compound BB-1-2 (117.00 mmol, crude product) in dichloromethane was slowly added to the reaction solution (dropping time was about 0.5 hour), and the reaction mixture was stirred at room temperature for 18 hours under nitrogen atmosphere. After the reaction was completed, water (200 mL) was added, and the mixture was extracted with dichloromethane (200 mL×2). The organic phases were combined, washed with 1M dilute hydrochloric acid (50 mL) and saturated brine (200 mL), dried over anhydrous sodium sulfate, filtered, and the solvent of filtrate was removed under reduced pressure to obtain the target compound BB-3-1 (white solid, 21.00 g, yield: 75.32%). $^1$H NMR (400 MHz, CDCl$_3$) δ: 2.93 (t, J=7.0 Hz, 2H), 1.58-1.48 (m, 2H), 1.46-1.37 (s, 9H), 0.88 (t, J=7.4 Hz, 3H).

Step 2: Synthesis of Compound BB-3-2

At room temperature, the compound BB-3-1 (20.00 g, 83.93 mmol) was added to water (100.00 mL), and the reaction mixture was heated to 100° C. and stirred for 1 hour under nitrogen atmosphere. After the reaction was completed, the reaction solution was cooled to room temperature and extracted with ethyl acetate (100 mL×3). The organic phases were combined, washed with saturated brine (100 mL), dried over anhydrous sodium sulfate, filtered, and the solvent was removed under reduced pressure to obtain the target compound BB-3-2 (colorless oil, 10.00 g, yield: 86.22%). $^1$H NMR (400 MHz, DMSO_d$_6$) δ: 6.44 (s, 2H), 2.88-2.78 (m, 2H), 1.52-1.43 (m, 2H), 0.87 (t, J=7.5 Hz, 3H).

Step 3: Synthesis of Compound BB-3-3

At room temperature, the compound BB-3-2 (18.19 g, 131.66 mmol) was dissolved in dimethyl sulfoxide (300.00 mL), then potassium tert-butoxide (19.70 g, 175.54 mmol) was added, and the reaction mixture was stirred at room temperature for 0.5 hour. Then, 5-bromo-4,6-dichloropyrimidine (20.00 g, 87.77 mmol) was added to reaction solution, and the reaction mixture was further stirred at room temperature for 48 hours. After the reaction was completed, saturated brine (1000 mL) was added, the pH was adjusted to 4-5 with 10% dilute hydrochloric acid, and the mixture was extracted with ethyl acetate (500 mL×3). The organic phases were combined, dried over anhydrous sodium sulfate, filtered, and the solvent of filtrate was removed under reduced pressure. The residue was separated by column chromatography (eluent: petroleum ether/ethyl acetate=10/1-1/1, volume ratio) to obtain the target compound BB-3-3 (white solid, 15.00 g, yield: 51.85%). $^1$H NMR (400 MHz, CDCl$_3$) δ: 8.58 (s, 1H), 7.84 (s, 1H), 5.52-5.54 (m, 1H), 3.07 (q, J=6.8 Hz, 2H), 1.59-1.64 (m, 2H), 0.96 (t, J=7.2 Hz, 3H).

Step 4: Synthesis of Compound BB-3

At room temperature, potassium tert-butoxide (10.21 g, 91.02 mmol) was added to ethylene glycol (56.50 g, 910.19 mmol), and the reaction mixture was heated to 40° C. and stirred for 0.5 hour under nitrogen atmosphere. Then a solution of the compound BB-3-3 (15.00 g, 45.51 mmol) in ethylene glycol dimethyl ether (50.00 mL) was added to solution, and the reaction mixture was heated to 100° C. and stirred for 48 hours under nitrogen atmosphere. After the reaction was completed, the mixture was cooled to room temperature, water was added (200 mL), the pH was adjusted to 4 with 1M dilute hydrochloric acid, and the mixture was extracted with ethyl acetate (200 mL×3). The organic phases were combined, washed with saturated brine (200 mL), dried over anhydrous sodium sulfate, and filtered, the solvent of filtrate was removed under reduced pressure, and the residue was separated by column chromatography (eluent: petroleum ether/ethyl acetate=10/1-1/1, volume ratio) to obtain the target compound BB-3 (yellow solid, 7.10 g, yield: 40.13%). MS-ESI m/z: 354.8 [M+H]$^+$, 356.8 [M+H+2]$^+$. $^1$H NMR (400 MHz, CDCl$_3$) δ: 8.39 (s, 1H), 7.68 (s, 1H), 5.59-5.62 (m, 1H), 4.83-4.75 (m, 2H), 4.02-4.00 (m, 2H), 3.04 (q, J=6.8 Hz, 2H), 2.05 (br s, 1H) 1.63-1.57 (m, 2H), 0.95 (t, J=7.2 Hz, 3H).

Reference Embodiment 4: Fragment BB-4

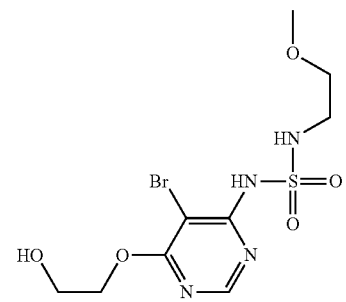 [SMILES: COCCNS(=O)(=O)Nc1ncnc(OCCO)c1Br]

Synthetic Route:

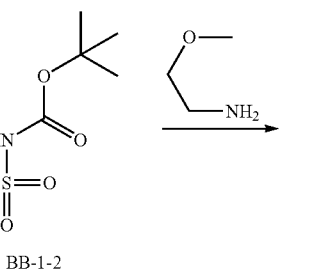

BB-1-2

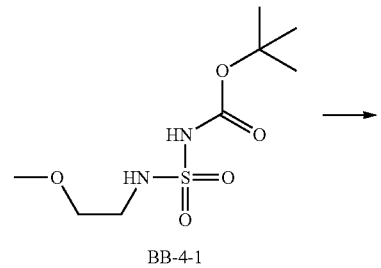

BB-4-1

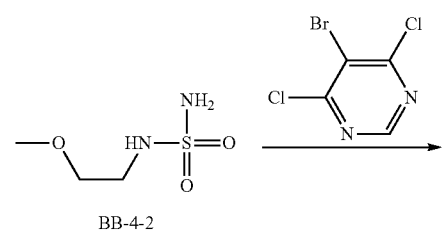

BB-4-2

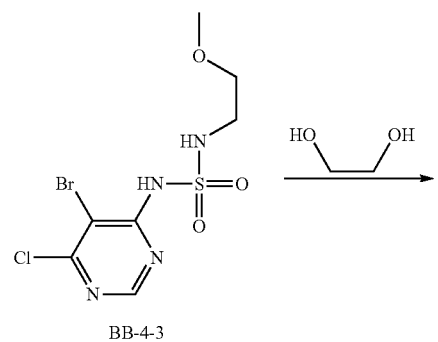

BB-4-3

-continued

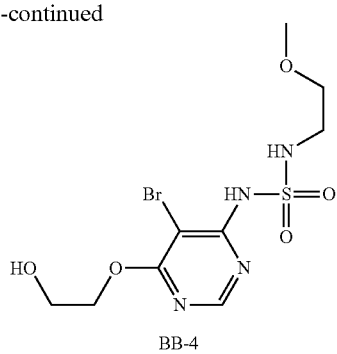

BB-4

Step 1: Synthesis of Compound BB-4-1

At room temperature, compound 2-methoxyethylamine (2.00 g, 26.63 mmol, 2.33 mL) and triethylamine (5.39 g, 53.26 mmol, 7.38 mL) were dissolved in dichloromethane (100.00 mL), and then the reaction mixture was cooled to 0° C., a solution of the compound BB-1-2 (26.63 mmol, crude product) in dichloromethane was slowly added to reaction solution (dropping time was about 0.5 hour), and the reaction mixture was warmed to room temperature and stirred for 15 hours. After the reaction was completed, the solvent was removed under reduced pressure, and the residue was added with water (100 mL), the pH was adjusted to 5 with 1M hydrochloric acid, and the mixture was extracted with ethyl acetate (100 mL×3). The organic phases were combined, washed with saturated brine (100 mL), dried over anhydrous sodium sulfate, filtered, and the solvent of filtrate was removed under reduced pressure to obtain the target compound BB-4-1 (white solid, 6.00 g, yield: 88.59%). $^1$H NMR (400 MHz, CDCl$_3$) δ: 7.37 (s, 1H), 5.50 (br s, 1H), 3.53 (t, J=5.0 Hz, 2H), 3.40 (s, 3H), 3.26 (d, J=4.8 Hz, 2H), 1.51 (s, 9H).

Step 2: Synthesis of Compound BB-4-2

At room temperature, the compound BB-4-1 (6.00 g, 23.59 mmol) was added to water (100.00 mL), and the reaction mixture was heated to 100° C. and stirred for 1 hour. After the reaction was completed, the mixture was cooled to room temperature and extracted with ethyl acetate (100 mL×3). The organic phases were combined, washed with saturated brine (100 mL), dried over anhydrous sodium sulfate, filtered, and the solvent of filtrate was removed under reduced pressure to obtain the target compound BB-4-2 (yellow solid, 2.00 g, yield: 54.99%). $^1$H NMR (400 MHz, CDCl$_3$) δ: 5.52 (br s, 2H), 3.58-3.48 (m, 2H), 3.41-3.19 (m, 5H).

Step 3: Synthesis of Compound BB-4-3

At room temperature, the compound BB-4-2 (1.12 g, 7.24 mmol) and potassium tert-butoxide (2.22 g, 19.75 mmol) were added to dimethyl sulfoxide (20.00 mL), and the reaction mixture was stirred at room temperature for 0.5 hour, then 5-bromo-4,6-dichloropyrimidine (1.50 g, 6.58 mmol) was added to reaction solution, and the reaction mixture was further stirred at room temperature for 6 hours. After the reaction was completed, water (100 mL) was added, the pH was adjusted to 6 with 1M dilute hydrochloric acid, and the mixture was extracted with ethyl acetate (100 mL×3). The organic phases were combined, washed with saturated brine (100 mL), dried over anhydrous sodium sulfate, filtered, and the solvent of filtrate was removed under reduced pressure. The residue was separated by column chromatography (eluent: dichloromethane/methanol=30/1, volume ratio) to obtain the target compound BB-4-3 (yellow solid, 1.40 g, yield: 61.56%). $^1$H NMR (400 MHz, CDCl$_3$) δ: 8.57 (s, 1H), 7.89 (br s, 1H), 5.99 (br s, 1H), 3.36 (br d, J=2.3 Hz, 2H), 3.32-3.20 (m, 5H).

Step 4: Synthesis of Compound BB-4

At room temperature, potassium tert-butoxide (1.36 g, 12.15 mmol) was added to ethylene glycol (22.20 g, 357.66 mmol, 20.00 mL), the reaction mixture was heated to 40° C. and stirred for 0.5 hour, and then the solution of compound BB-4 3 (1.40 g, 4.05 mmol) in ethylene glycol dimethyl ether (10.00 mL) was added to solution, and the reaction mixture was heated to 110° C. and stirred for 12 hours. After the reaction was completed, the mixture was cooled to room temperature, water (50 mL) was added, the pH was adjusted to 3 with 1M dilute hydrochloric acid, and the mixture was extracted with ethyl acetate (50 mL×3). The organic phases were combined, washed with saturated brine (50 mL), dried over anhydrous sodium sulfate, filtered, and the solvent of filtrate was removed under reduced pressure. The residue was separated by column chromatography (eluent: methylene chloride/methanol=20/1, volume ratio) to obtain the target compound BB-4 (yellow solid, 1.20 g, yield: 76.63%). MS-ESI m/z: 370.8 [M+H]$^+$, 372.8 [M+H]$^+$. $^1$H NMR (400 MHz, CDCl$_3$) δ: 8.39 (s, 1H), 7.64 (br s, 1H), 6.03-5.94 (m, 1H), 4.65-4.54 (m, 2H), 3.99 (d, J=3.0 Hz, 2H), 3.49 (t, J=5.0 Hz, 2H), 3.33-3.19 (m, 5H), 2.39 (t, J=5.3 Hz, 1H).

Reference Embodiment 5: Fragment BB-5

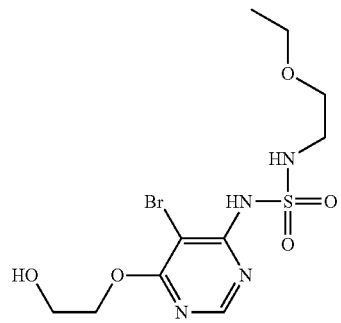 [SMILES: CCOCCNS(=O)(=O)Nc1ncnc(OCCO)c1Br]

Synthetic Route:

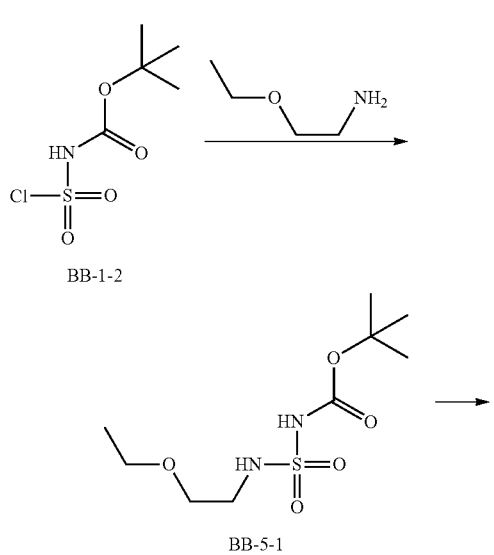

BB-1-2

BB-5-1

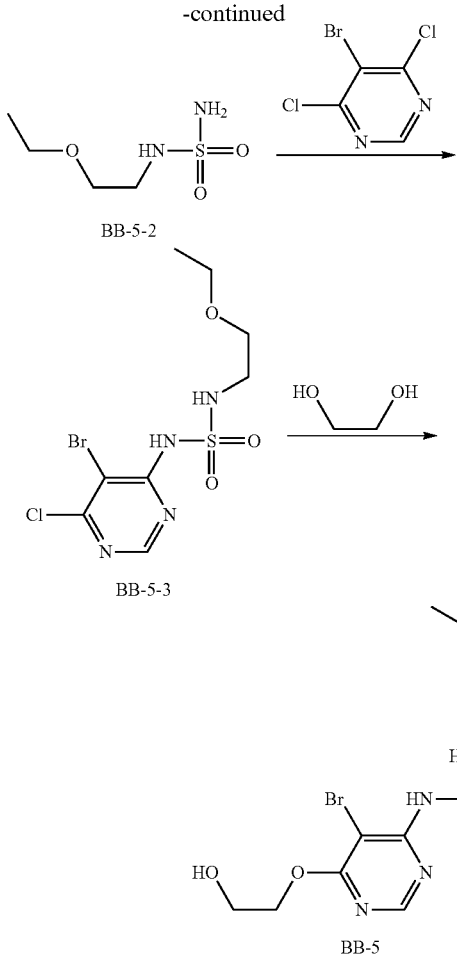

Step 1: Synthesis of Compound BB-5-1

At room temperature, compound 2-ethoxyethylamine (5.00 g, 56.09 mmol) and triethylamine (11.35 g, 112.18 mmol, 15.55 mL) were dissolved in dichloromethane (50.00 mL) under nitrogen atmosphere, the mixture was cooled to 0° C., and then a solution of the compound BB-1-2 (56.09 mmol, crude product) in dichloromethane was added dropwise to reaction solution, and the reaction mixture was stirred at room temperature for 12 hours under nitrogen atmosphere. After the reaction was completed, water (80 mL) was added, and the mixture was extracted with dichloromethane (80 mL×2). The organic phases were combined, washed with 1M dilute hydrochloric acid (50 mL) and saturated brine (200 mL), dried over anhydrous sodium sulfate, filtered, and the solvent was removed under reduced pressure to obtain the target compound BB-5-1 (white solid, 11.00 g, yield: 73.09%). $^1$H NMR (400 MHz, CDCl$_3$) δ: 7.41 (s, 1H), 5.43 (t, J=5.7 Hz, 1H), 3.50 (t, J=5.0 Hz, 2H), 3.46-3.40 (m, 2H), 3.19 (q, J=5.5 Hz, 2H), 1.44 (s, 9H), 1.14 (t, J=7.0 Hz, 3H).

Step 2: Synthesis of Compound BB-5-2

At room temperature, compound BB-5-1 (10.00 g, 37.27 mmol) was added to water (100.00 mL), and the reaction mixture was heated to 100° C. and stirred for 12 hours. After the reaction was completed, the mixture was cooled to room temperature and extracted with ethyl acetate (80 mL×3). The organic phases were combined, washed with saturated brine (100 mL×2), dried over anhydrous sodium sulfate, filtered, and the solvent was removed under reduced pressure to obtain the target compound BB-5-2 (white solid, 5.20 g, yield: 82.95%). $^1$H NMR (400 MHz, CDCl$_3$) δ: 5.02 (t, J=5.8 Hz, 1H), 5.00-4.88 (m, 2H), 3.63-3.57 (m, 2H), 3.55 (d, J=7.0 Hz, 2H), 3.33 (d, J=5.0 Hz, 2H), 1.22 (t, J=6.2 Hz, 3H).

Step 3: Synthesis of Compound BB-5-3

At room temperature, the compound BB-5-2 (5.00 g, 29.72 mmol) and potassium tert-butoxide (10.01 g, 89.17 mmol) were added to dimethyl sulfoxide (50.00 mL), and the reaction mixture was heated to 35° C. and stirred for 0.5 hour, then 5-bromo-4,6-dichloropyrimidine (6.77 g, 29.72 mmol) was added to reaction solution, and the reaction mixture was further stirred at 35° C. for 12 hours. After the reaction was completed, hydrochloric acid (0.5 M, 50 mL) was added, and the mixture was extracted with ethyl acetate (50 mL×3). The organic phases were combined, washed with saturated brine (100 mL×2), dried over anhydrous sodium sulfate, filtered, and the solvent of filtrate was removed under reduced pressure. The residue was separated by column chromatography (eluent: petroleum ether/ethyl acetate=10/1-3/1, volume ratio) to obtain the target compound BB-5-3 (light yellow solid, 2.10 g, yield: 16.76%). MS-ESI m/z: 358.9 [M+H]$^+$, 360.8 [M+H+2]$^+$. $^1$H NMR (400 MHz, CDCl$_3$) δ: 8.49 (s, 1H), 7.82 (s, 1H), 5.99 (t, J=5.5 Hz, 1H), 3.47-3.43 (m, 2H), 3.34 (d, J=7.0 Hz, 2H), 3.18 (d, J=4.7 Hz, 2H), 1.05 (t, J=6.9 Hz, 3H).

Step 4: Synthesis of Compound BB-5

At room temperature, potassium tert-butoxide (1.87 g, 16.68 mmol) was added to ethylene glycol (33.30 g, 536.49 mmol, 30.00 mL), the reaction mixture was heated to 40° C. and stirred for 0.5 hour under nitrogen atmosphere, then a solution of compound BB-5-3 (2.00 g, 5.56 mmol) in ethylene glycol dimethyl ether (20.00 mL) was added to solution, and the reaction mixture was heated to 110° C. and stirred for 12 hours under nitrogen atmosphere. After the reaction was completed, the mixture was cooled to room temperature, hydrochloric acid (0.5M, 50 mL) was added, and the mixture was extracted with ethyl acetate (50 mL×3). The organic phases were combined, washed with saturated brine (100 mL×2), dried over anhydrous sodium sulfate, filtered, and the solvent of filtrate was removed under reduced pressure. The residue was separated by column chromatography (eluent: petroleum ether/ethyl acetate=10/1-1/1, volume ratio) to obtain the target compound BB-5 (light yellow solid, 1.30 g, yield: 60.69%). $^1$H NMR (400 MHz, CDCl$_3$) δ: 8.38 (s, 1H), 7.67 (br s, 1H), 6.09 (d, J=5.0 Hz, 1H), 4.72-4.52 (m, 2H), 4.00 (br s, 2H), 3.62-3.50 (m, 2H), 3.47-3.36 (m, 2H), 3.31-3.20 (m, 2H), 2.46 (br s, 1H), 1.21-1.05 (m, 3H).

Reference Embodiment 6: Fragment BB-6

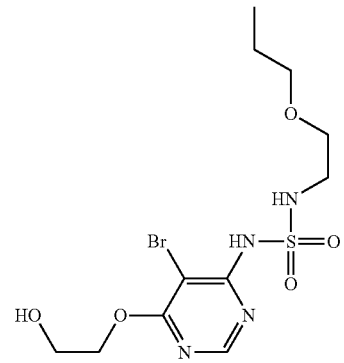 [SMILES: CCCOCCNS(=O)(=O)Nc1ncnc(OCCO)c1Br]

Synthetic Route:

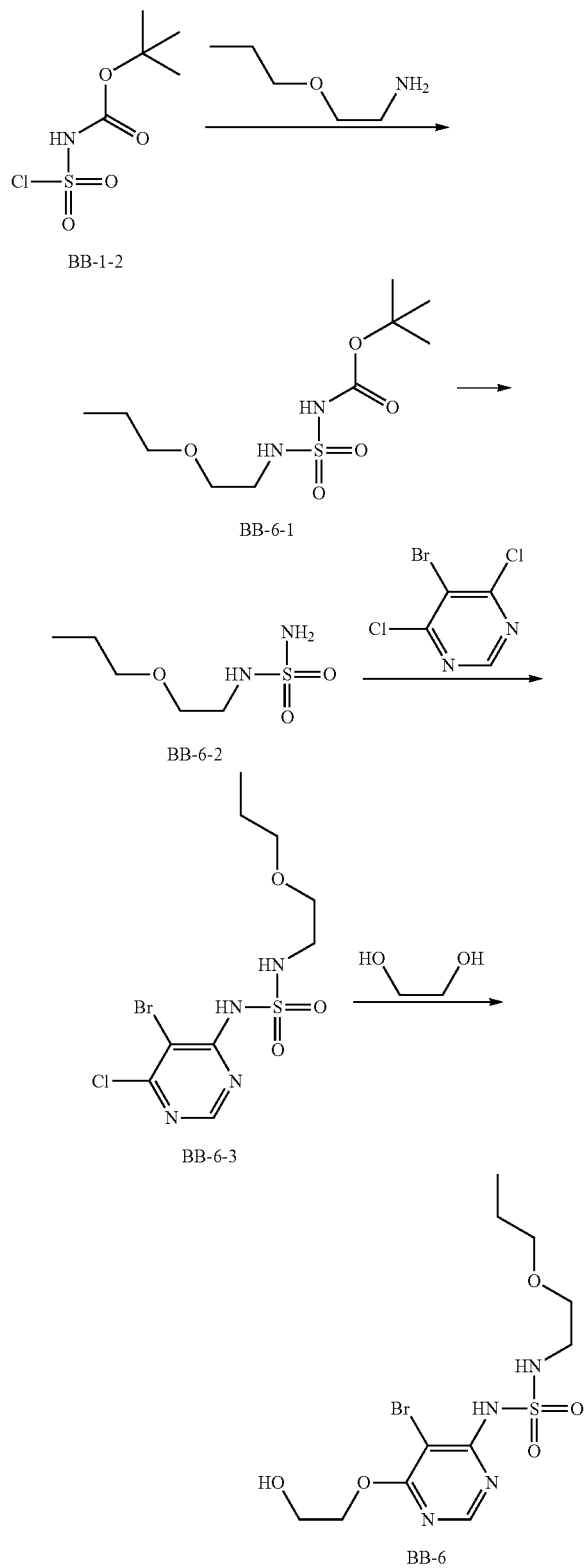

Step 1: Synthesis of Compound BB-6-1

At room temperature, compound 2-n-propoxyethylamine (5.00 g, 48.47 mmol) and triethylamine (9.81 g, 96.94 mmol, 13.44 mL) were dissolved in dichloromethane (50.00 mL), the reaction mixture was cooled to 0° C. under nitrogen atmosphere, and then a solution of compound BB-1-2 (48.47 mmol, crude product) in dichloromethane was slowly added dropwise to reaction solution, and the reaction mixture was warmed to room temperature and stirred for 12 hours. After the reaction was completed, water (80 mL) was added, and the mixture was extracted with dichloromethane (80 mL×2). The organic phases were combined, washed with 1M dilute hydrochloric acid (50 mL) and saturated brine (200 mL), dried over anhydrous sodium sulfate, filtered, and the solvent was removed under reduced pressure to obtain the target compound BB-6-1 (white solid, 11.00 g, yield: 80.37%).

Step 2: Synthesis of Compound BB-6-2

At room temperature, the compound BB-6-1 (11.00 g, 38.96 mmol) was added to water (100.00 mL), and the reaction mixture was heated to 100° C. and stirred for 2 hours. After the reaction was completed, the mixture was cooled to room temperature and extracted with ethyl acetate (80 mL×3). The organic phases were combined, washed with saturated brine (100 mL×2), dried over anhydrous sodium sulfate, filtered, and the solvent was removed under reduced pressure to obtain the target compound BB-6-2 (white solid, 5.60 g, yield: 78.87%). $^1$H NMR (400 MHz, $CDCl_3$) δ: 5.01-4.96 (m, 1H), 4.90 (br s, 2H), 3.58-3.66 (m, 2H), 3.41-3.47 (m, 2H), 3.34 (d, J=4.5 Hz, 2H), 1.55-1.68 (m, 2H), 0.90-0.96 (m, 3H).

Step 3: Synthesis of Compound BB-6-3

At room temperature, the compound BB-6-2 (5.00 g, 27.44 mmol) and potassium tert-butoxide (9.24 g, 82.32 mmol) were added to dimethyl sulfoxide (50.00 mL), and the reaction mixture was heated to 35° C. and stirred for 0.5 hour, then 5-bromo-4,6-dichloropyrimidine (6.25 g, 27.44 mmol) was added to reaction solution, and the reaction mixture was further stirred at 35° C. for 12 hours. After the reaction was completed, hydrochloric acid (0.5 M, 50 mL) was added, and the mixture was extracted with ethyl acetate (50 mL×3). The organic phases were combined, washed with saturated brine (100 mL×2), dried over anhydrous sodium sulfate, filtered, and the solvent of filtrate was removed under reduced pressure. The residue was separated by column chromatography (eluent: petroleum ether/ethyl acetate=10/1-3/1, volume ratio) to obtain the target compound BB-6-3 (light yellow solid, 2.00 g, yield: 18.15%). MS-ESI m/z: 372.8 [M+H]$^+$, 374.8 [M+H+2]$^+$. $^1$H NMR (400 MHz, $CDCl_3$) δ: 8.48 (s, 1H), 7.77 (s, 1H), 5.96 (t, J=5.6 Hz, 1H), 3.43-3.47 (m, 2H), 3.24 (t, J=6.6 Hz, 2H), 3.18 (d, J=4.7 Hz, 2H), 1.43 (d, J=7.2 Hz, 2H), 0.81 (t, J=7.4 Hz, 3H).

Step 4: Synthesis of Compound BB-6

At room temperature, potassium tert-butoxide (1.80 g, 16.06 mmol) was added to ethylene glycol (33.30 g, 536.49 mmol, 30.00 mL), the reaction mixture was heated to 40° C. and stirred for 0.5 hour under nitrogen atmosphere, then a solution of the compound BB-6-3 (2.00 g, 5.35 mmol) in ethylene glycol dimethyl ether (20.00 mL) was added to solution, and the reaction mixture was heated to 110° C. and stirred for 12 hours under nitrogen atmosphere. After the reaction was completed, the mixture was cooled to room temperature, hydrochloric acid (0.5 M, 30 mL) was added, and the mixture was extracted with ethyl acetate (50 mL×3). The organic phases were combined, washed with saturated brine (100 mL×2), dried over anhydrous sodium sulfate, filtered, and the solvent of filtrate was removed under reduced pressure. The residue was separated by column chromatography (eluent: petroleum ether/ethyl acetate=10/1-1/1, volume ratio) to obtain the target compound BB-6

(light yellow solid, 1.20 g, yield: 56.18%). $^1$H NMR (400 MHz, CDCl$_3$) δ: 8.39 (s, 1H), 7.67 (s, 1H), 6.08 (t, J=5.7 Hz, 1H), 4.56-4.65 (m, 2H), 3.97-4.03 (m, 2H), 3.52-3.57 (m, 2H), 3.33 (t, J=6.6 Hz, 2H), 3.24 (q, J=5.5 Hz, 2H), 2.44 (br s, 1H), 1.44-1.59 (m, 2H), 0.90 (t, J=7.4 Hz, 3H).

Reference Embodiment 7: Fragment BB-7

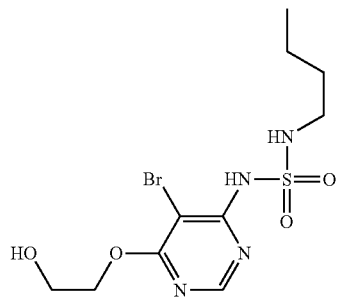 [SMILES: CCCCNS(=O)(=O)Nc1ncnc(OCCO)c1Br]

Synthetic Route:

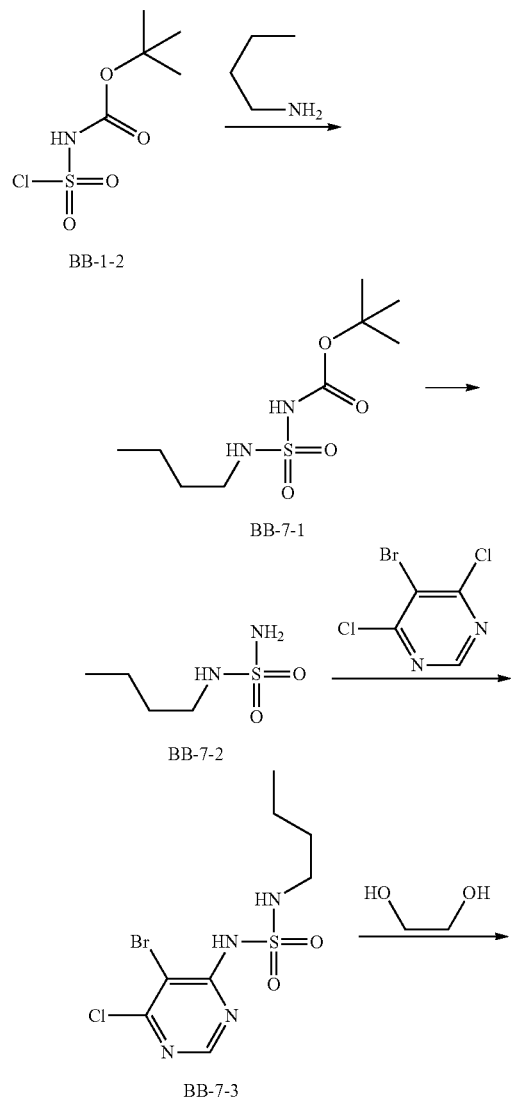

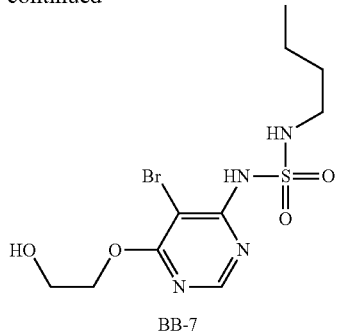

BB-7

Step 1: Synthesis of Compound BB-7-1

At room temperature, n-butylamine (2.83 g, 38.64 mmol, 3.82 mL) and triethylamine (3.91 g, 38.64 mmol, 5.36 mL) were dissolved in dichloromethane (100 mL), and the reaction mixture was cooled to 0° C., then a solution of the compound BB-1-2 (46.37 mmol, crude product) in dichloromethane was slowly added dropwise to reaction solution (dropping time was about 0.5 hour), and the reaction mixture was warmed to room temperature and stirred for 16 hours. After the reaction was completed, the solvent was removed under reduced pressure. The residue was added with dichloromethane (200 mL), and washed with 1 M diluted hydrochloric acid (80 mL) and water (100 mL×2), respectively. The organic phase was dried over anhydrous sodium sulfate, filtered, and the solvent was removed under reduced pressure to obtain the target compound BB-7-1 (white solid, 3.00 g, yield: 30.77%). 1H NMR (400 MHz, CDCl$_3$) δ: 2.98 (q, J=8.0 Hz, 2H), 1.47 (t, J=4.0 Hz 2H), 1.24-1.38 (m, 11H), 0.86 (t, J=4.0 Hz, 3H).

Step 2: Synthesis of Compound BB-7-2

At room temperature, the compound BB-7-1 (3.00 g, 11.89 mmol) was added to water (150.00 mL), and the reaction mixture was heated to 110° C. and stirred for 0.5 hour. After the reaction was completed, the mixture was cooled to room temperature and extracted with dichloromethane (50 mL). The organic phase was discarded, and the aqueous phase was extracted with ethyl acetate (100 mL×3). Then the organic phases were combined, dried over anhydrous sodium sulfate, filtered, and the solvent was removed under reduced pressure to obtain the target compound BB-7-2 (colorless oil, 1.10 g, yield: 60.78%). $^1$H NMR (400 MHz, CDCl$_3$) δ: 3.06 (q, J=8.0 Hz, 2H), 1.46-1.54 (m, 2H), 1.32 (s, 2H), 0.87 (t, J=8.0 Hz, 3H).

Step 3: Synthesis of Compound BB-7-3

At room temperature, the compound BB-7-2 (1.10 g, 7.23 mmol) was dissolved in dimethyl sulfoxide (50.00 mL), then potassium tert-butoxide (1.22 g, 10.85 mmol) was added, the reaction mixture was stirred at room temperature for 0.5 hour under nitrogen atmosphere. Then, 5-bromo-4,6-dichloropyrimidine (1.98 g, 8.68 mmol) was added to reaction solution, and the reaction mixture was further stirred for 3 hours at room temperature under nitrogen protection. After the reaction was completed, saturated brine (50 mL) was added, the pH was adjusted to 4-5 with 10% dilute hydrochloric acid, and the mixture was extracted with ethyl acetate (80 mL). The organic phases were combined, washed with water (50 mL×2), dried over anhydrous sodium sulfate, filtered, and the solvent of filtrate was removed under reduced pressure. The residue was separated by column chromatography (eluent: petroleum ether/ethyl acetate=10/1-1/1, volume ratio) to obtain the target compound BB-7-3 (white solid, 350.00 mg, yield: 9.58%). MS-ESI m/z: 342.7

[M+H]+, 344.7 [M+H+2]+. ¹H NMR (400 MHz, CDCl₃) δ: 8.49 (s, 1H), 7.74 (s, 1H), 5.41 (t, J=6.0 Hz, 1H), 3.00 (q, J=7.2 Hz, 2H), 1.47 (q, J=7.6 Hz, 2H), 1.28-1.32 (m, 2H), 0.84 (t, J=7.2 Hz, 3H).

Step 4: Synthesis of Compound BB-7

At room temperature, potassium tert-butoxide (343.36 mg, 3.06 mmol) was added to ethylene glycol (3.17 g, 51.00 mmol, 2.85 mL), the reaction mixture was heated to 40° C. and stirred for 0.5 hour under nitrogen atmosphere, then a solution of compound BB-7-3 (350.00 mg, 1.02 mmol) in ethylene glycol dimethyl ether (20.00 mL) was added to solution in one portion, and the reaction mixture was heated to 110° C. and stirred for 15 hours under nitrogen atmosphere. After the reaction was completed, the mixture was cooled to room temperature, added with ice water (50 mL), adjusted to pH of 4 with 1M dilute hydrochloric acid, and extracted with ethyl acetate (20 mL×3). The organic phases were combined, washed with saturated brine (50 mL), dried over anhydrous sodium sulfate, filtered, and the solvent of filtrate was removed under reduced pressure. The residue was separated by preparative chromatography (eluent: dichloromethane/methanol=20/1, volume ratio) to obtain the target compound BB-7 (yellow solid, 300.00 mg, yield: 79.66%). ¹H NMR (400 MHz, CDCl₃) δ: 8.30 (s, 1H), 7.54 (s, 1H), 5.44 (t, J=6.0 Hz, 1H), 4.52 (t, J=4.8 Hz, 2H), 3.92 (q, J=3.2 Hz, 2H), 2.98 (q, J=6.8 Hz, 2H), 2.31 (t, J=6.0 Hz, 1H), 1.45 (q, J=8.0 Hz, 2H), 1.26-1.32 (m, 2H), 0.83 (t, J=7.2 Hz, 3H).

Reference Embodiment 8: Fragment BB-8

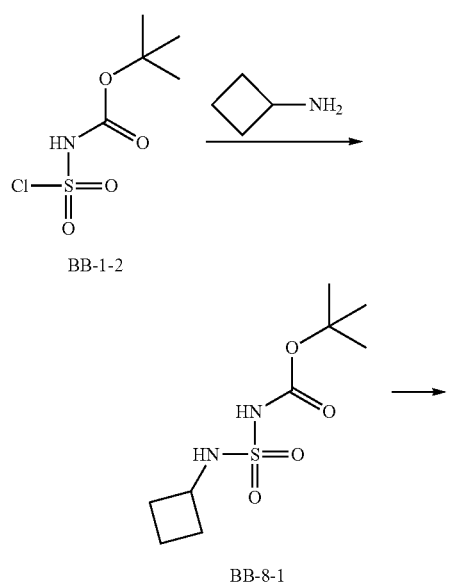

Synthetic Route:

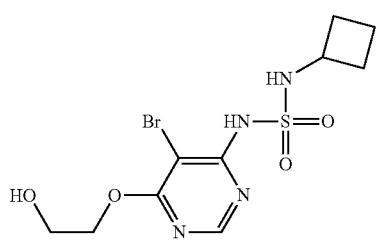 [SMILES: O=S(=O)(Nc1ncnc(OCCO)c1Br)NC1CCC1]

BB-1-2

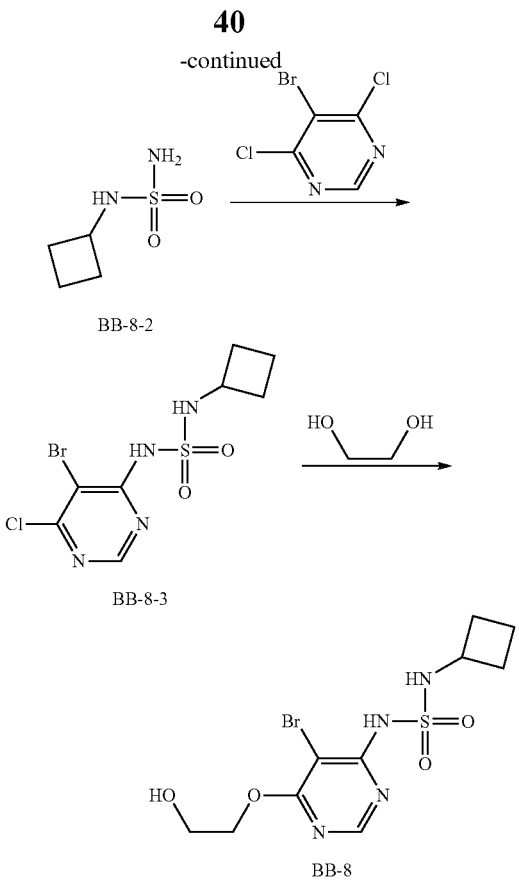

Step 1: Synthesis of Compound BB-8-1

At room temperature, cyclobutylamine (5.00 g, 70.30 mmol, 6.02 mL) and triethylamine (8.54 g, 84.36 mmol, 11.70 mL) were dissolved in dichloromethane (100.00 mL), and the reaction mixture was cooled to 0° C., then a solution of the compound BB-1-2 (84.36 mmol, crude product) in dichloromethane was added dropwise to reaction solution (dropping time was about 0.5 hour), and the reaction mixture was warmed to room temperature and stirred for 15 hours. After the reaction was completed, the mixture was extracted with water (100 mL×3). The aqueous phases were combined, adjusted to pH of 5 with 1 M dilute hydrochloric acid, and extracted with ethyl acetate (100 mL×3). The organic phases were combined, washed with saturated brine (100 mL), dried over anhydrous sodium sulfate, filtered, and the solvent of filtrate was removed under reduced pressure to obtain the target compound BB-8-1 (white solid, 12.00 g, yield: 68.19%). ¹H NMR (400 MHz, CDCl₃) δ: 5.35 (d, J=9.8 Hz, 1H), 3.94-3.84 (m, 1H), 3.15 (d, J=7.3 Hz, 1H), 2.38-2.30 (m, 2H), 2.03-1.90 (m, 2H), 1.77-1.61 (m, 2H), 1.50 (s, 9H).

Step 2: Synthesis of Compound BB-8-2

At room temperature, the compound BB-8-1 (5.00 g, 19.98 mmol) was added to water (100.00 mL), and the reaction mixture was heated to 100° C. and stirred for 1 hour. After the reaction was completed, the mixture was cooled to room temperature and extracted with ethyl acetate (100 mL×3). The organic phases were combined, washed with saturated brine (100 mL), dried over anhydrous sodium sulfate, filtered, and the solvent of filtrate was removed under reduced pressure to obtain the target compound BB-8-2 (white solid, 2.90 g, yield: 96.63%). ¹H NMR (400 MHz, CDCl₃) δ: 4.72-4.48 (m, 2H), 4.07-3.81 (m, 1H), 2.47-2.25 (m, 2H), 2.04-1.90 (m, 2H), 1.83-1.65 (m, 2H).

Step 3: Synthesis of Compound BB-8-3

At room temperature, the compound BB-8-2 (2.90 g, 19.31 mmol) and potassium tert-butoxide (4.33 g, 38.62 mmol) were added to dimethyl sulfoxide (80.00 mL), and the reaction mixture was stirred at room temperature for 0.5 hour, then 5-bromo-4,6-dichloropyrimidine (3.52 g, 15.45 mmol) was added to reaction solution, and the reaction mixture was further stirred at room temperature for 15 hours. After the reaction was completed, water (150 mL) was added, the pH was adjusted to 6 with 1M dilute hydrochloric acid, and the mixture was extracted with ethyl acetate (200 mL×3). The organic phases were combined, washed with saturated brine (200 mL), dried over anhydrous sodium sulfate, filtered, and the solvent of filtrate was removed under reduced pressure. The residue was separated by column chromatography (eluent: petroleum ether/ethyl acetate=10/1-3/1, volume ratio) to obtain the target compound BB-8-3 (yellow solid, 2.50 g, yield: 37.90%). $^1$H NMR (400 MHz, CDCl$_3$) δ: 8.59 (s, 1H), 7.82 (s, 1H), 5.71 (d, J=8.5 Hz, 1H), 4.10-3.74 (m, 1H), 2.30-2.17 (m, 2H), 1.94-1.79 (m, 2H), 1.74-1.58 (m, 2H).

Step 4: Synthesis of Compound BB-8

At room temperature, potassium tert-butoxide (2.46 g, 21.96 mmol) was added to ethylene glycol (22.20 g, 357.66 mmol, 20.00 mL), the reaction mixture was heated to 40° C. and stirred for 0.5 hour under nitrogen atmosphere, then a solution of the compound BB-8-3 (2.50 g, 7.32 mmol) in ethylene glycol dimethyl ether (80.00 mL) was added to solution, and the reaction mixture was heated to 110° C. and stirred for 15 hours under nitrogen atmosphere. After the reaction was completed, the mixture was cooled to room temperature, added with water (200 mL), adjusted to pH of 4 with 1 M dilute hydrochloric acid, and extracted with ethyl acetate (200 mL×3). The organic phases were combined, washed with saturated brine (200 mL), dried over anhydrous sodium sulfate, filtered, and the solvent of filtrate was removed under reduced pressure. The residue was separated by column chromatography (eluent: petroleum ether/ethyl acetate=5/1-1/1, volume ratio) to obtain the target compound BB-8 (yellow solid, 1.1 g, yield: 40.92%). $^1$H NMR (400 MHz, CDCl$_3$) δ: 8.41 (s, 1H), 7.62 (s, 1H), 5.72 (br d, J=8.8 Hz, 1H), 4.81-4.42 (m, 2H), 4.03-3.96 (m, 2H), 3.96-3.87 (m, 1H), 2.31-2.16 (m, 2H), 1.93-1.79 (m, 2H), 1.73-1.61 (m, 2H).

Reference Embodiment 9: Fragment BB-9

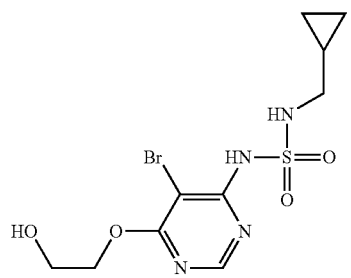 [SMILES: O=S(=O)(NCC1CC1)Nc1ncnc(OCCO)c1Br]

Synthetic Route:

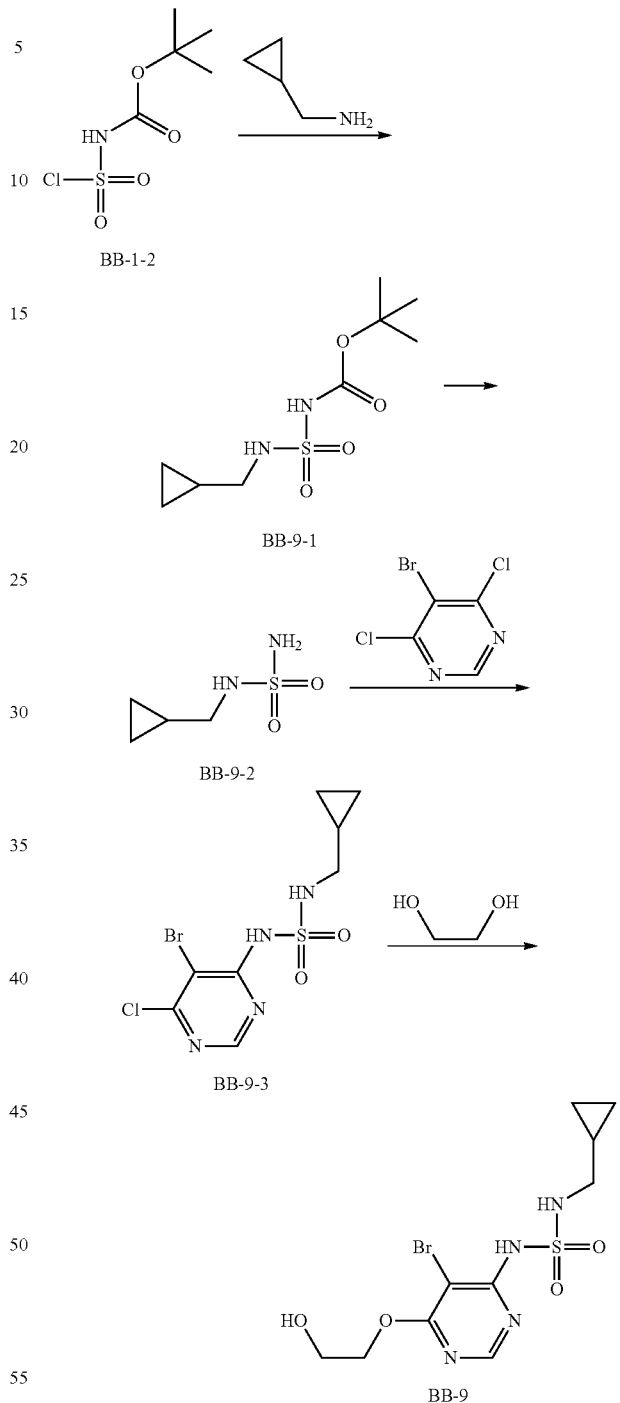

Step 1: Synthesis of Compound BB-9-1

At room temperature, cyclopropylmethylamine (5.00 g, 70.30 mmol) and triethylamine (14.23 g, 140.60 mmol, 19.49 mL) were dissolved in dichloromethane (100.00 mL), the reaction mixture was cooled to 0° C., and then a solution of the compound BB-1-2 (70.30 mmol, crude product) in dichloromethane was added (dropping time about 0.5 hour), the reaction mixture was warmed to room temperature and stirred for 15 hours under nitrogen atmosphere. After the reaction was completed, the solvent was removed under reduced pressure, and the residue was added with water (100 mL), adjusted to pH of 5 with 1 M dilute hydrochloric acid, and extracted with ethyl acetate (100 mL×3). The organic phases were combined, washed with saturated brine (100 mL), dried over anhydrous sodium sulfate, filtered, and the solvent of filtrate was removed under reduced pressure to obtain the target compound BB-9-1 (white solid, 11.00 g, yield: 62.51%). $^1$H NMR (400 Mhz, CDCl$_3$) δ: 2.94 (dd, J=4.0, 6.8 Hz, 2H), 1.53-1.44 (m, 9H), 1.11-0.94 (m, 1H), 0.64-0.52 (m, 2H), 0.30-0.12 (m, 2H).

Step 2: Synthesis of Compound BB-9-2

At room temperature, the compound BB-9-1 (10.00 g, 39.95 mmol) was added to water (100.00 mL), and the reaction mixture was heated to 100° C. and stirred for 1 hour. After the reaction was completed, the mixture was cooled to room temperature and extracted with ethyl acetate (100 mL×3). The organic phases were combined, washed with saturated brine (100 mL), dried over anhydrous sodium sulfate, filtered, and the solvent of filtrate was removed under reduced pressure to obtain the target compound BB-9-2 (white solid, 5.00 g, yield: 83.33%). $^1$H NMR (400 MHz, CDCl$_3$) δ: 4.64-4.54 (m, 2H), 3.64 (br s, 1H), 3.03-2.86 (m, 2H), 1.16-0.98 (m, 1H), 0.63-0.42 (m, 2H), 0.29-0.10 (m, 2H).

Step 3: Synthesis of Compound BB-9-3

At room temperature, the compound BB-9-2 (4.94 g, 32.91 mmol) and potassium tert-butoxide (4.92 g, 43.88 mmol) were added to dimethyl sulfoxide (80.00 mL), the reaction mixture was stirred at room temperature for 0.5 hour under nitrogen atmosphere, then 5-bromo-4,6-dichloropyrimidine (5.00 g, 21.94 mmol) was added, and the reaction mixture was stirred at room temperature for 15 hours under nitrogen atmosphere. After the reaction was completed, water (100 mL) was added, the pH was adjusted to 6 with 1 M dilute hydrochloric acid, and the mixture was extracted with ethyl acetate (200 ml×3). The organic phases were combined, washed with saturated brine (200 mL), dried over anhydrous sodium sulfate, filtered, and the solvent of filtrate was removed under reduced pressure. The residue was separated by column chromatography (eluent: petroleum ether/ethyl acetate=10/1-3/1, volume ratio) to obtain the target compound BB-9-3 (white solid, 5.00 g, yield: 66.71%). $^1$H NMR (400 MHz, CDCl$_3$) δ: 8.57 (s, 1H), 7.80 (br s, 1H), 5.63 (t, J=5.4 Hz, 1H), 2.96 (t, J=6.7 Hz, 2H), 1.09-0.86 (m, 1H), 0.62-0.39 (m, 2H), 0.26-0.03 (m, 2H).

Step 4: Synthesis of Compound BB-9

At room temperature, potassium tert-butoxide (4.93 g, 43.91 mmol) was added to ethylene glycol (22.20 g, 357.66 mmol, 20.00 mL), the reaction mixture was heated to 40° C. and stirred for 0.5 hour, and then a solution of the compound BB-9-3 (5.00 g, 14.64 mmol) in ethylene glycol dimethyl ether (80.00 mL) was added to mixture, and the reaction mixture was heated to 110° C. and stirred for 15 hours. After the reaction was completed, the mixture was cooled to room temperature, added with water (200 mL), adjusted the pH to 3 with 1 M dilute hydrochloric acid, and extracted with ethyl acetate (200 mL×3). The organic phases were combined, washed with saturated brine (50 mL), dried over anhydrous sodium sulfate, filtered, and the solvent of filtrate was removed under reduced pressure. The residue was separated by column chromatography (eluent: petroleum ether/ethyl acetate=5/1-1/1, volume ratio) to obtain the target compound BB-9 (yellow oil, 3.50 g, yield: 65.10%). $^1$H NMR (400 MHz, CDCl$_3$): 8.45-8.29 (m, 1H), 7.68 (br s, 1H), 5.74 (t, J=5.5 Hz, 1H), 4.73-4.52 (m, 2H), 4.04-3.93 (m, 2H), 2.93 (t, J=6.5 Hz, 2H), 2.04 (s, 1H), 1.11-0.78 (m, 1H), 0.62-0.41 (m, 2H), 0.14 (q, J=5.0 Hz, 2H).

Reference Embodiment 10: Fragment BB-10

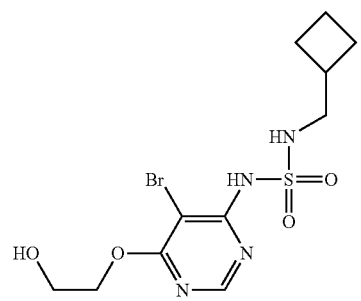 [SMILES: O=S(=O)(NCC1CCC1)Nc1ncnc(OCCO)c1Br]

Synthetic Route:

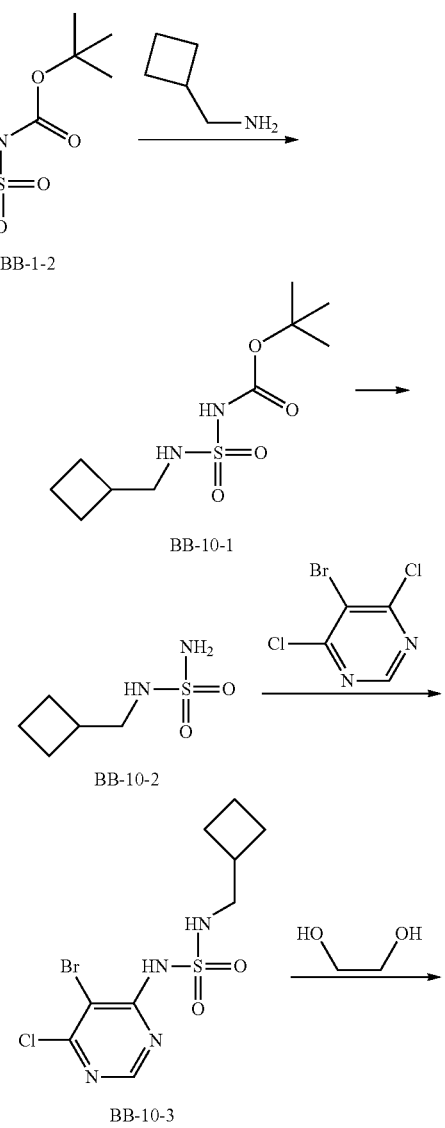

Step 4: Synthesis of Compound BB-10

At room temperature, potassium tert-butoxide (1.89 g, 16.88 mmol) was added to ethylene glycol (15.79 g, 254.55 mmol, 14.23 mL), the reaction mixture was heated to 40° C. and stirred for 0.5 hour under nitrogen atmosphere, then a solution of the compound BB-10-3 (3.00 g, 8.44 mmol) in ethylene glycol dimethyl ether (30.00 mL) was added to mixture, and the reaction mixture was heated to 120° C. and stirred for 15 hours under nitrogen atmosphere. After the reaction was completed, water (60 mL) was added, the pH was adjusted to 4 with 1 M dilute hydrochloric acid, and mixture was extracted with ethyl acetate (50 mL×3). The organic phases were combined, washed with saturated brine (30 mL), dried over anhydrous sodium sulfate, filtered, and the solvent of filtrate was removed under reduced pressure. The residue was separated by column chromatography (eluent: petroleum ether/ethyl acetate=1/2, volume ratio) to obtain the target compound BB-10 (yellow oil, 2.50 g, yield: 77.73%). $^1$H NMR (400 MHz, CDCl$_3$) δ: 8.39 (s, 1H), 7.65 (br s, 1H), 5.52 (t, J=6.0 Hz, 1H), 4.71-4.49 (m, 2H), 4.02 (br d, J=3.8 Hz, 2H), 3.12-3.01 (m, 2H), 2.60-2.47 (m, 1H), 2.43 (br s, 1H), 2.09-2.01 (m, 2H), 1.98-1.77 (m, 2H), 1.74-1.64 (m, 2H).

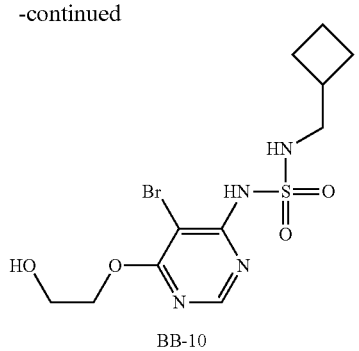

BB-10

Step 1: Synthesis of Compound BB-10-1

At 0° C., cyclobutylmethylamine hydrochloride (5.00 g, 41.12 mmol), triethylamine (10.40 g, 102.80 mmol, 14.25 mL) and dichloromethane (50.00 mL) were added to a solution of the compound BB-1-2 (41.12 mmol, crude product) in dichloromethane, and the reaction mixture was warmed to room temperature and stirred for 18 hours under nitrogen atmosphere. After the reaction was completed, water (60 mL) was added, and the mixture was extracted with dichloromethane (60 mL×2). The organic phases were combined, washed with 1M dilute hydrochloric acid (50 mL) and saturated brine (100 mL), dried over anhydrous sodium sulfate, filtered, and the solvent of filtrate was removed under reduced pressure to obtain the target compound BB-10-1 (yellow solid, 7.20 g, yield: 66.24%).

Step 2: Synthesis of Compound BB-10-2

At room temperature, the compound BB-10-1 (7.00 g, 26.48 mmol) was added to water (100.00 mL), and the reaction mixture was heated to 110° C. and stirred for 2 hours. After the reaction was completed, the mixture was cooled to room temperature and extracted with ethyl acetate (100 mL×3). The organic phases were combined, washed with saturated brine (200 mL), dried over anhydrous sodium sulfate, filtered, and the solvent of filtrate was removed under reduced pressure to obtain the target compound BB-10-2 (colorless oil, 3.80 g, yield: 87.38%). $^1$H NMR (400 MHz, CDCl$_3$) δ: 5.10-4.92 (m, 2H), 3.15-3.10 (m, 2H), 2.54-2.50 (m, 1H), 2.07-2.04 (m, 2H), 1.90-1.88 (m, 2H), 1.88-1.69 (m, 2H).

Step 3: Synthesis of Compound BB-10-3

At room temperature, potassium tert-butoxide (3.14 g, 28.00 mmol) was added to a solution of compound BB-10-2 (2.30 g, 14.00 mmol) in dimethyl sulfoxide (40.00 mL), the reaction mixture was stirred at room temperature for 0.5 hour under nitrogen atmosphere, then 5-bromo-4,6-dichloropyrimidine (3.19 g, 14.00 mmol) was added, and the reaction mixture was stirred at room temperature for 15 hours under nitrogen atmosphere. After the reaction was completed, water (80 mL) was added, the pH was adjusted to 4 with 1 M dilute hydrochloric acid, and the mixture was extracted with ethyl acetate (40 mL×3). The organic phases were combined, washed with saturated brine (40 mL), dried over anhydrous sodium sulfate, filtered, and the solvent was removed under reduced pressure. The residue was separated by column chromatography (eluent: petroleum ether/ethyl acetate=1/1, volume ratio) to obtain the target compound BB-10-3 (yellow solid, 3.10 g, yield: 62.29%). $^1$H NMR (400 MHz, CDCl$_3$) δ: 8.49 (s, 1H), 7.79 (s, 1H), 5.45 (t, J=6.0 Hz, 1H), 3.03-2.98 (m, 2H), 2.53-2.33 (m, 1H), 2.04-1.98 (m, 2H), 1.84-1.78 (m, 2H), 1.63-1.57 (m, 2H).

Reference Embodiment 11: Fragment BB-11

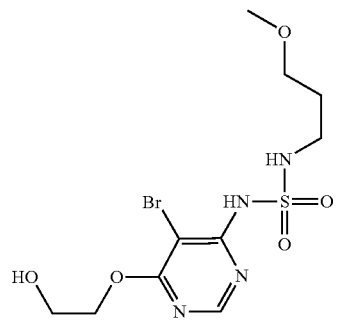 [SMILES: COCCCNS(=O)(=O)Nc1ncnc(OCCO)c1Br]

Synthetic Route:

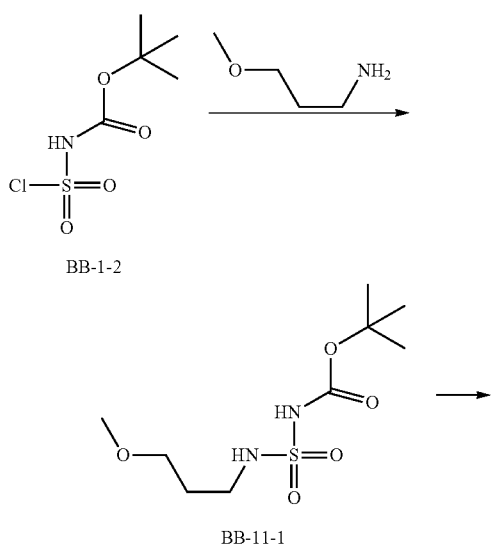

BB-1-2

BB-11-1

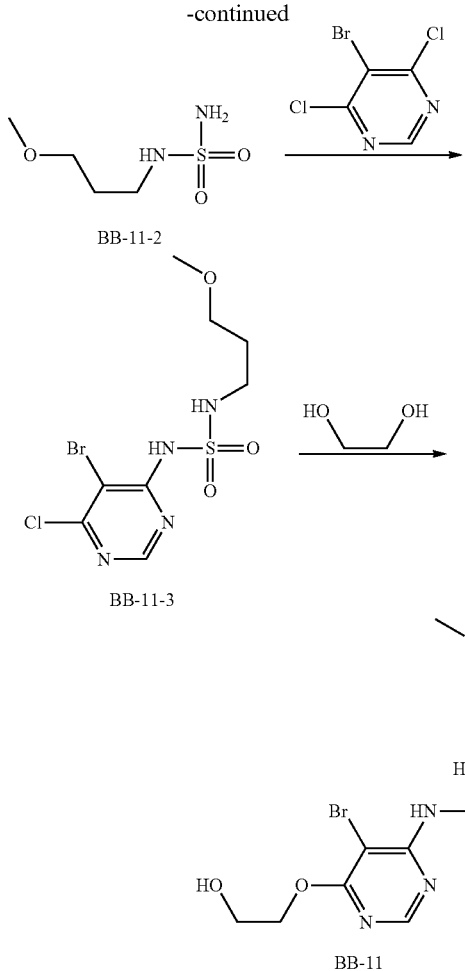

Step 1: Synthesis of Compound BB-11-1

At 0° C., a solution of the compound BB-1-2 (78.00 mmol, crude product) in dichloromethane was slowly added dropwise to a solution of 3-methoxypropylamine (6.95 g, 78.00 mmol, 7.99 mL) and triethylamine (15.79 g, 156.00 mmol, 21.63 mL) in dichloromethane (50.00 mL) (dropping time was about 0.5 hour), and the reaction mixture was warmed to room temperature and stirred for 18 hours. After the reaction was completed, water (200 mL) was added, and the mixture was extracted with dichloromethane (150 mL×2). The organic phases were combined, washed with 1 M dilute hydrochloric acid (50 mL) and saturated brine (200 mL) respectively, dried over anhydrous sodium sulfate, filtered, and the solvent of filtrate was removed under reduced pressure to obtain the target compound BB-11-1 (white solid, 16.00 g, yield: 76.45%). $^1$H NMR (400 MHz, CDCl$_3$) δ: 3.42 (t, J=5.8 Hz, 2H), 3.28 (s, 3H), 3.15-3.04 (m, 2H), 1.91-1.64 (m, 2H), 1.43 (s, 9H).

Step 2: Synthesis of Compound BB-11-2

At room temperature, the compound BB-11-1 (16.00 g, 59.63 mmol) was added to water (100.00 mL), and the reaction mixture was heated to 100° C. and stirred for 1 hour. After the reaction was completed, the mixture was cooled to room temperature and extracted with ethyl acetate (100 mL×3). The organic phases were combined, washed with saturated brine (100 mL), dried over anhydrous sodium sulfate, filtered, and the solvent of filtrate was removed under reduced pressure to obtain the target compound BB-11-2 (colorless oil, 8.50 g, yield: 84.74%). $^1$H NMR (400 MHz, DMSO_d$_6$) δ: 6.49-6.38 (m, 3H), 3.37-3.32 (m, 2H), 3.23-3.19 (m, 3H), 2.96-2.82 (m, 2H), 1.73-1.63 (m, 2H).

Step 3: Synthesis of Compound BB-11-3

At room temperature, potassium tert-butoxide (2.67 g, 23.78 mmol) was added to a solution of compound BB-11-2 (2.00 g, 11.89 mmol) in dimethyl sulfoxide (10.00 mL), the reaction mixture was stirred at room temperature for 0.5 hour under nitrogen atmosphere, then 5-bromo-4,6-dichloropyrimidine (2.71 g, 11.89 mmol) was added, and the reaction mixture was stirred at room temperature for 15 hours under nitrogen atmosphere. After the reaction was completed, water (60 mL) was added, the pH was adjusted to 4 with 0.5 M diluted hydrochloric acid, and the mixture was extracted with ethyl acetate (30 mL×3). The organic phases were combined, washed with saturated brine (30 mL), dried over anhydrous sodium sulfate, filtered, and the solvent of filtrate was removed under reduced pressure. The residue was separated by column chromatography (eluent: petroleum ether/ethyl acetate=1/1, volume ratio) to obtain the target compound BB-11-3 (white solid, 3.30 g, yield: 77.21%). $^1$H NMR (400 MHz, DMSO_d$_6$) δ: 8.59 (s, 1H), 3.29-3.25 (m, 2H), 3.16 (s, 3H), 2.96 (t, J=6.9 Hz, 2H), 1.70-1.62 (m, 2H).

Step 4: Synthesis of Compound BB-11

At room temperature, potassium tert-butoxide (2.06 g, 18.35 mmol) was added to ethylene glycol (30.24 g, 487.25 mmol, 27.25 mL), the reaction mixture was heated to 40° C. and stirred for 0.5 hour under nitrogen atmosphere, then a solution of the compound BB-11-3 (3.30 g, 9.18 mmol) in ethylene glycol dimethyl ether (10.00 mL) was added to mixture, and the reaction mixture was heated to 110° C. and stirred for 24 hours under nitrogen atmosphere. After the reaction was completed, the mixture was cooled to room temperature, added with water (60 mL), adjusted the pH to 4 with 1 M dilute hydrochloric acid, and extracted with ethyl acetate (30 mL×3). The organic phases were combined, washed with saturated brine (30 mL), dried over anhydrous sodium sulfate, filtered, and the solvent of filtrate was removed under reduced pressure. The residue was separated by column chromatography (eluent: petroleum ether/ethyl acetate=1/2, volume ratio) to obtain the target compound BB-11 (yellow oil, 2.20 g, yield: 61.34%). $^1$H NMR (400 Mhz, CDCl$_3$) δ: 8.51-8.08 (m, 1H), 7.65 (s, 1H), 6.10 (t, J=5.9 Hz, 1H), 4.67-4.45 (m, 2H), 4.01 (d, J=3.8 Hz, 2H), 3.53-3.39 (m, 2H), 3.34 (s, 3H), 3.26-3.13 (m, 2H), 2.46 (br s, 1H), 1.85 (q, J=6.0 Hz, 2H).

Reference Embodiment 12: Fragment BB-12

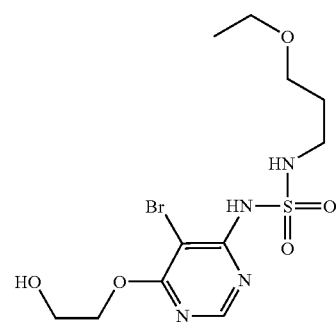 [SMILES: CCOCCCNS(=O)(=O)Nc1ncnc(OCCO)c1Br]

Synthetic Route:

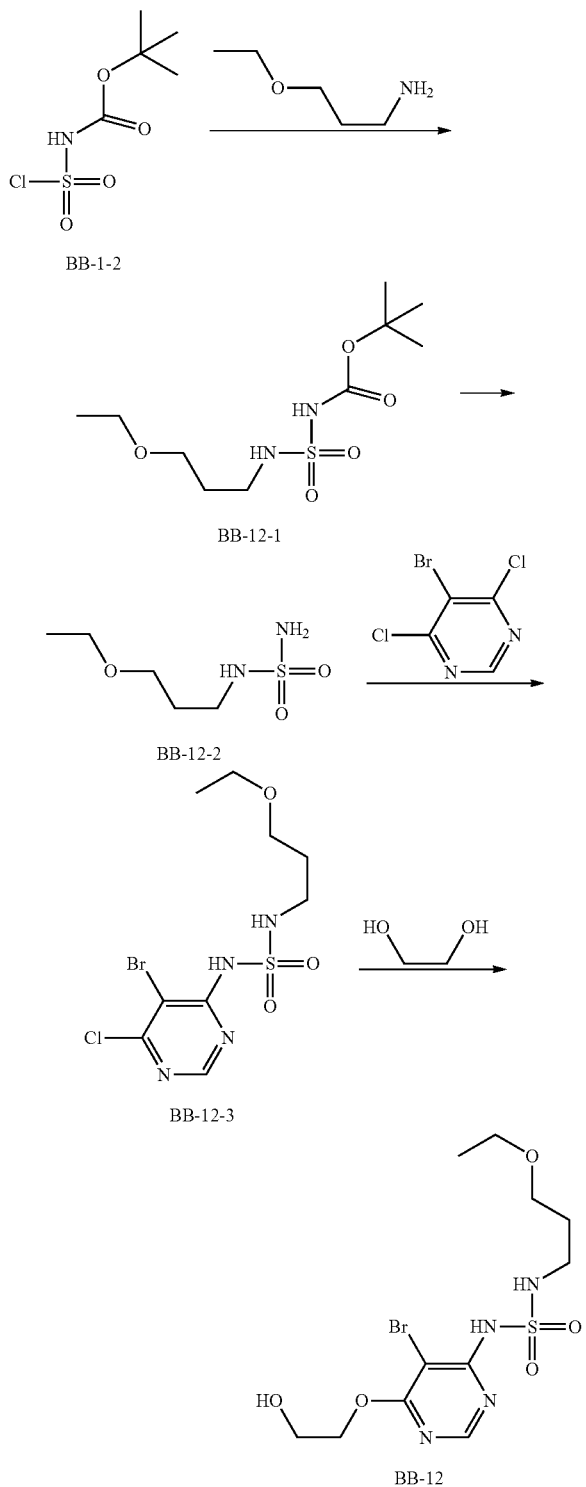

Step 1: Synthesis of Compound BB-12-1

At 0° C., a solution of the compound BB-1-2 (74.19 mmol, crude product) in dichloromethane was slowly added to a solution of 3-ethoxypropyl-1-amine (7.65 g, 74.19 mmol, 8.90 mL) and triethylamine (22.52 g, 222.58 mmol, 30.85 mL) in dichloromethane (40.00 mL) (dropping time was about 1 hour), and the reaction mixture was warmed to room temperature and stirred for 14 hours under nitrogen atmosphere. After the reaction was completed, the solvent was removed under reduced pressure, and the residue was added with water (200 mL) and extracted with dichloromethane (100 mL). The organic phase was discarded, and the aqueous phase was adjusted to pH of 5-6 with 1 M diluted hydrochloric acid, then the aqueous phase was extracted with ethyl acetate (100 mL×3). The organic phases were combined, dried over anhydrous sodium sulfate, filtered, and the solvent of filtrate was removed under reduced pressure to obtain the target compound BB-12-1 (yellow solid, 17.00 g, crude product). $^1$H NMR (400 MHz, DMSO_$d_6$) δ: 10.80 (s, 1H), 7.51 (t, J=5.8 Hz, 1H), 3.40-3.37 (m, 2H), 2.93 (q, J=6.4 Hz, 2H), 2.51 (s, 2H), 1.74-1.61 (m, 2H), 1.43 (s, 9H), 1.10 (t, J=6.8 Hz, 3H).

Step 2: Synthesis of Compound BB-12-2

At room temperature, the compound BB-12-1 (17.00 g, 60.21 mmol) was added to water (100.00 mL), and the reaction mixture was heated to 110° C. and stirred for 1 hour. After the reaction was completed, the mixture was cooled to room temperature and extracted with ethyl acetate (100 mL×3). The organic phases were combined, washed with saturated brine (100 mL), dried over anhydrous sodium sulfate, and filtered, and the solvent of filtrate was removed under reduced pressure to obtain the target compound BB-12-2 (yellow oil, 9.00 g, crude product). $^1$H NMR (400 MHz, DMSO_$d_6$) δ: 6.46 (s, 2H), 6.41 (t, J=6.2 Hz, 1H), 3.43-3.37 (m, 4H), 2.90 (q, J=6.4 Hz, 2H), 1.75-1.60 (m, 2H), 1.10 (t, J=7.0 Hz, 3H).

Step 3: Synthesis of Compound BB-12-3

At room temperature, the compound BB-12-2 (1.60 g, 8.78 mmol) and potassium tert-butoxide (1.97 g, 17.55 mmol) were added to dimethyl sulfoxide (20.00 mL), the reaction mixture was stirred at room temperature for 1 hour under nitrogen atmosphere, 5-bromo-4,6-dichloropyrimidine (2.00 g, 8.78 mmol) was added, and the reaction mixture was stirred at room temperature for 11 hours under nitrogen atmosphere. After the reaction was completed, water (100 mL) was added, the pH was adjusted to 5-6 with 1 M diluted hydrochloric acid, and the mixture was extracted with ethyl acetate (50 mL×3). The organic phases were combined, washed with water (50 mL×2), dried over anhydrous sodium sulfate, filtered, and the solvent of filtrate was removed under reduced pressure. The residue was separated by column chromatography (eluent: petroleum ether/ethyl acetate=10/1-4/1, volume ratio) to obtain the target compound BB-12-3 (yellow solid, 1.30 g, yield: 39.64%). $^1$H NMR (400 MHz, DMSO_$d_6$) δ: 8.59 (s, 1H), 3.34-3.29 (m, 4H), 2.98 (t, J=6.8 Hz, 2H), 1.69-1.61 (m, 2H), 1.06 (t, J=6.8 Hz, 3H).

Step 4: Synthesis of Compound BB-12

At room temperature, potassium tert-butoxide (1.17 g, 10.44 mmol) was added to a mixture solution of ethylene glycol (35.63 g, 574.20 mmol, 32.10 mL) and ethylene glycol dimethyl ether (10.00 mL), the reaction mixture was heated to 40° C. and stirred for 0.5 hours under nitrogen atmosphere, then a solution of the compound BB-12-3 (1.30 g, 3.48 mmol) in ethylene glycol dimethyl ether (20.00 mL) was added to mixture in one portion, and the reaction mixture was heated to 100° C. and stirred for 15 hours under nitrogen atmosphere. After the reaction was completed, the mixture was cooled to room temperature, added with water (100 mL), adjusted to pH of 5-6 with 2 M dilute hydrochloric acid, and extracted with ethyl acetate (60 mL×3). The organic phases were combined, dried over anhydrous sodium sulfate, filtered, and the solvent of filtrate was removed under reduced pressure. The residue was separated by column chromatography (eluent: petroleum ether/ethyl acetate=3/1-1/3, volume ratio) to obtain the target compound BB-12 (white solid, 1.10 g, yield: 79.17%). MS-ESI m/z: 398.9 [M+H]⁺, 400.9 [M+H+2]⁺. ¹H NMR (400 MHz, CDCl₃) δ: 8.29 (s, 1H), 7.56 (s, 1H), 6.02 (t, J=6.0 Hz, 1H), 4.52 (t, J=4.6 Hz, 2H), 3.99-3.87 (m, 2H), 3.46-3.31 (m, 4H), 3.11 (q, J=6.4 Hz, 2H), 2.38 (t, J=6.0 Hz, 1H), 1.80-1.71 (m, 2H), 1.14 (t, J=7.0 Hz, 3H).

Reference Embodiment 13: Fragment BB-13

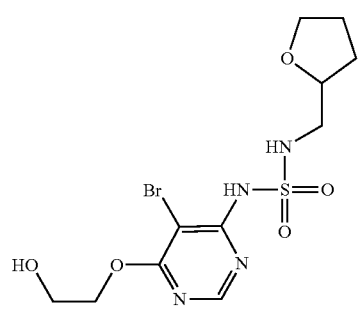 [SMILES: O=S(=O)(NCC1CCCO1)Nc1ncnc(OCCO)c1Br]

Synthetic Route:

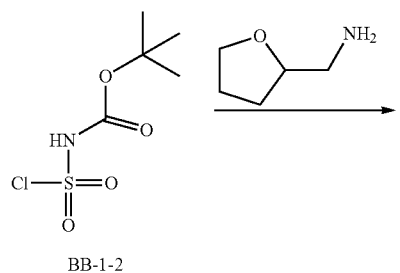

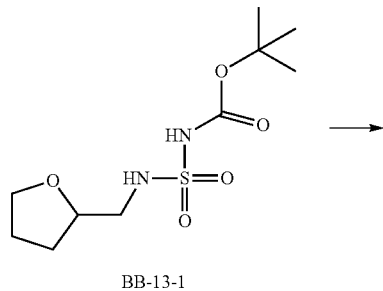

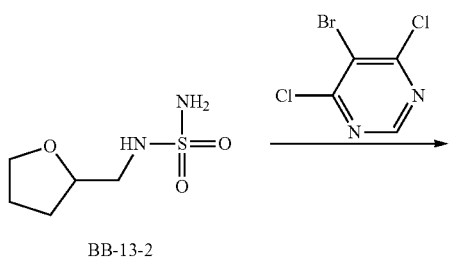

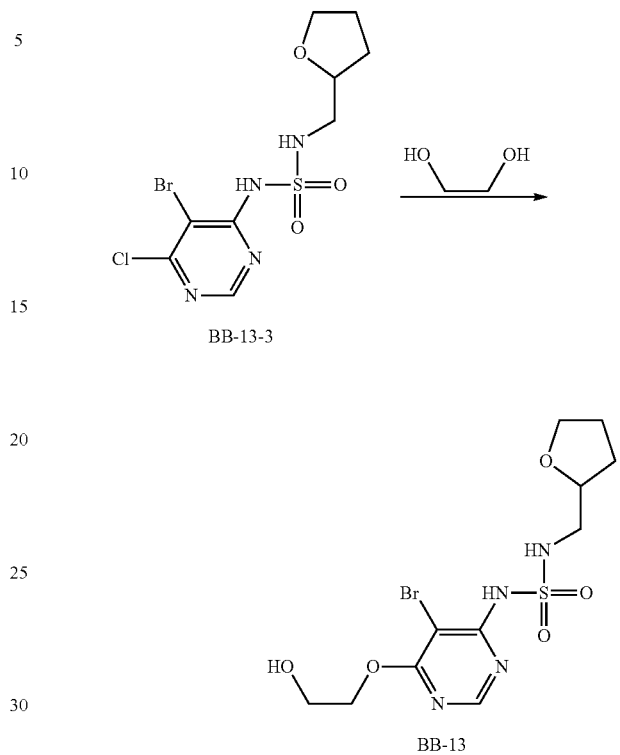

Step 1: Synthesis of Compound BB-13-1

At 0° C., a solution of the compound BB-1-2 (49.43 mmol, crude product) in dichloromethane was slowly added to a solution of 2-tetrahydrofurfurylamine (5.00 g, 49.43 mmol, 5.10 mL) and triethylamine (10.00 g, 98.86 mmol, 13.70 mL) in dichloromethane (50.00 mL) (dropping time was about 0.5 hour), and the reaction mixture was warmed to room temperature and stirred for 18 hours under nitrogen atmosphere. After the reaction was completed, water (100 mL) was added, and the mixture was extracted with dichloromethane (90 mL×2). The organic phases were combined, washed with 1 M dilute hydrochloric acid (50 mL) and saturated brine (200 mL) respectively, dried over anhydrous sodium sulfate, filtered, and the solvent of filtrate was removed under reduced pressure to obtain the target compound BB-13-1 (white solid, 8.30 g, yield: 59.90%). ¹H NMR (400 MHz, CDCl₃) δ: 5.75 (d, J=4.8 Hz, 1H), 4.02 (dd, J=3.9, 6.7 Hz, 1H), 3.88-3.64 (m, 2H), 3.30-2.83 (m, 2H), 2.06-1.76 (m, 3H), 1.71-1.18 (m, 10H).

Step 2: Synthesis of Compound BB-13-2

At room temperature, the compound BB-13-1 (8.00 g, 28.54 mmol) was added to water (100.00 mL), and the reaction mixture was heated to 110° C. and stirred for 2 hours under nitrogen atmosphere. After the reaction was completed, the mixture was cooled to room temperature and extracted with ethyl acetate (100 mL×3). The organic phases were combined, washed with saturated brine (200 mL), dried over anhydrous sodium sulfate, filtered, and the solvent of filtrate was removed under reduced pressure to obtain the target compound BB-13-2 (colorless oil, 4.90 g, yield: 95.27%). ¹H NMR (400 MHz, CDCl₃) δ: 5.18-5.01 (m, 1H), 4.07-3.91 (m, 1H), 3.86-3.61 (m, 2H), 3.27-2.90 (m, 2H), 1.96-1.74 (m, 3H), 1.62-1.41 (m, 1H).

53

Step 3: Synthesis of Compound BB-13-3

At room temperature, potassium tert-butoxide (3.86 g, 34.40 mmol) was added to a solution of the compound BB-13-2 (3.10 g, 17.20 mmol) in dimethyl sulfoxide (20.00 mL), the reaction mixture was stirred at room temperature for 0.5 hour under nitrogen atmosphere, then 5-bromo-4,6-dichloropyrimidine (3.92 g, 17.20 mmol) was added, and the reaction mixture was stirred at room temperature for 15 hours under nitrogen atmosphere. After the reaction was completed, water (60 mL) was added, the pH was adjusted to 4 with 1 M dilute hydrochloric acid, and the mixture was extracted with ethyl acetate (30 mL×3). The organic phases were combined, washed with saturated brine (30 mL), dried over anhydrous sodium sulfate, filtered, and the solvent of filtrate was removed under reduced pressure. The residue was separated by column chromatography (eluent: petroleum ether/ethyl acetate=1/1, volume ratio) to obtain the target compound BB-13-3 (yellow solid, 2.10 g, yield: 32.85%). $^1$H NMR (400 MHz, CDCl$_3$) δ: 8.65-8.36 (m, 1H), 8.08-7.70 (m, 1H), 5.99-5.80 (m, 1H), 4.08-3.90 (m, 1H), 3.82-3.55 (m, 2H), 3.25-3.13 (m, 1H), 3.04-2.89 (m, 1H), 1.98-1.72 (m, 3H), 1.60-1.44 (m, 1H).

Step 4: Synthesis of Compound BB-13

At room temperature, potassium tert-butoxide (1.27 g, 11.30 mmol) was added to ethylene glycol (10.58 g, 170.40 mmol, 9.53 mL), the reaction mixture was heated to 40° C. and stirred for 0.5 hour under nitrogen atmosphere, then a solution of compound BB-13-3 (2.10 g, 5.65 mmol) in ethylene glycol dimethyl ether (30.00 mL) was added to mixture, and the reaction mixture was heated to 120° C. and stirred for 15 hours under nitrogen atmosphere. After the reaction was completed, the mixture was cooled to room temperature, added with water (60 mL), adjusted to pH of 4 with 1 M dilute hydrochloric acid, and extracted with ethyl acetate (50 mL×3). The organic phases were combined, washed with saturated brine (50 mL), dried over anhydrous sodium sulfate, filtered, and the solvent of filtrate was removed under reduced pressure. The residue was separated by column chromatography (eluent: petroleum ether/ethyl acetate=1/2, volume ratio) to obtain the target compound BB-13 (yellow oil, 1.80 g, yield: 78.35%). MS-ESI m/z: 396.8 [M+H]$^+$, 398.8 [M+H+2]$^+$.

Reference Embodiment 14: Fragment BB-14

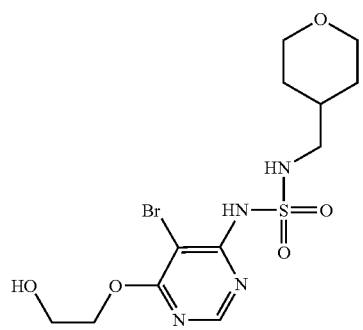 [SMILES: O=S(=O)(NCC1CCOCC1)Nc1ncnc(OCCO)c1Br]

54

Synthetic Route:

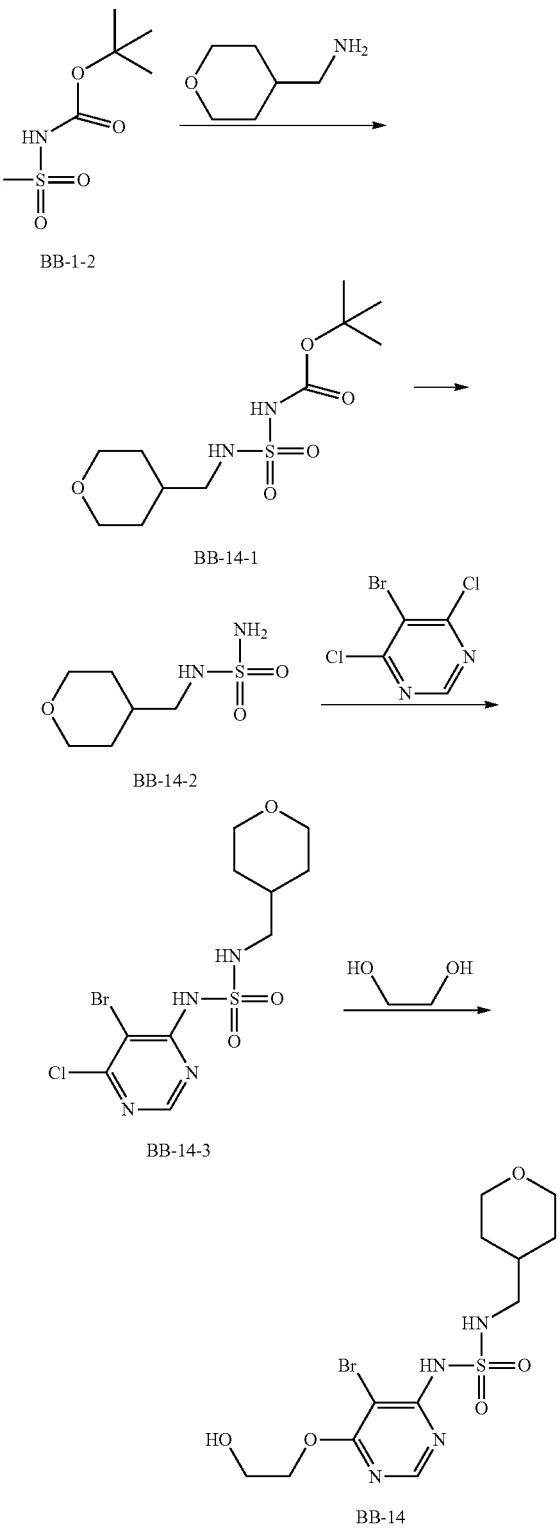

Step 1: Synthesis of Compound BB-14-1

At 0° C., a solution of the compound BB-1-2 (43.41 mmol, crude product) in dichloromethane was added to a solution of 4-(aminomethyl)tetrahydro-2H-pyran (5.00 g, 43.41 mmol) and triethylamine (8.79 g, 86.82 mmol, 12.04 mL) in dichloromethane (50.00 mL), the reaction mixture was warmed to room temperature and stirred for 12 hours under nitrogen atmosphere. After the reaction was completed, water (80 mL) was added and the mixture was extracted with dichloromethane (80 mL×2). The organic phases were combined, washed with 1 M dilute hydrochloric acid (50 mL) and saturated brine (200 mL) respectively, dried over anhydrous sodium sulfate, filtered, and the solvent of filtrate was removed under reduced pressure to obtain the target compound BB-14-1 (off-white oil, 5.20 g, yield: 40.69%).

Step 2: Synthesis of Compound BB-14-2

At room temperature, the compound BB-14-1 (5.00 g, 16.99 mmol) was added to water (100.00 mL), and the reaction mixture was heated to 100° C. and stirred for 12 hours. After the reaction was completed, the mixture was cooled to room temperature and extracted with ethyl acetate (80 mL×2). The organic phases were combined, washed with saturated brine (100 mL×2), dried over anhydrous sodium sulfate, filtered, and the solvent of filtrate was removed under reduced pressure to obtain the target compound BB-14-2 (light yellow oil, 1.70 g, yield: 51.51%).

Step 3: Synthesis of Compound BB-14-3

At 35° C., a mixture of the compound BB-14-2 (1.70 g, 8.75 mmol) and potassium tert-butoxide (2.95 g, 26.25 mmol) in dimethyl sulfoxide (50.00 mL) was stirred for 0.5 hour, then 5-bromo-4,6-dichloropyrimidine (1.99 g, 8.75 mmol) was added, the reaction mixture was stirred at 35° C. for 12 hours. After the reaction was completed, the mixture was added with 0.5 M diluted hydrochloric acid (50 mL) and extracted with ethyl acetate (50 mL×3). The organic phases were combined, washed with saturated brine (100 mL×2), dried over anhydrous sodium sulfate, and the solvent of filtrate was removed under reduced pressure. The residue was separated by column chromatography (eluent: petroleum ether/ethyl acetate=10/1-1/1, volume ratio) to obtain the target compound BB-14-3 (yellow solid, 1.20 g, yield: 12.80%). MS-ESI m/z: 384.8 [M+H]$^+$, 386.8 [M+H+2]$^+$.

Step 4: Synthesis of Compound BB-14

At room temperature, potassium tert-butoxide (1.05 g, 9.33 mmol) was added to ethylene glycol (33.30 g, 536.49 mmol, 30.00 mL), the reaction mixture was heated to 40° C. and stirred for 0.5 hour under nitrogen atmosphere, then a solution of the compound BB-14-3 (1.20 g, 3.11 mmol) in ethylene glycol dimethyl ether (20.00 mL) was added to mixture, and the reaction mixture was heated to 110° C. and stirred for 12 hours under nitrogen atmosphere. After the reaction was completed, the mixture was cooled to room temperature, added with 0.5 M dilute hydrochloric acid (30 mL), and extracted with ethyl acetate (50 mL×3). The organic phases were combined, washed with saturated brine (100 mL×2), dried over anhydrous sodium sulfate, filtered, and the solvent of filtrate was removed under reduced pressure. The residue was separated by column chromatography (eluent: petroleum ether/ethyl acetate=10/1-0/1, volume ratio) to obtain the target compound BB-14 (light yellow solid, 200.00 mg, yield: 14.59%). MS-ESI m/z: 410.9 [M+H]$^+$, 412.9 [M+H+2]$^+$. $^1$H NMR (400 MHz, CDCl$_3$) δ: 8.38 (s, 1H), 7.62 (br s, 1H), 5.65 (t, J=6.5 Hz, 1H), 4.60 (t, J=4.8 Hz, 2H), 4.05-3.89 (m, 4H), 3.38 (t, J=10.8 Hz, 2H), 2.93 (t, J=6.5 Hz, 2H), 1.86-1.75 (m, 1H), 1.71-1.61 (m, 2H), 1.31-1.22 (m, 2H).

Reference Embodiment 15: Fragment BB-15

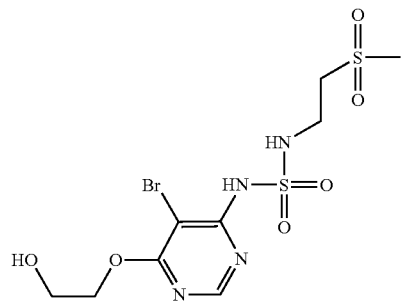 [SMILES: CS(=O)(=O)CCNS(=O)(=O)Nc1ncnc(OCCO)c1Br]

Synthetic Route:

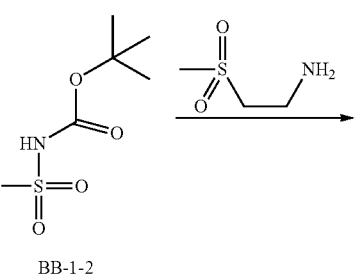

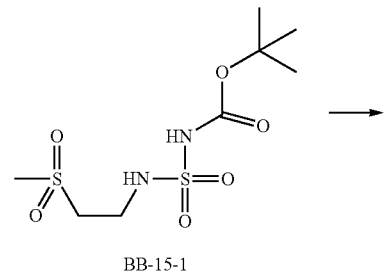

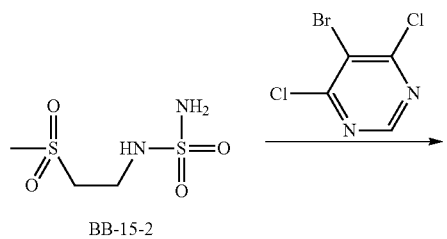

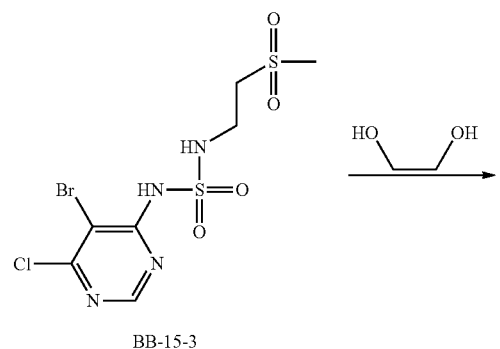

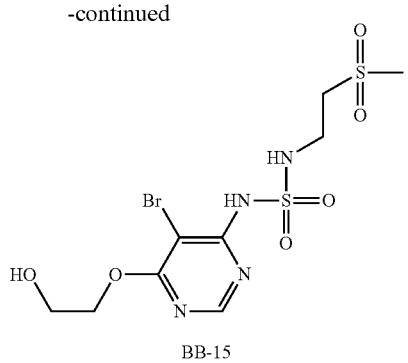

BB-15

Step 1: Synthesis of Compound BB-15-1

At 0° C., a solution of the compound BB-1-2 (31.32 mmol, crude product) in dichloromethane was slowly added dropwise to a mixed solution of 2-aminoethylmethylsulfone hydrochloride (5.00 g, 31.32 mmol) and triethylamine (6.34 g, 62.64 mmol, 8.68 mL) in dichloromethane (50.00 mL) (dropping time was about 0.5 hour), and the reaction mixture was warmed to room temperature and stirred for 18 hours under nitrogen atmosphere. After the reaction was completed, water (100 mL) was added, and the mixture was extracted with dichloromethane (100 mL×2). The organic phases were combined, washed with 1 M dilute hydrochloric acid (50 mL) and saturated brine (80 mL) respectively, dried over anhydrous sodium sulfate, filtered, and the solvent of filtrate was removed under reduced pressure to obtain the target compound BB-15-1 (white solid 5.00 g, yield: 52.81%). $^1$H NMR (400 MHz, DMSO_d$_6$) δ: 11.04 (s, 1H), 7.83 (br s, 1H), 3.44 (br s, 2H), 3.35-3.30 (m, 2H), 3.02 (s, 3H), 1.44 (s, 9H).

Step 2: Synthesis of Compound BB-15-2

At room temperature, the compound BB-15-1 (4.80 g, 15.87 mmol) was added to water (100.00 mL), and the reaction mixture was heated to 110° C. and stirred for 2 hours under nitrogen atmosphere. After the reaction was completed, the mixture was cooled to room temperature, extracted with ethyl acetate (100 mL), the organic phase was discarded, and the aqueous phase was concentrated under reduced pressure to obtain the target compound BB-15-2 (colorless oil, 2.10 g, yield: 65.43%). $^1$H NMR (400 MHz, MeOD) δ: 3.55-3.47 (m, 2H), 3.41-3.35 (m, 2H), 3.06-3.02 (s, 3H).

Step 3: Synthesis of Compound BB-15-3

At room temperature, potassium tert-butoxide (2.22 g, 19.78 mmol) was added to a solution of the compound BB-15-2 (2.00 g, 9.89 mmol) in dimethyl sulfoxide (20.00 mL), the reaction mixture was stirred at room temperature for 0.5 hour under nitrogen atmosphere, then 5-bromo-4,6-dichloropyrimidine (2.25 g, 9.89 mmol) was added, and the reaction mixture was stirred for 15 hours at room temperature under nitrogen atmosphere. After the reaction was completed, water (60 mL) was added, the pH was adjusted to 4 with 1 M dilute hydrochloric acid, and the mixture was extracted with ethyl acetate (30 mL×3). The organic phases were combined, washed with saturated brine (30 mL), dried over anhydrous sodium sulfate, filtered, and the solvent of filtrate was removed under reduced pressure. The residue was separated by column chromatography (eluent: petroleum ether/ethyl acetate=1/1, volume ratio) to obtain the target compound BB-15-3 (yellow solid, 1.80 g, yield: 43.98%). MS-ESI m/z: 392.8 [M+H]$^+$, 394.8 [M+H+2]$^+$. $^1$H NMR (400 MHz, CDCl$_3$) δ: 8.60 (s, 1H), 6.36 (br s, 1H), 3.66 (q, J=6.0 Hz, 2H), 3.46-3.25 (m, 2H), 3.09-2.82 (m, 3H).

Step 4: Synthesis of Compound BB-15

Under nitrogen atmosphere and at 40° C., a mixture of ethylene glycol (4.28 g, 68.95 mmol, 3.86 mL) and potassium tert-butoxide (513.07 mg, 4.57 mmol) was stirred for 0.5 hour, and then a solution of the compound BB-15-3 (0.9 g, 2.29 mmol) in ethylene glycol dimethyl ether (30.00 mL) was added to mixture, and the reaction mixture was heated to 60° C. and stirred for 3 hours under nitrogen atmosphere. After the reaction was completed, the mixture was cooled to room temperature, added with water (60 mL), adjusted to pH of 4 with 1 M dilute hydrochloric acid, and extracted with ethyl acetate (50 mL×3). The organic phases were combined, washed with saturated brine (50 mL), dried over anhydrous sodium sulfate, filtered, and the solvent of filtrate was removed under reduced pressure. The residue was separated by column chromatography (eluent: petroleum ether/ethyl acetate=1/2, volume ratio) to obtain the target compound BB-15 (light yellow oil, 327.27 mg, yield: 33.40%). MS-ESI m/z: 440.9 [M+Na]$^+$, 442.9 [M+Na+2]$^+$.

Reference Embodiment 16: Fragment BB-16

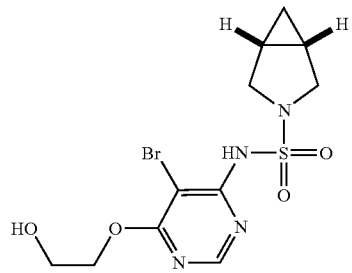 [SMILES: O=S(=O)(Nc1ncnc(OCCO)c1Br)N1C[C@H]2C[C@H]2C1]

Synthetic Route:

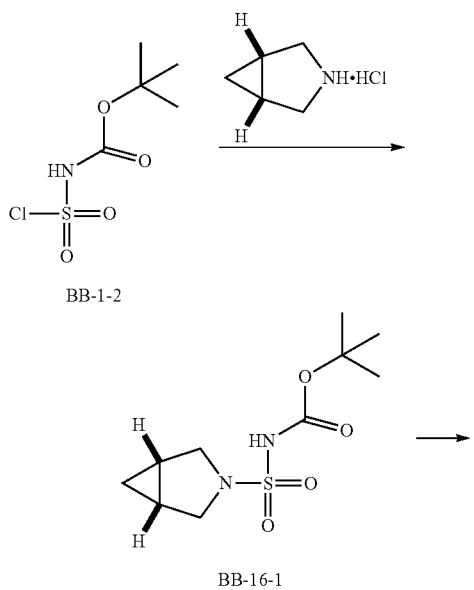

BB-1-2

BB-16-1

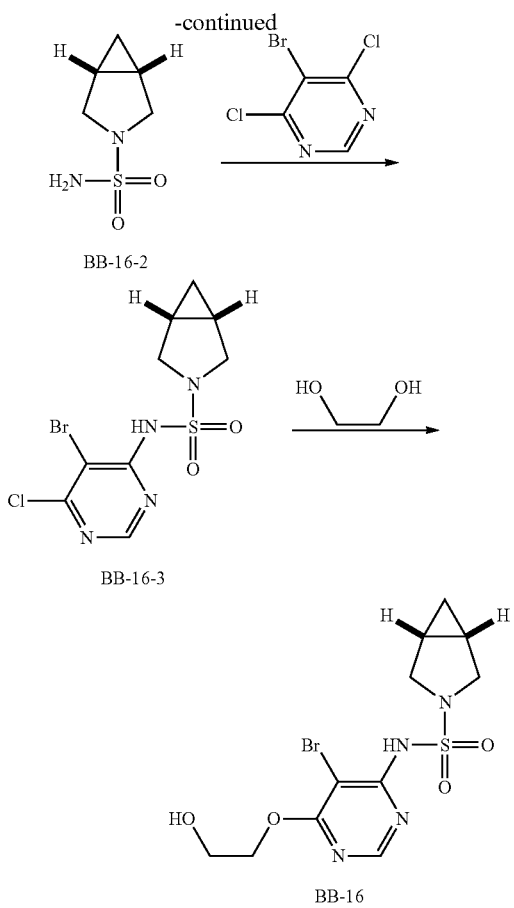

Step 1: Synthesis of Compound BB-16-1

At 0-5° C., a solution of the compound BB-1-2 (9.19 mmol, crude product) in dichloromethane was slowly added dropwise to a solution of 3-azabicyclo[3.1.0]hexane in hydrochloride (900.00 mg, 7.53 mmol) and triethylamine (2.28 g, 22.58 mmol) in dichloromethane (10 mL) (dropping time was about 1 hour), and the reaction mixture was warmed to room temperature and stirred for 16 hours under nitrogen atmosphere. After the reaction was completed, the solvent was removed under reduced pressure, and the residue was added with water (20 mL), adjusted to pH of 4-5 with 1 M dilute hydrochloric acid, and extracted with ethyl acetate (25 mL×4). The organic phases were combined, washed with saturated brine (100 mL), dried over anhydrous sodium sulfate, filtered, and the solvent of filtrate was removed under reduced pressure to obtain the target compound BB-16-1 (white solid, 1.90 g, yield: 96.19%). $^1$H NMR (400 MHz, CDCl$_3$) δ: 3.56-3.68 (m, 4H), 1.55-1.59 (m, 2H), 1.51 (s, 9H), 0.69-0.74 (m, 1H), 0.41-0.45 (m, 1H).

Step 2: Synthesis of Compound BB-16-2

At room temperature, trifluoroacetic acid (3.30 g, 28.96 mmol) was added to a solution of compound BB-16-1 (1.90 g, 7.24 mmol) in dichloromethane (10.00 mL) in one portion, the reaction mixture was stirred at room temperature for 16 hours under nitrogen atmosphere. After the reaction was completed, the solvent of the reaction mixture was removed under reduced pressure to obtain compound BB-16-2 (off-white solid, 1.44 g, yield: 72.00%, trifluoroacetate salt). $^1$H NMR (400 MHz, CDCl$_3$) δ: 3.28-3.36 (m, 4H), 1.54-1.59 (m, 2H), 0.61-0.69 (m, 1H), 0.44-0.58 (m, 1H).

Step 3: Synthesis of Compound BB-16-3

At room temperature, potassium tert-butoxide (1.75 g, 15.63 mmol) was added to a mixture of the trifluoroacetate salt of the compound BB-16-2 (1.44 g, 5.21 mmol) in dimethyl sulfoxide (30.00 mL) in one portion, the reaction mixture was stirred at room temperature for 0.5 hour under nitrogen atmosphere, then 5-bromo-4,6-dichloropyrimidine (1.42 g, 6.25 mmol) was added to mixture, the reaction mixture was stirred for 16 hours at room temperature under nitrogen atmosphere. After the reaction was completed, ice water (60 mL) was added, the pH was adjusted to 4-5 with 4 M diluted hydrochloric acid, and the mixture was extracted with ethyl acetate (100 mL×3). The organic phases were combined, washed with saturated brine (200 mL), dried over anhydrous sodium sulfate, and filtered. the solvent of filtrate was removed under reduced pressure, and the residue was separated by column chromatography (eluent: petroleum ether/ethyl acetate=10/1-1/1, volume ratio) to obtain the target compound BB-16-3 (brown solid, 1.40 g, yield: 74.14%). $^1$H NMR (400 MHz, CDCl$_3$) δ: 8.59 (s, 1H), 7.80 (br s, 1H), 3.73-3.79 (m, 2H), 3.66-3.72 (m, 2H), 1.58-1.62 (m, 2H), 0.69-0.76 (m, 1H), 0.33 (q, J=4.3 Hz, 1H).

Step 4: Synthesis of Compound BB-16

At room temperature, potassium tert-butoxide (760.78 mg, 6.78 mmol) was added to ethylene glycol (22.20 g, 357.67 mmol), the reaction mixture was heated to 40° C. and stirred for 0.5 hour under nitrogen atmosphere, and then a solution of the compound BB-16-3 (799.18 mg, 2.26 mmol) in ethylene glycol dimethyl ether (10.00 mL) was added to mixture, and the reaction mixture was heated to 110° C. and stirred for 39 hours under nitrogen atmosphere. After the reaction was completed, the mixture was cooled to room temperature, and the solvent was removed under reduced pressure. The residue was added with ice water (60 mL), adjusted to pH of 4-5 with 1 M dilute hydrochloric acid, and extracted with ethyl acetate (60 mL×2). The organic phases were combined, washed with saturated brine (120 mL), dried over anhydrous sodium sulfate, filtered, and the solvent of filtrate was removed under reduced pressure. The residue was separated by preparative chromatography (eluent: petroleum ether/ethyl acetate=1/1, volume ratio) to obtain the target compound BB-16 (yellow solid, 520.00 mg, yield: 59.45%). $^1$H NMR (400 MHz, CDCl$_3$) δ: 8.38 (s, 1H), 7.63 (br s, 1H), 4.55-4.61 (m, 2H), 3.94-4.02 (m, 2H), 3.69-3.74 (m, 2H), 3.64-3.69 (m, 2H), 2.48 (br s, 1H), 1.49-1.58 (m, 2H), 0.62-0.71 (m, 1H), 0.30-0.37 (m, 1H).

Reference Embodiment 17: Fragment BB-17

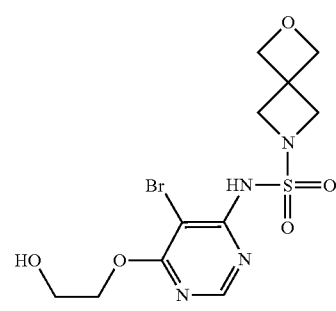 [SMILES: O=S(=O)(Nc1ncnc(OCCO)c1Br)N1CC2(COC2)C1]

Synthetic Route:

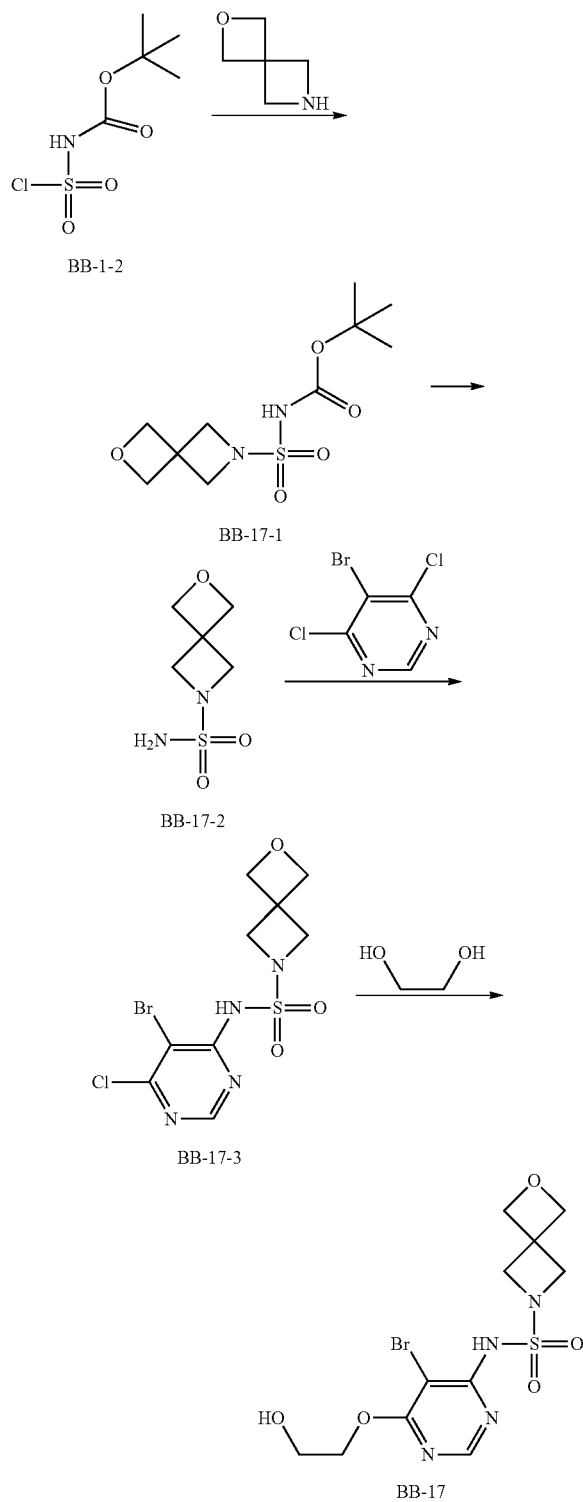

Step 1: Synthesis of Compound BB-17-1

At 0° C., a solution of the compound BB-1-2 (12.39 mmol, crude product) in dichloromethane was added dropwise to a solution of 2-oxa-6-azaspiro[3.3]heptane (1.17 g, 11.80 mmol) and triethylamine (3.58 g, 35.40 mmol) in dichloromethane (10 mL) (dropping time about 1 hour), the reaction mixture was warmed to room temperature and stirred for 16 hours. After the reaction was completed, the solvent was removed under reduced pressure, the residue was added with water (20 mL), the pH was adjusted to 4-5 with 5 M dilute hydrochloric acid, and extracted with ethyl acetate (25 mL×3). The organic phases were combined, washed with saturated brine (100 mL), dried over anhydrous sodium sulfate, filtered, and the solvent was removed under reduced pressure to obtain the target compound BB-17-1 (white solid, 1.70 g, yield: 51.76%). $^1$H NMR (400 MHz, CDCl$_3$) δ: 7.07 (br s, 1H), 4.79 (s, 4H); 4.34 (s, 4H), 1.52 (s, 9H).

Step 2: Synthesis of Compound BB-17-2

At room temperature, the compound BB-17-1 (1.70 g, 6.11 mmol) was added to water (10.00 mL), and the reaction mixture was heated to 100° C. and stirred for 1 hour. After the reaction was completed, the mixture was cooled to room temperature and extracted with ethyl acetate (10 mL×3). The organic phases were combined, washed with saturated brine (30 mL), dried over anhydrous sodium sulfate, filtered, and the solvent of filtrate was removed under reduced pressure to obtain the target compound BB-17-2 (white solid, 920.00 mg, yield: 84.49%). $^1$H NMR (400 MHz, CDCl$_3$) δ: 4.78 (s, 4H), 4.39 (br s, 2H), 4.04 (s, 4H).

Step 3: Synthesis of Compound BB-17-3

At room temperature, the compound BB-17-2 (920.00 mg, 5.16 mmol) and potassium tert-butoxide (1.50 g, 13.37 mmol) were added to dimethyl sulfoxide (15.00 mL), and the reaction mixture was stirred at room temperature for 0.5 hour. Then, 5-bromo-4,6-dichloropyrimidine (1.41 g, 6.19 mmol) was added to mixture, and the reaction mixture was stirred at room temperature for 18 hours. After the reaction was completed, ice water (40 mL) was added, the pH was adjusted to 4-5 with 4 M dilute hydrochloric acid, and the mixture was extracted with ethyl acetate (40 mL×3). The organic phases were combined, washed with saturated brine (120 mL), dried over anhydrous sodium sulfate, filtered, and the solvent of filtrate was removed under reduced pressure. The residue was separated by preparative chromatography plate (eluent: dichloromethane/methanol=10/1, volume ratio) to obtain the target compound BB-17-3 (brown solid, 430.00 mg, yield: 16.43%). MS-ESI m/z: 368.8 [M+H]$^+$, 370.8 [M+H+2]$^+$.

Step 4: Synthesis of Compound BB-17

At room temperature, potassium tert-butoxide (390.49 mg, 3.48 mmol) was added to ethylene glycol (15.23 g, 245.36 mmol), the reaction mixture was heated to 40° C. and stirred for 0.5 hour under nitrogen atmosphere, and then a solution of the compound BB-17-3 (430.00 mg, 1.16 mmol) in ethylene glycol dimethyl ether (10.00 mL) was slowly added dropwise to mixture, and the reaction mixture was heated to 110° C. and stirred for 48 hours under nitrogen atmosphere. After the reaction was completed, the mixture was cooled to room temperature, and the solvent was removed under reduced pressure. The residue was added with ice water (30 mL), adjusted the pH to 4-5 with 1 M dilute hydrochloric acid, and extracted with ethyl acetate (30 mL×4). The organic phases were combined, washed with saturated brine (120 mL), dried over anhydrous sodium sulfate, filtered, and the solvent of filtrate was removed under reduced pressure. The residue was separated by preparative chromatography (eluent: dichloromethane/methanol=10/1. volume ratio) to obtain the target compound BB-17 (yellow solid, 150.00 mg, yield: 30.86%). MS-ESI m/z: 417.0 [M+Na]$^+$, 417.0 [M+Na+2]$^+$.

Reference Embodiment 18: Fragment BB-18

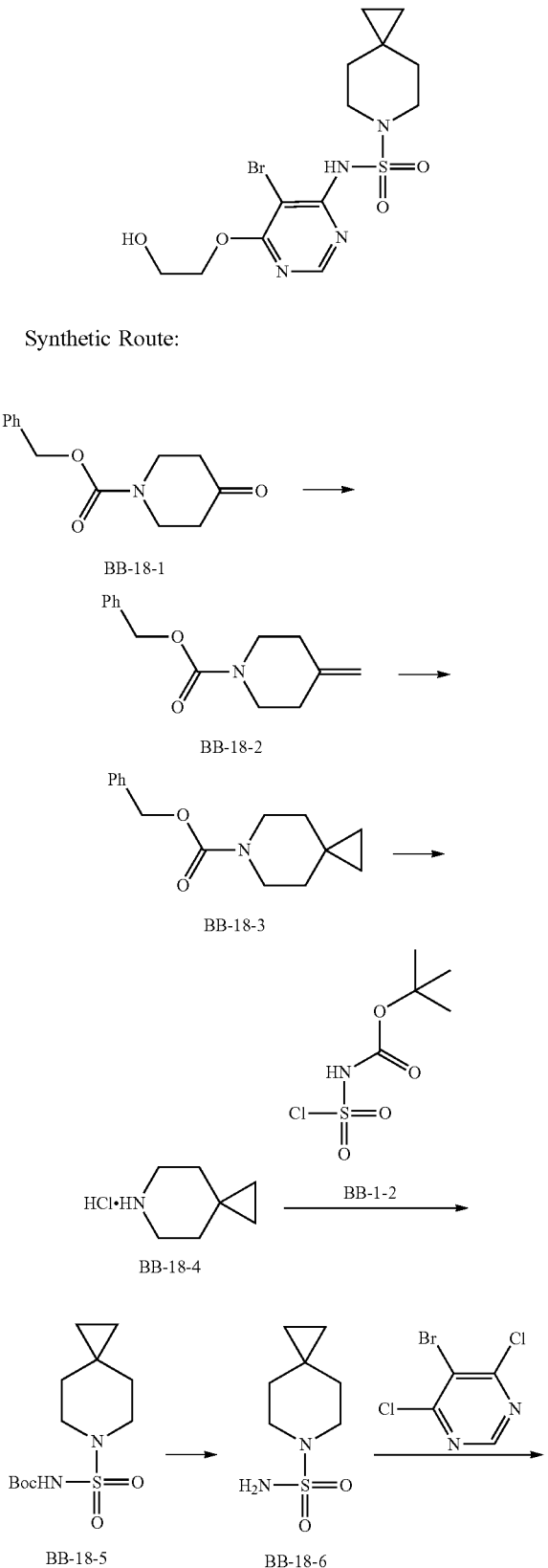

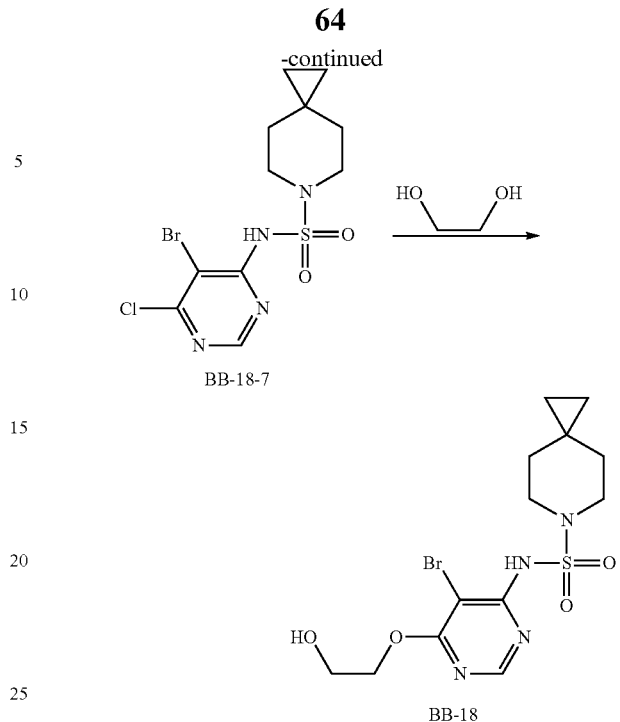

Step 1: Synthesis of Compound BB-18-2

At 0° C., a solution of potassium tert-butoxide (7.22 g, 64.31 mmol) in tetrahydrofuran (50 mL) was added dropwise to a suspension of methyltriphenylphosphonium bromide (22.97 g, 64.31 mmol) in tetrahydrofuran (100 mL), the reaction mixture was warmed to room temperature and stirred for 1 hour under nitrogen atmosphere, then the reaction mixture was cooled to 0° C., and a solution of the compound BB-18-1 (10.00 g, 42.87 mmol) in tetrahydrofuran (50 mL) was added in one portion. The reaction mixture was warmed to room temperature and stirred for 64 hours under nitrogen atmosphere. After the reaction was completed, water (50 mL) and petroleum ether (50 mL) were added in sequence, and the liquid was separated. The aqueous phase was extracted with petroleum ether (50 mL×2). The organic phases were combined, washed with saturated brine (150 mL), dried over anhydrous sodium sulfate, filtered, and the solvent of filtrate was removed under reduced pressure. The residue was separated by column chromatography (eluent: petroleum ether/ethyl acetate=1/0-10/1, volume ratio) to obtain compound BB-18-2 (colorless oil, 5.20 g, yield: 48.56%). MS-ESI m/z: 232.0 [M+H]$^+$. $^1$H NMR (400 MHz, CDCl$_3$) δ: 7.40-7.29 (m, 5H), 5.15 (s, 2H), 4.76 (s, 2H), 3.51 (t, J=5.8 Hz, 4H), 2.19 (t, J=5.8 Hz, 4H).

Step 2: Synthesis of Compound BB-18-3

At −40° C., a solution of trifluoroacetic acid (10.25 g, 89.92 mmol) in dichloromethane (10 mL) was added dropwise to a solution of diethylzinc (1 M, 89.92 mL) in dichloromethane (50 mL), the reaction mixture was stirred at −40° C. for 0.5 hour under nitrogen atmosphere, and then a solution of diiodomethane (24.08 g, 89.92 mmol) in dichloromethane (10 mL) was added to mixture, the reaction mixture was stirred at −40° C. for 0.5 hour under nitrogen atmosphere. Then a solution of the compound BB-18-2 (5.20 g, 22.48 mmol) in dichloromethane (10 mL) was added, the reaction mixture was warmed to room temperature and stirred for 16 hours under nitrogen atmosphere. After the reaction was completed, dichloromethane (30 mL) and saturated sodium bicarbonate aqueous solution (80 mL)

were added and stirred for 5 minutes, followed by precipitation, filtration and liquid separation. The organic phase was washed with saturated brine (100 mL), dried over anhydrous sodium sulfate, filtered, the solvent of filtrate was removed under reduced pressure, and the residue was separated by column chromatography (eluent: petroleum ether/ethyl acetate=100/1-10/1, volume ratio) to obtain a yellow oil, which was separated by preparative HPLC again to obtain compound BB-18-3 (light yellow oil, 4.00 g, yield: 47.46%). MS-ESI m/z: 246.0 [M+H]$^+$. $^1$H NMR (400 MHz, CDCl$_3$) δ: 7.40-7.29 (m, 5H), 5.15 (s, 2H), 3.57-3.47 (m, 4H), 1.35 (br s, 4H), 0.34 (s, 4H).

Step 3: Synthesis of Compound BB-18-4

At room temperature, wet palladium carbon (150.00 mg, purity: 10%) was added to a solution of the compound BB-18-3 (1.50 g, 6.11 mmol) in tetrahydrofuran (15.00 mL), and the reaction mixture was reacted under hydrogen (3.5 MPa) atmosphere and stirred at room temperature for 40 hours. After the reaction was completed, the reaction mixture was filtered, followed by addition of hydrochloric acid/ethyl acetate (4 M, 10 mL), stirred for 15 minutes, and concentrated under reduced pressure to obtain compound BB-18-4 (yellow solid, 900.00 mg, yield: 99.76%, hydrochloride). $^1$H NMR (400 MHz, DMSO_d$_6$) δ: 9.13 (br s, 2H), 3.02 (br s, 4H), 1.54 (t, J=5.0 Hz, 4H), 0.37 (s, 4H).

Step 4: Synthesis of Compound BB-18-5

At 0° C., a solution of the compound BB-18-4 (1.20 g, 8.13 mmol, hydrochloride) in dichloromethane (20 mL) was added dropwise to a solution of the compound BB-1-2 (8.54 mmol, crude product) in dichloromethane and a mixture of dichloromethane (10 mL) and triethylamine (3.29 g, 32.52 mmol) (dropping time was about 1 hour. The reaction mixture was warmed to room temperature and stirred for 16 hours under nitrogen atmosphere. After the reaction was completed, the solvent was removed under reduced pressure, and the residue was added with water (20 mL), adjusted to pH of 4-5 with 4 M dilute hydrochloric acid (10 mL), and extracted with ethyl acetate (25 mL×4). The organic phases were combined, washed with saturated brine (100 mL), dried over anhydrous sodium sulfate, filtered, and the solvent of filtrate was removed under reduced pressure to obtain compound BB-18-5 (light yellow solid, 1.32 g, yield: 55.91%). $^1$H NMR (400 MHz, CDCl$_3$) δ: 7.05 (br s, 1H), 3.47-3.40 (m, 4H), 1.52 (s, 9H), 1.50-1.47 (m, 4H), 0.38 (s, 4H).

Step 5: Synthesis of Compound BB-18-6

At room temperature, trifluoroacetic acid (1.53 g, 13.42 mmol) was added to a solution of compound BB-19-5 (580.00 mg, 2.00 mmol) in dichloromethane (3.00 mL) in one portion, the reaction mixture was stirred at room temperature for 16 hours under nitrogen atmosphere. After the reaction was completed, the solvent was removed under reduced pressure to obtain compound BB-18-6 (light yellow solid, 600.00 mg, yield: 98.50%, trifluoroacetate). $^1$H NMR (400 MHz, CDCl$_3$) δ: 3.23 (t, J=5.5 Hz, 4H), 1.50 (t, J=5.5 Hz, 4H), 0.36 (s, 4H).

Step 6: Synthesis of Compound BB-18-7

At room temperature, potassium tert-butoxide (1.39 g, 12.42 mmol) was added to a solution of compound the BB-18-6 (1.26 g, 4.14 mmol, trifluoroacetate) in dimethyl sulfoxide (10.00 mL) in one portion, the reaction mixture was stirred at room temperature for 0.5 hour under nitrogen atmosphere, then 5-bromo-4,6-dichloropyrimidine (1.04 g, 4.55 mmol) was added to reaction mixture, the reaction mixture was stirred for 20 hours at room temperature under nitrogen atmosphere. After the reaction was completed, ice water (20 mL) was added, the pH was adjusted to 4-5 with 1 M dilute hydrochloric acid, and the mixture was extracted with ethyl acetate (30 mL×3). The organic phases were combined, washed with saturated brine (120 mL), dried over anhydrous sodium sulfate, filtered, and the solvent was removed under reduced pressure. The residue was separated by a chromatography plate (eluent: petroleum ether/ethyl acetate=1/1, volume ratio) to obtain compound BB-18-7 (yellow oil, 600.00 mg, yield: 35.86%). $^1$H NMR (400 MHz, CDCl$_3$) δ: 8.53 (s, 1H), 4.40 (br s, 1H), 3.20-3.28 (m, 4H), 1.49-1.55 (m, 4H), 0.35 (s, 4H).

Step 7: Synthesis of Compound BB-18

At room temperature, potassium tert-butoxide (353.46 mg, 3.15 mmol) was added to a solution of ethylene glycol (16.03 g, 258.27 mmol) in ethylene glycol dimethyl ether (3.00 mL), and the reaction mixture was heated to 40° C. and stirred for 0.5 hour under nitrogen atmosphere, then a solution of the compound BB-18-7 (400.00 mg, 1.05 mmol) in ethylene glycol dimethyl ether (5.00 mL) was added to reaction solution, and the reaction mixture was heated to 110° C. and stirred for 40 hours under nitrogen atmosphere. After the reaction was completed, the mixture was cooled to room temperature, and the solvent was removed under reduced pressure. The residue was added with ice water (30 mL), adjusted to pH of 5-6 with 1 M dilute hydrochloric acid, and extracted with ethyl acetate (30 mL×3). The organic phases were combined, washed with saturated brine (100 mL), dried over anhydrous sodium sulfate, filtered, and the solvent of filtrate was removed under reduced pressure. The residue was separated by chromatography (eluent: ethyl acetate/petroleum ether=1/1. volume ratio) to obtain compound BB-18 (yellow oil, 180.00 mg, yield: 42.09%). $^1$H NMR (400 MHz, CDCl$_3$) δ: 8.37 (s, 1H), 4.61-4.56 (m, 2H), 4.01-3.97 (m, 2H), 3.54-3.47 (m, 4H), 1.52-1.45 (m, 4H), 0.36-0.31 (m, 4H).

Embodiment 1: WX001

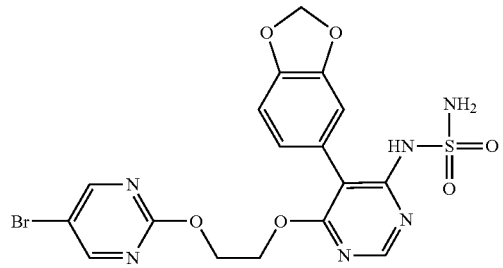 [SMILES: NS(=O)(=O)Nc1ncnc(OCCOc2ncc(Br)cn2)c1-c1ccc2c(c1)OCO2]

Synthetic Route:

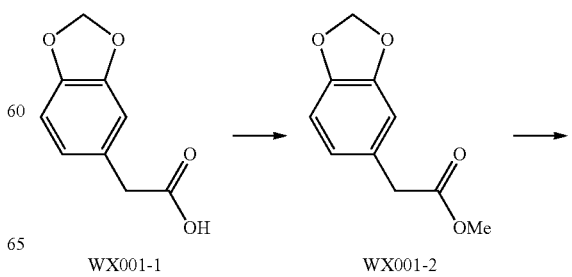

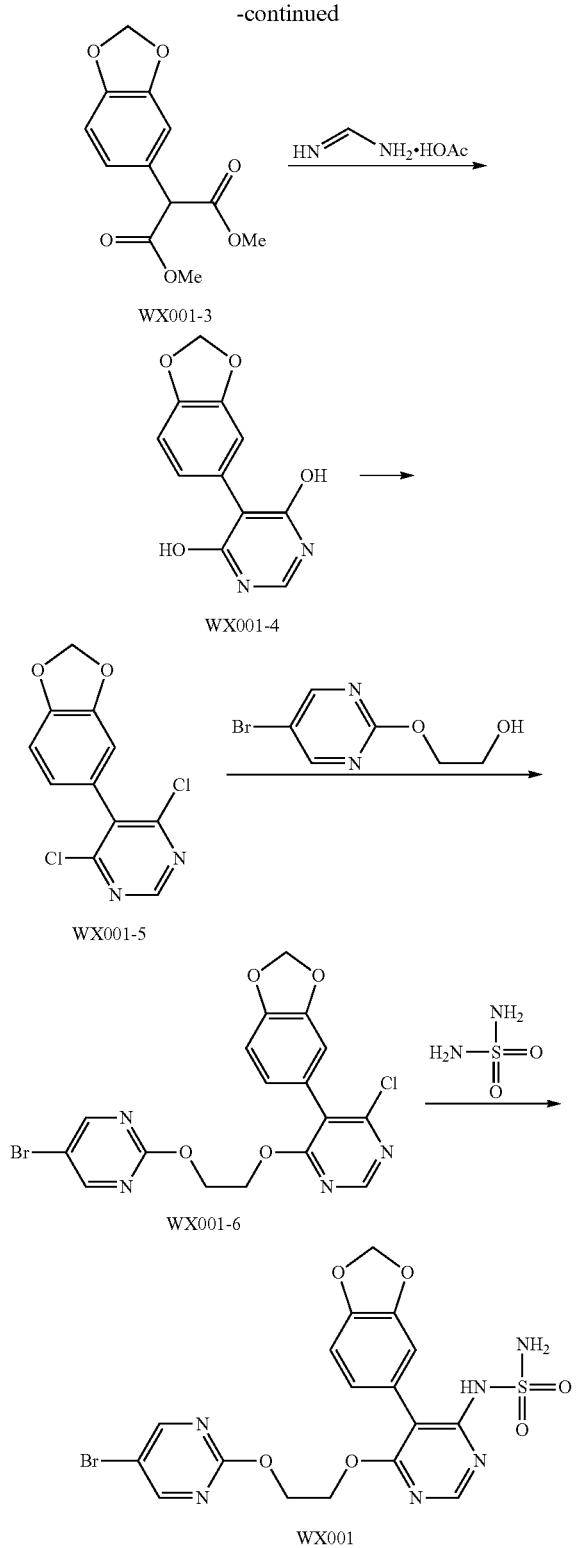

pleted, the solvent was removed under reduced pressure, and the residue was added with water (300 mL) and extracted with ethyl acetate (300 mL×3). The organic phases were combined, washed with saturated brine (300 mL), dried over anhydrous sodium sulfate, and filtered, and the solvent of filtrate was removed under reduced pressure to obtain compound WX001-2. $^1$H NMR (400 MHz, CDCl$_3$) δ: 6.80-6.71 (m, 3H), 5.94 (s, 2H), 3.70 (s, 3H), 3.55 (s, 2H).

Step 2: Synthesis of Compound WX001-3

At 0° C., a solution of the compound WX001-2 (35 g, 180.24 mmol) in dimethyl carbonate (118.51 g, 1.32 mol, 110.76 mL) was slowly added dropwise to a mixture solution of sodium hydride (10.81 g, 270.36 mmol, purity: 60%) in dimethyl carbonate (118.51 g, 1.32 mol, 110.76 mL) (dropping time is about 1 hour), the reaction mixture was warmed to room temperature and stirred for 15 hours under nitrogen atmosphere. After the reaction was completed, ice water (500 mL) was added and the mixture was extracted with ethyl acetate (300 mL×3). The organic phases were combined, washed with saturated brine (300 mL), dried over anhydrous sodium sulfate, filtered, and the solvent of filtrate was removed under reduced pressure. The residue was separated by column chromatography (eluent: petroleum ether/ethyl acetate=10/1-5/1, volume ratio) to obtain compound WX001-3. $^1$H NMR (400 MHz, CDCl$_3$) δ: 7.00-6.93 (m, 1H), 6.85-6.77 (m, 2H), 5.98 (s, 2H), 4.58 (s, 1H), 3.78 (s, 6H).

Step 3: Synthesis of Compound WX001-4

At 0° C., block of sodium (10.94 g, 475.78 mmol) was added portionwise to anhydrous methanol (150 mL), the reaction mixture was stirred at room temperature for 0.5 hour under nitrogen atmosphere, and then a solution of the compound WX001-3 (40 g, 158.59 mmol) in methanol (100 mL) was added to reaction solution. The reaction mixture was warmed to room temperature and stirred for 15 hours under nitrogen atmosphere, then the formamidine acetate (19.81 g, 190.31 mmol) was added to reaction solution in one portion, and the reaction mixture was further stirred at room temperature for 15 hours under nitrogen atmosphere. After the reaction was completed, the solvent was removed under reduced pressure, and the residue was added with 2 M diluted hydrochloric acid (200 mL), and stirred at room temperature for 30 minutes, during which a large amount of white solid was precipitated out. The reaction mixture was filtered, the filter cake was washed with methanol (50 mL×2), and the filter cake was collected and dried under vacuum to obtain compound WX001-4.

Step 4: Synthesis of Compound WX001-5

At room temperature, the compound WX001-4 (24 g, 103.36 mmol) was added to phosphorus oxychloride (594.00 g, 3.87 mol, 360.00 mL), and the reaction mixture was heated to 90° C. and stirred for 5 hours under nitrogen atmosphere. After the reaction was completed, the mixture was cooled to room temperature, the reaction solution was slowly poured into ice water (1000 mL), and stirred at room temperature for 0.5 hour, and then extracted with ethyl acetate (1000 mL×3). The organic phases were combined, washed with saturated brine (1000 mL), dried over anhydrous sodium sulfate, filtered, and the solvent of filtrate was removed under reduced pressure. The residue was separated by column chromatography (eluent: petroleum ether/ethyl acetate=10/1. volume ratio) to obtain compound WX001-5. $^1$H NMR (400 MHz, CDCl$_3$) δ: 8.78 (s, 1H), 6.96 (d, J=8.3 Hz, 1H), 6.78 (dd, J=2.5, 4.0 Hz, 2H), 6.09 (s, 2H).

Step 5: Synthesis of Compound WX001-6

At room temperature, compound 2-(5-bromopyrimidin-2-yl) oxyethanol (8.06 g, 36.79 mmol) and the compound Step 1: Synthesis of Compound WX001-2

At 0° C., dichlorosulfoxide (58.11 g, 488.46 mmol, 35.43 mL) was slowly added dropwise to a solution of compound WX001-1 (80 g, 444.06 mmol) in methanol (400 mL) (dropping time was about 0.5 hour), and the reaction mixture was warmed to room temperature and stirred for 10 hours under nitrogen atmosphere. After the reaction was com- WX001-5 (11 g, 40.88 mmol) were dissolved in toluene (100 mL), then the mixture was cooled to 0° C., potassium tert-butoxide (9.17 g, 81.76 mmol) was added in portions, and the reaction mixture was stirred at 0° C. for 0.5 hour under nitrogen atmosphere. After the reaction was completed, 0.5 M diluted hydrochloric acid (100 mL) was added to the reaction solution and the mixture was extracted with ethyl acetate (100 mL×3). The organic phases were combined, washed with saturated brine (100 mL), dried over anhydrous sodium sulfate, filtered, and the solvent of filtrate was removed under reduced pressure. The residue was separated by column chromatography (eluent: petroleum ether/ethyl acetate=5/1. volume ratio) to obtain compound WX001-6. $^1$H NMR (400 MHz, CDCl$_3$) δ: 8.54-8.48 (m, 3H), 6.86-6.74 (m, 3H), 6.02 (s, 2H), 4.80-4.74 (m, 2H), 4.73-4.64 (m, 2H).

Step 6: Synthesis of Compound WX001

At room temperature, compound sulfamide (1.52 g, 15.83 mmol) and the compound WX001-6 (6.5 g, 14.39 mmol) were dissolved in dimethyl sulfoxide (100 mL), and then potassium carbonate (5.97 g, 43.17 mmol) and tetrabutylammonium fluoride trihydrate (9.08 g, 28.78 mmol) were added in one portion. The reaction mixture was heated to 70° C. and stirred for 5 hours under nitrogen atmosphere. After the reaction was completed, the mixture was cooled to room temperature, added with 0.5 M diluted hydrochloric acid (100 mL) and water (500 mL), and extracted with ethyl acetate (400 mL×3). The organic phases were combined, washed with saturated brine (500 mL), dried over anhydrous sodium sulfate, filtered, and the solvent of filtrate was removed under reduced pressure. The residue was separated by column chromatography (eluent: petroleum ether/ethyl acetate=3/1, then dichloromethane/ethyl acetate=5/1, volume ratio) to obtain the target compound WX001. MS-ESI m/z: 510.8 [M+H]$^+$, 512.8 [M+H+2]$^+$. $^1$H NMR (400 MHz, DMSO_d$_6$) δ: 9.29 (s, 1H), 8.72 (s, 2H), 8.46 (s, 1H), 7.21 (s, 2H), 6.91 (d, J=7.8 Hz, 1H), 6.76-6.61 (m, 2H), 6.05 (s, 2H), 4.69-4.62 (m, 2H), 4.62-4.54 (m, 2H).

Embodiment 2: WX002

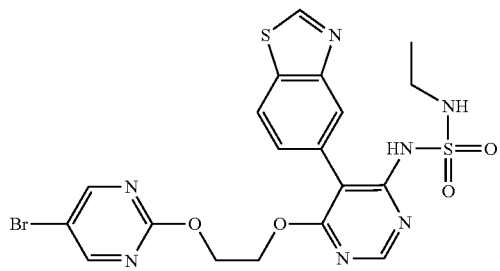 [SMILES: CCNS(=O)(=O)Nc1ncnc(OCCOc2ncc(Br)cn2)c1-c1ccc2scnc2c1]

Synthetic Route:

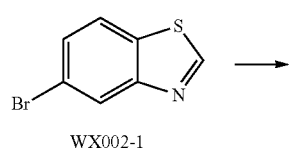

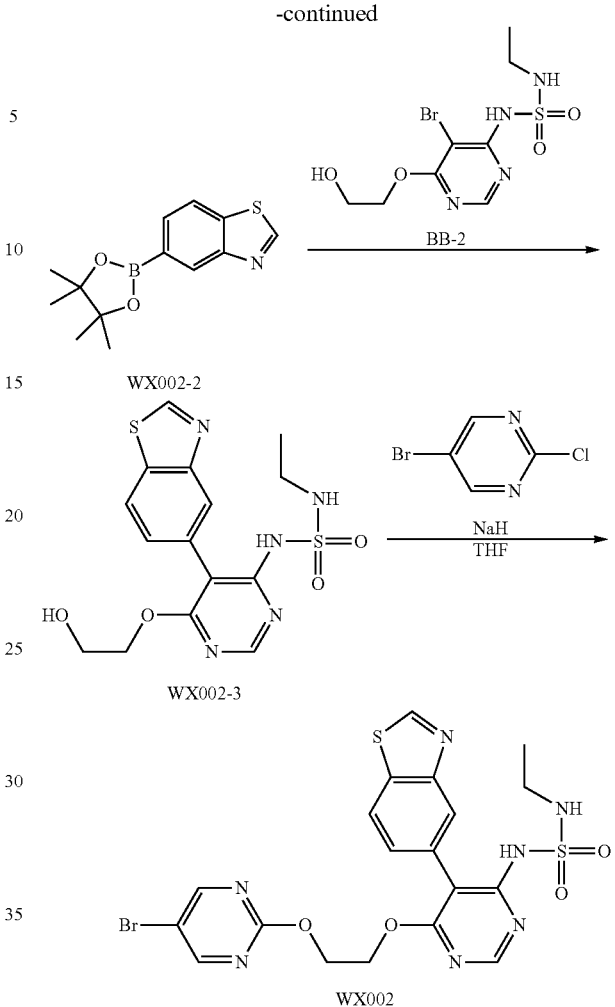

Step 1: Synthesis of Compound WX002-2

At room temperature, the compound WX002-1 (8.00 g, 37.37 mmol), bis(pinacolato) diboron (11.39 g, 44.84 mmol) and potassium acetate (7.33 g, 74.74 mmol) were added to 1,4-dioxane (100.00 mL), then [1,1'-bis(diphenylphosphino) ferrocene] dichloro-palladium(II) (5.47 g, 7.47 mmol) was added. The reaction mixture was heated to 100° C. and stirred for 10 hours under nitrogen atmosphere. After the reaction was completed, the mixture was cooled to room temperature, filtered, and the solvent of filtrate was removed under reduced pressure. The residue was added with water (100 mL) and extracted with ethyl acetate (100 mL×3). The organic phases were combined, washed with saturated brine (50 mL), dried over anhydrous sodium sulfate, filtered, and the solvent of filtrate was removed under reduced pressure. The residue was separated by column chromatography (eluent: petroleum ether/ethyl acetate=20/1. volume ratio) to obtain the target compound WX002-2. $^1$H NMR (400 MHz, CDCl$_3$) δ: 8.92 (s, 1H), 8.51 (s, 1H), 7.89 (d, J=8.0 Hz, 1H), 7.78 (d, J=8.0 Hz, 1H), 1.30 (s, 12H).

Step 2: Synthesis of Compound WX002-3

At room temperature, the compound BB-2 (250.00 mg, 732.75 μmol) and the compound WX002-2 (287.04 mg, 1.10 mmol) were added to 1,4-dioxane (15.00 mL), then a solution of potassium carbonate (303.82 mg, 2.20 mmol) in water (5.00 mL) was added. The reaction mixture was stirred at room temperature for 0.5 hour under nitrogen atmosphere, and then [1,1'-bis(diphenylphosphino) ferrocene] dichloropalladium(II) (160.85 mg, 219.83 μmol) was added to mixture. The reaction mixture was heated to 80° C. and stirred for 11 hours under nitrogen atmosphere. After the reaction was completed, the mixture was cooled to room temperature, added with water (100 mL), extracted with ethyl acetate (20 mL×1), and the organic phase was discard. The aqueous phase was adjusted to pH of 5-6 with 3 M dilute hydrochloric acid, and extracted with ethyl acetate (20 mL×3). The organic phases were combined, dried over anhydrous sodium sulfate, filtered, and the solvent of filtrate was removed under reduced pressure. The residue was separated by column chromatography (eluent: petroleum ether/ethyl acetate=10/1-1/1, volume ratio) to obtain target compound WX002-3. MS-ESI m/z: 395.9 [M+H]$^+$. $^1$H NMR (400 MHz, CDCl$_3$) δ: 9.01 (s, 1H), 8.47 (s, 1H), 8.05 (s, 1H), 8.02 (s, 1H), 7.31 (d, J=8.3 Hz, 1H), 7.06 (s, 1H), 5.52 (t, J=6.0 Hz, 1H), 4.44 (t, J=4.4 Hz, 2H), 3.77 (s, 2H), 3.08-2.98 (m, 2H), 2.58 (br s, 1H), 1.15 (t, J=7.2 Hz, 3H).

Step 3: Synthesis of Compound WX002

At room temperature, sodium hydride (194.20 mg, 4.86 mmol, purity: 60%) was added to anhydrous tetrahydrofuran (20.00 mL), then a solution of the compound WX002-3 (240.00 mg, 606.89 μmol) in anhydrous N,N-dimethylformamide (1 mL) and a solution of 5-bromo-2-chloropyrimidine (234.78 mg, 1.21 mmol) in anhydrous tetrahydrofuran (1 mL) were added, the reaction mixture was heated to 70° C. and stirred for 2 hours under nitrogen atmosphere. After the reaction was completed, the mixture was cooled to room temperature, added with saturated ammonium chloride solution (30 mL), adjusted to pH of 4-5 with 1 M dilute hydrochloric acid, and extracted with ethyl acetate (20 mL×3). The organic phases were combined, washed with saturated brine (50 mL), dried over anhydrous sodium sulfate, filtered, and the solvent of filtrate was removed under reduced pressure. The residue was separated by preparative HPLC (mobile phase: acetonitrile/water; basic system: NH$_4$HCO$_3$ and NH$_3$H$_2$O) to obtain the target compound WX002. MS-ESI m/z: 552.0 [M+H]$^+$, 554.0 [M+H+2]$^+$. $^1$H NMR (400 MHz, CDCl$_3$) δ: 9.08 (s, 1H), 8.52 (s, 1H), 8.43 (s, 2H), 8.04 (d, J=2.0 Hz, 2H), 7.34 (dd, J=8.5, 1.3 Hz, 1H), 6.87 (br s, 1H), 5.58 (s, 1H), 4.74 (t, J=4.4 Hz, 2H), 4.62 (t, J=4.4 Hz, 2H), 3.15-3.02 (m, 2H), 1.21 (t, J=7.3 Hz, 3H).

Referring to the synthesis method in embodiment 2 (BB-2 in step 2 was replaced with the corresponding structure in fragment 2), the embodiments in table 1 were synthesized.

TABLE 1

Embodiments 3-7 structural formula

| Embodiment | Fragment 1 | Fragment 2 | Fragment 3 | Structure | Compound |
|---|---|---|---|---|---|
| 3 | WX002-2 | BB-1 | Br–pyrimidine–Cl | (structure) | WX003 |
| 4 | WX002-2 | BB-7 | Br–pyrimidine–Cl | (structure) | WX004 |
| 5 | WX002-2 | BB-9 | Br–pyrimidine–Cl | (structure) | WX005 |
| 6 | WX002-2 | BB-6 | Br–pyrimidine–Cl | (structure) | WX006 |

TABLE 1-continued

Embodiments 3-7 structural formula

| Embodiment | Fragment 1 | Fragment 2 | Fragment 3 | Structure | Compound |
|---|---|---|---|---|---|
| 7 | 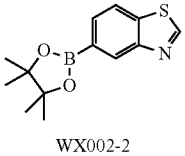 [SMILES: CC1(C)OB(c2ccc3scnc3c2)OC1(C)C] WX002-2 | 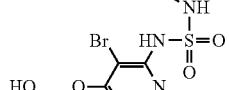 BB-11 | 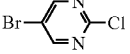 | 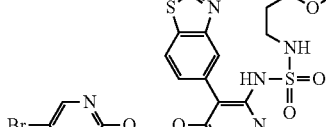 | WX007 |

The LCMS and HNMR data of each embodiment are shown in table 2.

TABLE 2

Embodiments 3-7 NMR and LCMS data

| Embodiment | Compound | $^1$HNMR | LCMS |
|---|---|---|---|
| 3 | WX003 | $^1$H NMR (400 MHz, CDCl$_3$) δ: 8.91 (s, 1H), 8.46 (s, 1H), 8.34 (s, 2H), 7.93-7.86 (m, 2H), 7.24 (dd, J = 8.4, 1.4 Hz, 1H), 6.29 (br s, 1H), 4.67 (d, J = 4.6 Hz, 2H), 4.54 (d, J = 4.6 Hz, 2H), 3.65 (q, J = 9.0 Hz, 2H). | MS-ESI m/z: 606.0 [M + H]$^+$, 608.0 [M + H + 2]$^+$. |
| 4 | WX004 | $^1$H NMR (400 MHz, CDCl$_3$) δ: 9.08 (br s, 1H), 8.52 (s, 1H), 8.43 (s, 2H), 8.12-7.91 (m, 2H), 7.34 (d, J = 8.3 Hz, 1H), 7.01 (br s, 1H), 5.61 (t, J = 5.0 Hz, 1H), 4.75 (br s, 2H), 4.62 (br s, 2H), 3.01 (d, J = 6.3 Hz, 2H), 1.55 (d, J = 7.3 Hz, 2H), 1.43-1.33 (m, 2H), 0.92 (t, J = 7.3 Hz, 3H). | MS-ESI m/z: 580.0 [M + H]$^+$, 582.0 [M + H + 2]$^+$. |
| 5 | WX005 | $^1$H NMR (400 MHz, CDCl$_3$) δ: 9.08 (s, 1H), 8.52 (s, 1H), 8.43 (s, 2H), 8.11-7.85 (m, 2H), 7.33 (d, J = 9.0 Hz, 1H), 5.75 (br s, 1H), 4.73 (d, J = 4.5 Hz, 2H), 4.64-4.56 (m, 2H), 2.88 (br s, 2H), 1.01 (br s, 1H), 0.54 (d, J = 7.8 Hz, 2H), 0.17 (br d, J = 5.0 Hz, 2H). | MS-ESI m/z: 578.0 [M + H]$^+$, 580.0 [M + H + 2]$^+$. |
| 6 | WX006 | $^1$H NMR (400 MHz, CDCl$_3$) δ: 9.00 (s, 1H), 8.44 (s, 1H), 8.36 (s, 2H), 8.02-7.92 (m, 2H), 7.30-7.23 (m, 1H), 6.96 (s, 1H), 6.06 (t, J = 5.7 Hz, 1H), 4.66 (d, J = 5.0 Hz, 2H), 4.57-4.51 (m, 2H), 3.48 (t, J = 5.0 Hz, 2H), 3.28 (t, J = 6.6 Hz, 2H), 3.11 (q, J = 5.5 Hz, 2H), 1.49-1.44 (m, 2H), 0.85 (t, J = 7,4 Hz, 3H). | MS-ESI m/z: 610.1 [M + H]$^+$, 612.1 [M + 2 + H]$^+$. |
| 7 | WX007 | $^1$H NMR (400 MHz, CDCl$_3$)δ: 9.04 (s, 1H), 8.52 (s, 1H), 8.42 (s, 2H), 8.10-7.84 (m, 2H), 7.34 (dd, J = 1.3, 8.3 Hz, 1H), 7.21 (br s, 1H), 6.09 (t, J = 6.0 Hz, 1H), 4.73 (d, J = 4.8 Hz, 2H), 4.65-4.57 (m, 2H), 3.46 (t, J = 5.6 Hz, 2H), 3.34 (s, 3H), 3.13 (q, J = 6.1 Hz, 2H), 1.84 (q, J = 6.0 Hz, 2H). | MS-ESI m/z: 595.9 [M + H]$^+$, 597.9 [M + H + 2]$^+$. |

Embodiment 8: WX008

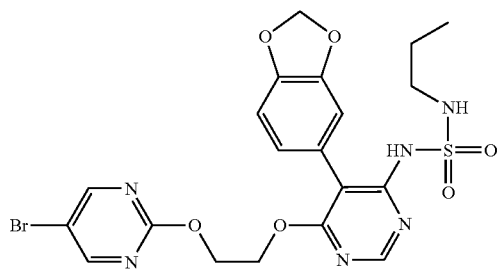 [SMILES: CCCNS(=O)(=O)Nc1ncnc(OCCOc2ncc(Br)cn2)c1-c1ccc2c(c1)OCO2]

Synthetic Route:

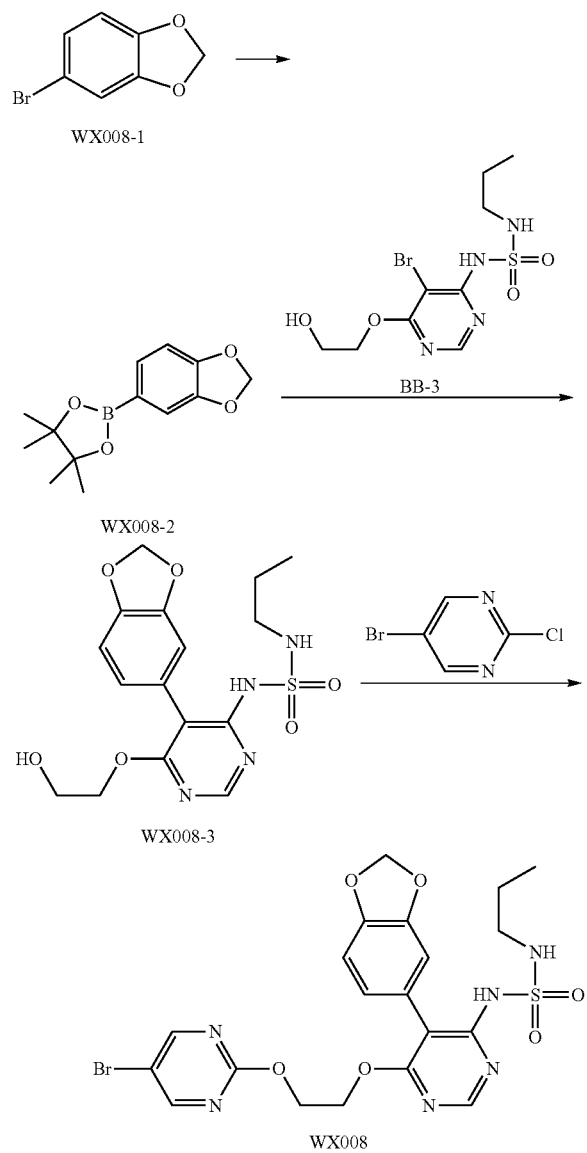

Step 1: Synthesis of Compound WX008-2

At room temperature, compound WX008-1 (3.00 g, 14.92 mmol), bis(pinacolato)diboron (7.58 g, 29.84 mmol) and potassium acetate (4.39 g, 44.76 mmol) were added to 1,4-dioxane (30.00 mL), then [1,1'-bis(diphenylphosphino) ferrocene] dichloropalladium (II) (3.28 g, 4.48 mmol) was added. The reaction mixture was heated to 80° C. and stirred for 16 hours under nitrogen atmosphere. After the reaction was completed, the mixture was cooled to room temperature, filtered, and the solvent of filtrate was removed under reduced pressure. The residue was added with water (30 mL) and extracted with ethyl acetate (20 mL×3). The organic phases were combined, dried over anhydrous sodium sulfate, filtrated, the solvent of filtrate was removed under reduced pressure, and the residue was separated by column chromatography (eluent: petroleum ether/ethyl acetate=1/0-100/1, volume ratio) to obtain the target compound WX008-2. $^1$H NMR (400 MHz, CDCl$_3$) δ:7.38 (dd, J=7.8, 0.8 Hz, 1H), 7.26 (s, 1H), 6.85 (d, J=7.8 Hz, 1H), 5.97 (s, 2H), 1.35 (s, 12H).

Step 2: Synthesis of Compound WX008-3

At room temperature, the compound BB-3 (300.00 mg, 844.57 μmol), the compound WX008-2 (419.04 mg, 1.69 mmol) and potassium phosphate (537.83 mg, 2.53 mmol) were added to N,N-dimethylformamide (20.00 mL), then [1,1'-bis(diphenylphosphino)ferrocene] dichloro-palladium (II) (185.39 mg, 253.37 μmol) was added. The reaction mixture was heated to 80° C. and stirred for 16 hours under nitrogen atmosphere. After the reaction was completed, the mixture was cooled to room temperature, added with water (100 mL), extracted with ethyl acetate (20 mL×1), and the organic phase was discard. The aqueous phase was adjusted to pH of 5-6 with 3 M dilute hydrochloric acid, and extracted with ethyl acetate (20 mL×3). The organic phases were combined, dried over anhydrous sodium sulfate, filtered, and the solvent of filtrate was removed under reduced pressure. The residue was separated by preparative chromatography plate (eluent: petroleum ether/ethyl acetate=1/2, volume ratio) to obtain the target compound WX008-3. MS-ESI m/z: 397.0 [M+H]$^+$.

Step 3: Synthesis of Compound WX008

At room temperature, sodium hydride (145.30 mg, 3.63 mmol, purity: 60%) was added to anhydrous tetrahydrofuran (20 mL), then a solution of the compound WX008-3 (180.00 mg, 454.06 μmol) in anhydrous N,N-dimethylformamide (1 mL) and a solution of 5-bromo-2-chloropyrimidine (175.66 mg, 908.13 μmol) in anhydrous tetrahydrofuran (1 mL) were added thereto. The reaction mixture was heated to 70° C. and stirred for 2 hours under nitrogen atmosphere. After the reaction was completed, the mixture was cooled to room temperature, added with saturated ammonium chloride solution (30 mL), adjusted to pH of 4-5 with 1 M dilute hydrochloric acid, and extracted with ethyl acetate (20 mL×3). The organic phases were combined, washed with saturated brine (50 mL), dried over anhydrous sodium sulfate, filtered, and the solvent of filtrate was removed under reduced pressure. The residue was separated by preparative HPLC (mobile phase: acetonitrile/water; neutral system) to obtain the target compound WX008. MS-ESI m/z: 552.8 [M+H]$^+$, 554.8 [M+H+2]$^+$. $^1$H NMR (400 MHz, CDCl$_3$) δ: 8.49 (s, 2H), 8.43 (s, 1H), 6.87 (d, J=8.3 Hz, 1H), 6.73-6.68 (m, 2H), 6.03 (s, 2H), 5.61 (t, J=6.2 Hz, 1H), 4.73 (q, J=5.0 Hz, 2H), 4.64 (t, J=4.8 Hz, 2H), 2.96 (q, J=6.8 Hz, 2H), 1.64-1.57 (m, 2H), 0.94 (t, J=7.4 Hz, 3H).

Referring to the synthesis method in embodiment 8 (BB-3 in step 2 was replaced with the corresponding structure in fragment 2), the embodiments in table 3 were synthesized.

TABLE 3

Embodiments 9-22 structural formula

| Embodiments | Fragment 1 | Fragment 2 | Fragment 3 | Structure | Compound |
|---|---|---|---|---|---|
| 9 | WX008-2 | BB-2 | Br-pyrimidine-Cl | 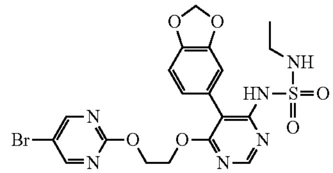 [SMILES: CCNS(=O)(=O)Nc1ncnc(OCCOc2ncc(Br)cn2)c1-c1ccc2c(c1)OCO2] | WX009 |
| 10 | WX008-2 | BB-1 | Br-pyrimidine-Cl | 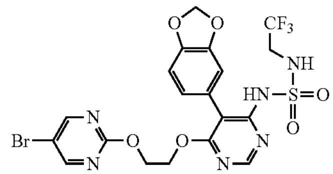 [SMILES: O=S(=O)(NCC(F)(F)F)Nc1ncnc(OCCOc2ncc(Br)cn2)c1-c1ccc2c(c1)OCO2] | WX010 |
| 11 | WX008-2 | BB-8 | Br-pyrimidine-Cl | 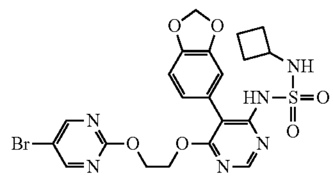 [SMILES: O=S(=O)(Nc1ncnc(OCCOc2ncc(Br)cn2)c1-c1ccc2c(c1)OCO2)NC1CCC1] | WX011 |
| 12 | WX008-2 | BB-7 | Br-pyrimidine-Cl | 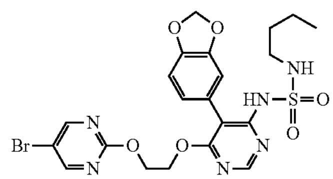 [SMILES: CCCCNS(=O)(=O)Nc1ncnc(OCCOc2ncc(Br)cn2)c1-c1ccc2c(c1)OCO2] | WX012 |
| 13 | WX008-2 | BB-4 | Br-pyrimidine-Cl | 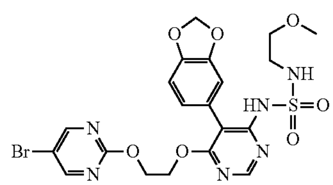 [SMILES: COCCNS(=O)(=O)Nc1ncnc(OCCOc2ncc(Br)cn2)c1-c1ccc2c(c1)OCO2] | WX013 |
| 14 | WX008-2 | BB-9 | Br-pyrimidine-Cl | 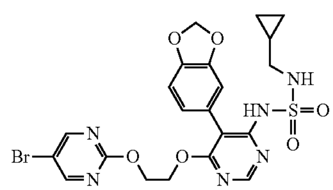 [SMILES: O=S(=O)(NCC1CC1)Nc1ncnc(OCCOc2ncc(Br)cn2)c1-c1ccc2c(c1)OCO2] | WX014 |
| 15 | WX008-2 | BB-5 | Br-pyrimidine-Cl | 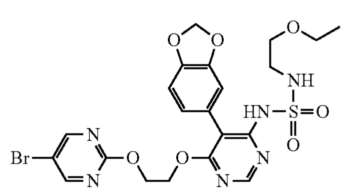 [SMILES: CCOCCNS(=O)(=O)Nc1ncnc(OCCOc2ncc(Br)cn2)c1-c1ccc2c(c1)OCO2] | WX015 |

TABLE 3-continued

Embodiments 9-22 structural formula

| Embodiments | Fragment 1 | Fragment 2 | Fragment 3 | Structure | Compound |
|---|---|---|---|---|---|
| 16 | WX008-2 | BB-6 | Br-pyrimidine-Cl | 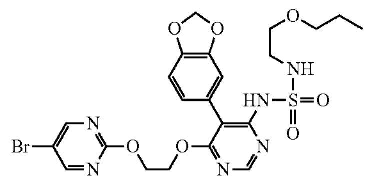 [SMILES: CCCOCCNS(=O)(=O)Nc1ncnc(OCCOc2ncc(Br)cn2)c1-c1ccc2c(c1)OCO2] | WX016 |
| 17 | WX008-2 | BB-11 | Br-pyrimidine-Cl | 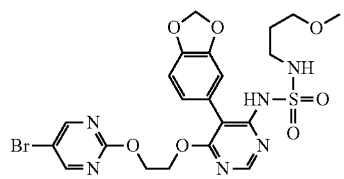 [SMILES: COCCCNS(=O)(=O)Nc1ncnc(OCCOc2ncc(Br)cn2)c1-c1ccc2c(c1)OCO2] | WX017 |
| 18 | WX008-2 | BB-12 | Br-pyrimidine-Cl | 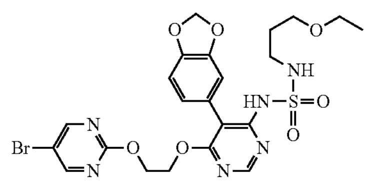 [SMILES: CCOCCCNS(=O)(=O)Nc1ncnc(OCCOc2ncc(Br)cn2)c1-c1ccc2c(c1)OCO2] | WX018 |
| 19 | WX008-2 | BB-14 | Br-pyrimidine-Cl | 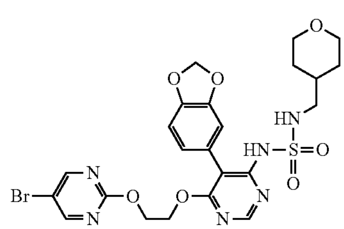 [SMILES: O=S(=O)(NCC1CCOCC1)Nc1ncnc(OCCOc2ncc(Br)cn2)c1-c1ccc2c(c1)OCO2] | WX019 |
| 20 | WX008-2 | BB-10 | Br-pyrimidine-Cl | 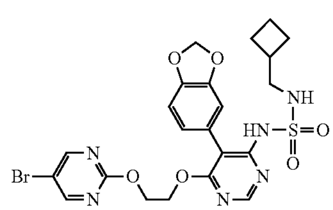 [SMILES: O=S(=O)(NCC1CCC1)Nc1ncnc(OCCOc2ncc(Br)cn2)c1-c1ccc2c(c1)OCO2] | WX020 |
| 21 | WX008-2 | BB-13 | Br-pyrimidine-Cl | 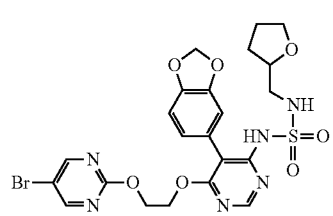 [SMILES: O=S(=O)(NCC1CCCO1)Nc1ncnc(OCCOc2ncc(Br)cn2)c1-c1ccc2c(c1)OCO2] | WX021 |

TABLE 3-continued

Embodiments 9-22 structural formula

| Embodiments | Fragment 1 | Fragment 2 | Fragment 3 | Structure | Compound |
|---|---|---|---|---|---|
| 22 | 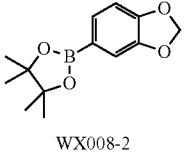 [SMILES: CC1(C)OB(c2ccc3c(c2)OCO3)OC1(C)C] WX008-2 | 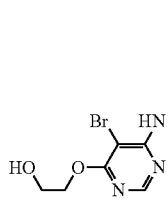 BB-15 | 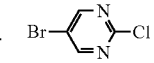 | 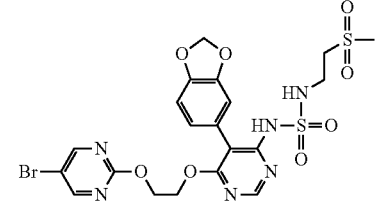 [SMILES: CS(=O)(=O)CCNS(=O)(=O)Nc1ncnc(OCCOc2ncc(Br)cn2)c1-c1ccc2c(c1)OCO2] | WX022 |

The LCMS and HNMR data of each embodiments are shown in table 4.

TABLE 4

Embodiments 9-22 NMR and LCMS data

| Embodiment | Compound | $^1$HNMR | LCMS |
|---|---|---|---|
| 9 | WX009 | $^1$H NMR (400 MHz, CDCl$_3$) δ: 8.49 (s, 2H), 8.44 (s, 1H), 7.00 (s, 1H), 6.87 (d, J = 8.3 Hz, 1H), 6.71 (d, J = 1.6 Hz, 1H), 6.70 (s, 1H), 6.03 (s, 2H), 5.56 (t, J = 6.0 Hz, 1H), 4.73 (t, J = 4.8 Hz, 2H), 4.64 (t, J = 4.8 Hz, 2H), 3.13-3.00 (m, 2H), 1.20 (t, J = 7.3 Hz, 3H). | MS-ESI m/z: 539.0 [M + H]$^+$, 541.0 [M + H + 2]$^+$. |
| 10 | WX010 | $^1$H NMR (400 MHz, CDCl$_3$) δ: 8.42 (s, 2H), 8.39 (s, 1H), 6.80 (d, J = 8.3 Hz, 1H), 6.62 (d, J = 1.2 Hz, 1H), 6.61 (d, J = 2.0 Hz, 1H), 5.97 (s, 2H), 4.67 (t, J = 4.8 Hz, 2H), 4.58 (t, J = 4.4 Hz, 2H), 3.61 (q, J = 8.8 Hz, 2H). | MS-ESI m/z: 593.0 [M + H]$^+$, 595.0 [M + H + 2]$^+$. |
| 11 | WX011 | $^1$H NMR (400 MHz, CDCl$_3$) δ: 8.50 (s, 2H), 8.49 (s, 1H), 7.01 (s, 1H), 6.87 (d, J = 8.5 Hz, 1H), 6.69-6.64 (m, 2H), 6.04 (s, 2H), 5.78 (d, J = 8.8 Hz, 1H), 4.72 (t, J = 4.5 Hz, 2H), 4.65 (t, J = 4.5 Hz, 2H), 3.89-3.83 (m, 1H), 2.28-2.19 (m, 2H), 1.90-1.85 (m, 2H), 1.74-1.60 (m, 2H). | MS-ESI m/z: 565.1 [M + H]$^+$, 567.1 [M + H + 2]$^+$. |
| 12 | WX012 | $^1$H NMR (400 MHz, CDCl$_3$) δ: 8.49 (s, 2H), 8.44 (s, 1H), 6.97 (br s, 1H), 6.87 (d, J = 8.0 Hz, 1H), 6.74-6.65 (m, 2H), 6.03 (s, 2H), 5.58 (t, J = 5.8 Hz, 1H), 4.72 (br s, 2H), 4.64 (br s, 2H), 2.99 (q, J = 6.8 Hz, 2H), 1.56-1.47 (m, 2H), 1.43-1.30 (m, 2H), 0.90 (t, J = 7.3 Hz, 3H). | MS-ESI m/z: 567.1 [M + H]$^+$, 569.1 [M + H + 2]$^+$. |
| 13 | WX013 | $^1$H NMR (400 MHz, CDCl$_3$) δ: 8.49 (s, 2H), 8.46 (s, 1H), 6.97 (s, 1H), 6.79 (d, J = 8.3 Hz, 1H), 6.68-6.43 (m, 2H), 6.02-5.91 (m, 3H), 4.71-4.61 (m, 2H), 4.60-4.52 (m, 2H), 3.42 (t, J = 5.0 Hz, 2H), 3.22 (s, 3H), 3.13-3.01 (m, 2H). | MS-ESI m/z: 569.0 [M + H]$^+$, 571.0 [M + H + 2]$^+$. |
| 14 | WX014 | $^1$H NMR (400 MHz, CDCl$_3$) δ: 8.49 (s, 2H), 8.45 (s, 1H), 6.97 (br s, 1H), 6.86 (d, J = 8.5 Hz, 1H), 6.78-6.58 (m, 2H), 6.03 (s, 2H), 5.73 (br s, 1H), 4.72 (t, J = 4.5 Hz, 2H), 4.65 (t, J = 4.5 Hz, 2H), 2.87 (t, J = 6.4 Hz, 2H), 0.99 (br s, 1H), 0.52 (d, J = 7.3 Hz, 2H), 0.16 (d, J = 4.5 Hz, 2H). | MS-ESI m/z: 565.0 [M + H]$^+$, 567.0 [M + H + 2]$^+$. |
| 15 | WX015 | $^1$H NMR (400 MHz, CDCl$_3$) δ: 8.42 (s, 2H), 8.37 (s, 1H), 6.79 (d, J = 8.5 Hz, 1H), 6.65-6.61 (m, 2H), 6.05 (br s, 1H), 5.95 (s, 2H), 4.68-4.61 (m, 2H), 4.59-4.52 (m, 2H), 3.46 (t, J = 5.0 | MS-ESI m/z: 583.1 [M + H]$^+$, 585.1 [M + H + 2]$^+$. |

TABLE 4-continued

Embodiments 9-22 NMR and LCMS data

| Embodiment | Compound | $^1$HNMR | LCMS |
|---|---|---|---|
| | | Hz, 2H), 3.36 (q, J = 7.0 Hz, 2H), 3.09 (t, J = 5.0 Hz, 2H), 1.09 (t, J = 7.0 Hz, 3H). | |
| 16 | WX016 | $^1$H NMR (400 MHz, CDCl$_3$) δ: 8.42 (s, 2H), 8.37 (s, 1H), 7.19 (s, 1H), 6.95 (br s, 1H), 6.79 (d, J = 8.3 Hz, 1H), 6.71-6.61 (m, 2H), 6.03 (t, J = 5.8 Hz, 1H), 5.96 (s, 2H), 4.64 (t, J = 4.8 Hz, 2H), 4.57 (t, J = 4.5 Hz, 2H), 3.54-3.42 (m, 2H), 3.36-3.23 (m, 2H), 3.16-3.04 (m, 2H), 1.51-1.42 (m, 2H), 0.95-0.77 (m, 3H). | MS-ESI m/z: 597.1 [M + H]$^+$, 599.1 [M + H + 2]$^+$. |
| 17 | WX017 | $^1$H NMR (400 MHz, CDCl$_3$) δ: 8.50 (s, 2H), 8.45 (s, 1H), 6.87 (d, J = 8.5 Hz, 1H), 6.74-6.69 (m, 2H), 6.06-6.00 (m, 3H), 4.77-4.69 (m, 2H), 4.67-4.62 (m, 2H), 3.46 (t, J = 5.6 Hz, 2H), 3.33 (s, 3H), 3.19-2.99 (m, 2H), 1.83 (q, J = 6.0 Hz, 2H). | MS-ESI m/z: 583.0 [M + H]$^+$, 585.0 [M + H + 2]$^+$. |
| 18 | WX018 | $^1$H NMR (400 MHz, CDCl$_3$) δ: 8.42 (s, 2H), 8.36 (s, 1H), 6.80 (d, J = 8.4 Hz, 1H), 6.70-6.59 (m, 2H), 5.96 (s, 2H), 4.65 (t, J = 4.4 Hz, 2H), 4.57 (t, J = 4.4 Hz, 2H), 3.44-3.36 (m, 4H), 3.05 (q, J = 6.0 Hz, 2H), 1.79-1.71 (m, 2H), 1.14 (t, J = 7.0 Hz, 3H). | MS-ESI m/z: 597.1 [M + H]$^+$, 599.1 [M + H + 2]$^+$. |
| 19 | WX019 | $^1$H NMR (400 MHz, CDCl$_3$) δ: 8.43 (s, 2H), 8.36 (s, 1H), 6.92 (br s, 1H), 6.80 (d, J = 8.5 Hz, 1H), 6.66-6.61 (m, 2H), 5.96 (s, 2H), 5.62 (t, J = 6.6 Hz, 1H), 4.66 (d, J = 4.7 Hz, 2H), 4.58 (d, J = 4.7 Hz, 2H), 3.91 (dd, J = 11.4, 3.26 Hz, 1H), 3.89 (dd, J = 11.4, 3.2 Hz, 1H), 3.30 (t, J = 11.4 Hz, 2H), 2.79 (t, J = 6.6 Hz, 2H), 1.73 (br s, 1H), 1.60 (d, J = 14.3 Hz, 2H), 1.30-1.16 (m, 2H). | MS-ESI m/z: 609.1 [M + H]$^+$, 611.1 [M + H + 2]$^+$. |
| 20 | WX020 | $^1$H NMR (400 MHz, CDCl$_3$) δ: 8.50 (s, 2H), 8.44 (s, 1H), 7.00 (s, 1H), 6.88 (d, J = 7.3 Hz, 1H), 6.72 (d, J = 7.6 Hz, 2H), 6.04 (s, 2H), 5.56 (t, J = 6.0 Hz, 1H), 4.76-4.70 (m, 2H), 4.69-4.62 (m, 2H), 3.00 (t, J = 6.8 Hz, 2H), 2.56-2.47 (m, 1H), 2.10-1.98 (m, 2H), 1.97-1.82 (m, 2H), 1.68 (br dd, J = 8.5, 11.0 Hz, 2H). | MS-ESI m/z: 579.0 [M + H]$^+$, 581.0 [M + H + 2]$^+$. |
| 21 | WX021 | $^1$H NMR (400 MHz, CDCl$_3$) δ: 8.50 (s, 2H), 8.46 (s, 1H), 7.02 (s, 1H), 6.87 (d, J = 8.3 Hz, 1H), 6.78-6.59 (m, 2H), 6.03 (s, 2H), 5.96 (br t, J = 6.3 Hz, 1H), 4.77-4.69 (m, 2H), 4.68-4.59 (m, 2H), 4.16-3.93 (m, 1H), 3.87-3.77 (m, 1H), 3.77-3.66 (m, 1H), 3.15 (m, 1H), 2.98 (td, J = 6.1, 12.3 Hz, 1H), 2.06-1.82 (m, 3H), 1.74-1.64 (m, 1H). | MS-ESI m/z: 595.0 [M + H]$^+$, 597.0 [M + H + 2]$^+$. |
| 22 | WX022 | $^1$H NMR (400 MHz, CDCl$_3$) δ: 8.50 (s, 2H), 8.46 (s, 1H), 7.05 (br s, 1H), 6.89 (d, J = 8.5 Hz, 1H), 6.76-6.67 (m, 2H), 6.33 (br s, 1H), 6.04 (s, 2H), 4.81-4.70 (m, 2H), 4.69-4.58 (m, 2H), 3.57 (q, J = 5.9 Hz, 2H), 3.34 (t, J = 5.9 Hz, 2H), 3.04 (s, 3H). | MS-ESI m/z: 616.7 [M + H]$^+$, 618.7 [M + H + 2]$^+$. |

Embodiment 23 and Embodiment 24: WX023 and WX024

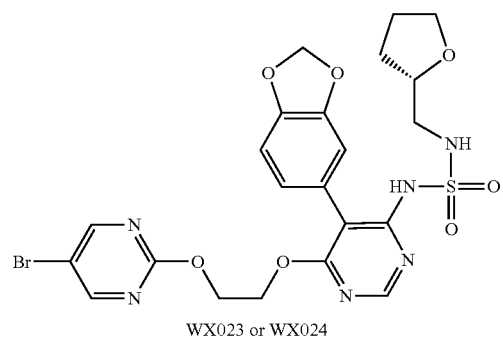
WX023 or WX024

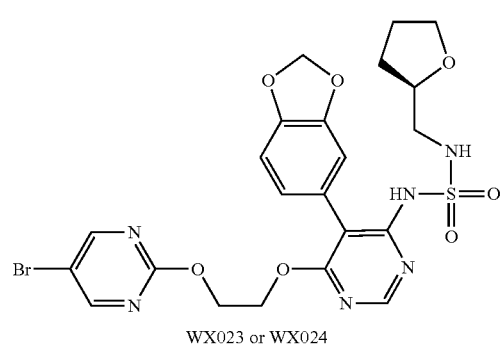
WX023 or WX024

Synthetic Route:

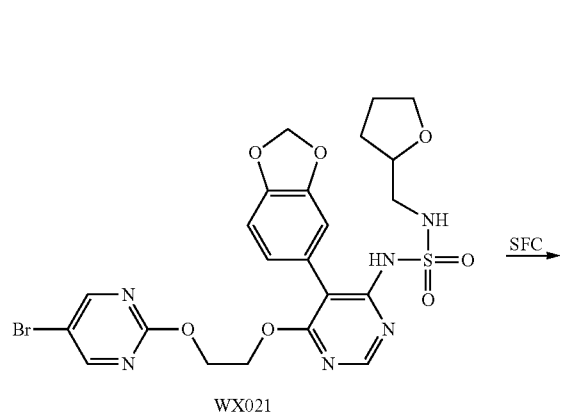

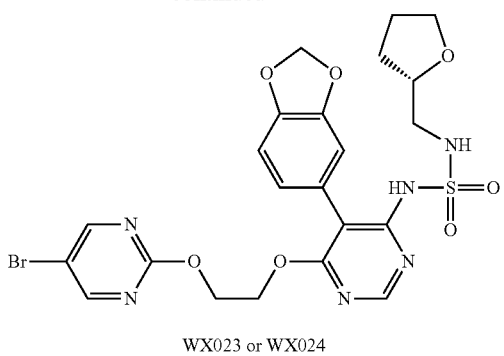
WX023 or WX024

Compound WX021 (500.00 mg, 839.74 μmol) was resolved by supercritical fluid chromatography (separation conditions, column: chiralpak AD-3 50*4.6 mm ID, 3 μm; mobile phase: A: carbon dioxide; B: isopropanol (0.05% diethylamine), 40%; column temperature: 40° C.; wavelength: 220 nm) to obtain the sample with a retention time of 1.149 min as WX023 (ee %: 100%) and the sample with a retention time of 3.199 min as WX024 (ee %: 100%).

Embodiment 25: WX025

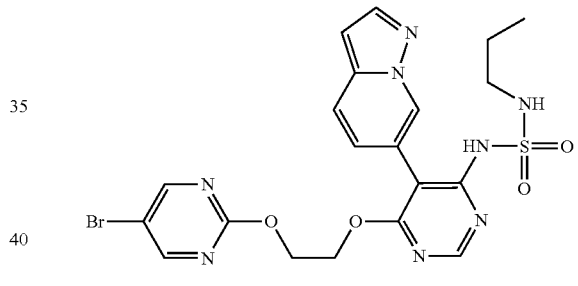

Synthetic Route:

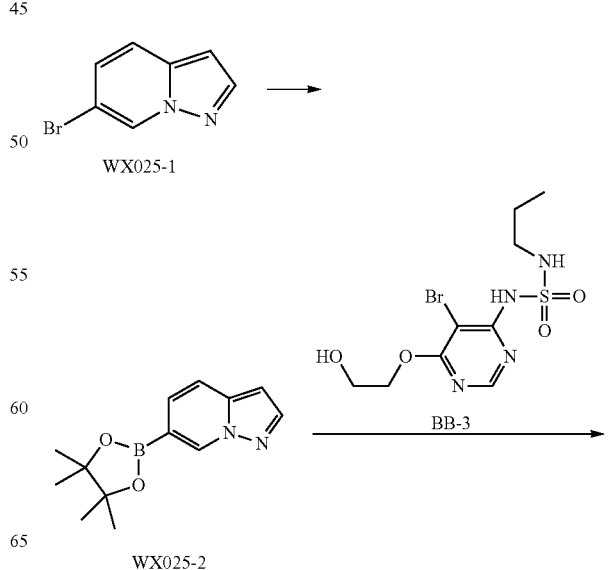

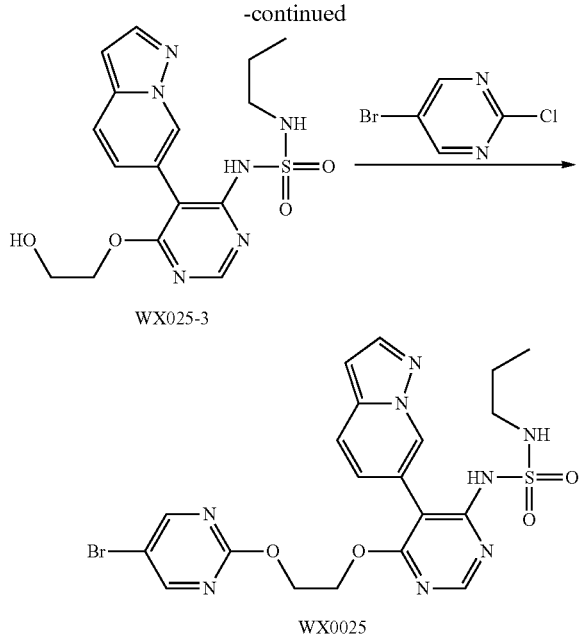

Step 1: Synthesis of Compound WX025-2

At room temperature, compound WX025-1 (400.00 mg, 2.03 mmol), bis(pinacolato) diboron (618.60 mg, 2.44 mmol), potassium acetate (597.72 mg, 6.09 mmol) and [1,1'-bis(diphenylphosphino)ferrocene]dichloropalladium (II) (297.09 mg, 406.03 μmol) were added to dioxane (20.00 mL), the reaction mixture was heated to 100° C. and stirred for 15 hours under nitrogen atmosphere. After the reaction was completed, the mixture was cooled to room temperature, the solvent was removed under reduced pressure, and the residue was added with water (100 mL) and extracted with ethyl acetate (100 mL×3). The organic phases were combined, washed with saturated brine (50 mL), dried over anhydrous sodium sulfate, filtered, and the solvent of filtrate was removed under reduced pressure. The residue was separated by column chromatography (eluent: petroleum ether/ethyl acetate=1/1. volume ratio) to obtain the target compound WX025-2. $^1$H NMR (400 MHz, CDCl$_3$) δ: 8.70 (s, 1H), 7.99-7.98 (m, 1H), 7.51 (d, J=8.8 Hz, 1H), 7.37 (d, J=8.8 Hz, 1H), 6.48 (s, 1H), 1.36 (s, 12H).

Step 2: Synthesis of Compound WX025-3

At room temperature, the compound BB-3 (300.00 mg, 844.57 μmol), the compound WX025-2 (309.24 mg, 1.27 mmol), [1,1'-bis(diphenylphosphino)ferrocene] dichloropalladium(II) (123.59 mg, 168.91 μmol) and potassium carbonate (350.18 mg, 2.53 mmol) were added to a mixture of dioxane (20.00 mL) and water (2.00 mL), and the reaction mixture was heated to 80° C. and stirred for 10 hours under nitrogen atmosphere. After the reaction was completed, the mixture was cooled to room temperature, added with water (100 mL), adjusted to pH of 5 with 1 M dilute hydrochloric acid, and extracted with ethyl acetate (50 mL×3). The organic phases were combined, washed with saturated brine (50 mL), dried over anhydrous sodium sulfate, filtered, and the solvent of filtrate was removed under reduced pressure. The residue was subjected to preparative chromatography (eluent: petroleum ether/ethyl acetate=1/2, volume ratio) to obtain the target compound WX025-3. MS-ESI m/z: 393.0 [M+H]$^+$.

Step 3: Synthesis of Compound WX025

At room temperature, a solution of the compound WX025-3 (180.00 mg, 346.76 μmol) in N,N-dimethylformamide (2 mL) and a solution of 5-bromo-2-chloropyrimidine (67.07 mg, 346.76 μmol) in tetrahydrofuran (1 mL) were added to a mixture of sodium hydride (83.08 mg, 2.08 mmol, purity: 60%) in anhydrous tetrahydrofuran (20 mL) in one portion. The reaction mixture was heated to 70° C. and stirred for 2 hours under nitrogen atmosphere. After the reaction was completed, the mixture was cooled to room temperature, added with saturated ammonium chloride solution (50 mL), adjusted to pH of 4-5 with 1 M dilute hydrochloric acid, and extracted with ethyl acetate (50 mL×3). The organic phases were combined, washed with saturated brine (50 mL), dried over anhydrous sodium sulfate, filtered, and the solvent of filtrate was removed under reduced pressure. The residue was separated by preparative HPLC (mobile phase: acetonitrile/water; basic system: NH$_4$HCO$_3$ and NH$_3$.H$_2$O) to obtain the target compound WX025. MS-ESI m/z: 549.0 [M+H]$^+$, 551.0 [M+H+2]$^+$. $^1$H NMR (400 MHz, CDCl$_3$) δ: 8.53 (s, 1H), 8.46-8.44 (m, 3H), 8.03 (s, 1H), 7.62 (d, J=9.2 Hz, 1H), 6.98 (d, J=9.2 Hz, 1H), 6.62 (s, 1H), 5.64 (s, 1H), 4.78-4.76 (m, 2H), 4.67-4.65 (m, 2H), 3.02-3.00 (m, 2H), 1.65-1.63 (m, 2H), 0.99 (t, J=7.2 Hz, 3H).

Referring to the synthesis method in embodiment 25 (BB-3 in step 2 was replaced with the corresponding structure in fragment 2), the embodiments in table 5 were synthesized.

TABLE 5

Embodiments 26-27 structural formula

| Embodiment | Fragment 1 | Fragment 2 | Fragment 3 | Structure | Compound |
|---|---|---|---|---|---|
| 26 | WX025-2 | BB-7 | Br-pyrimidine-Cl | (structure shown) | WX026 |

TABLE 5-continued

Embodiments 26-27 structural formula

| Embodiment | Fragment 1 | Fragment 2 | Fragment 3 | Structure | Compound |
|---|---|---|---|---|---|
| 27 | 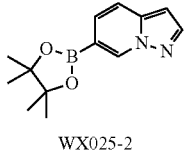 WX025-2 | 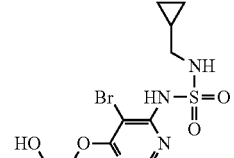 BB-9 | 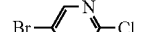 | 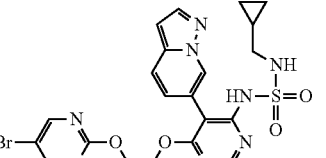 | WX027 |

The LCMS and HNMR data of each embodiments are shown in table 6.

TABLE 6

Embodiments 26-27 NMR and LCMS data

| Embodiment | Compound | $^1$HNMR | LCMS |
|---|---|---|---|
| 26 | WX026 | $^1$H NMR (400 MHz, CDCl$_3$) δ: 8.50 (s, 1H), 8.42 (d, J = 7.2 Hz, 3H), 8.00 (d, J = 2.2 Hz, 1H), 7.59 (d, J = 8.7 Hz, 1H), 6.94 (d, J = 9.0 Hz, 1H), 6.60 (d, J = 1.5 Hz, 1H), 5.59 (br s, 1H), 4.74 (t, J = 4.0 Hz, 2H), 4.63 (t, J = 4.8 Hz, 2H), 3.01 (d, J = 1.5 Hz, 2H), 1.52 (d, J = 6.8 Hz, 2H), 1.40-1.34 (m, 2H), 0.91 (t, J = 7.3, 3H). | MS-ESI m/z: 563.0 [M + H]$^+$, 565.0 [M + H + 2]$^+$. |
| 27 | WX027 | $^1$H NMR (400 MHz, CDCl$_3$) δ: 8.51 (s, 1H), 8.41 (s, 3H), 7.97 (d, J = 2.0 Hz, 1H), 7.56 (d, J = 9.0 Hz, 1H), 6.93 (d, J = 8.5 Hz, 1H), 6.57 (s, 1H), 4.78-4.67 (m, 2H), 4.65-4.57 (m, 2H), 2.89 (d, J = 7.0 Hz, 2H), 1.01 (br s, 1H), 0.69-0.40 (m, 2H), 0.29-0.16 (m, 2H). | MS-ESI m/z: 561.1 [M + H]$^+$, 563.1 [M + H + 2]$^+$. |

Embodiment 28: WX028

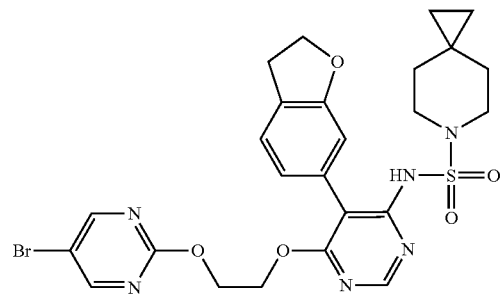 [SMILES: O=S(=O)(Nc1ncnc(OCCOc2ncc(Br)cn2)c1-c1ccc2c(c1)OCC2)N1CCC2(CC1)CC2]

Synthetic Route:

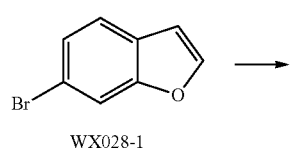

WX028-1

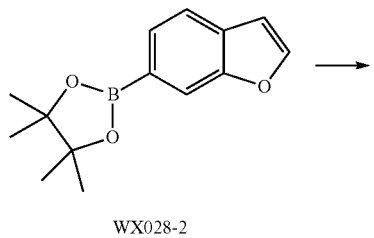

WX028-2

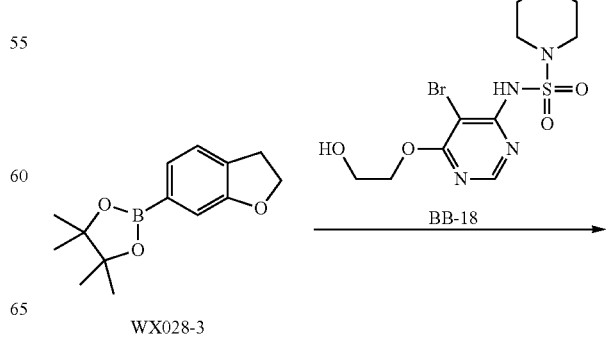

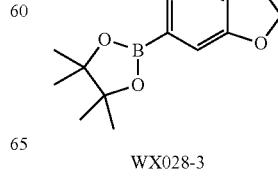

WX028-3

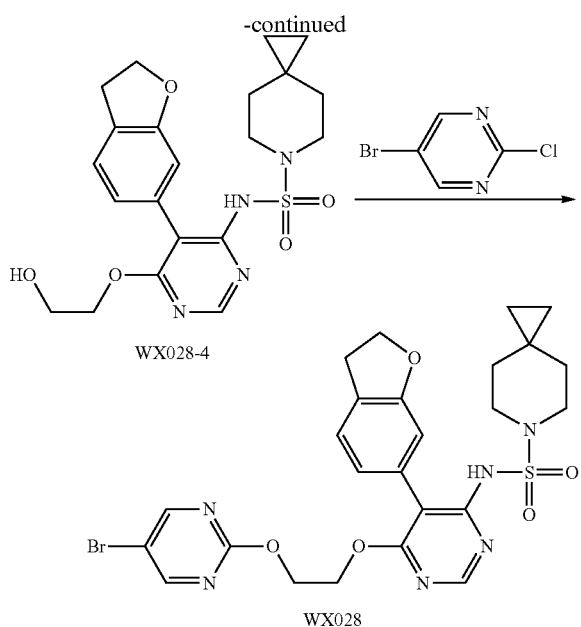

WX028-4

WX028

Step 1: Synthesis of Compound WX028-2

At room temperature, compound WX028-1 (2.00 g, 10.15 mmol), bis(pinacolato)diboron (3.87 g, 15.23 mmol) and potassium acetate (2.99 g, 30.45 mmol) were added to acetonitrile (30.00 mL), then [1,1'-bis(diphenylphosphino)ferrocene]dichloropalladium (II) (1.11 g, 1.52 mmol) was added. The reaction mixture was heated to 60° C. and stirred for 16 hours under nitrogen atmosphere. After the reaction was completed, the mixture was cooled to room temperature and the solvent was removed under reduced pressure. The residue was added with water (20 mL), and extracted with ethyl acetate (20 mL×3). The organic phases were combined, washed with saturated brine (80 mL), dried over anhydrous sodium sulfate, filtered, and the solvent of filtrate was removed under reduced pressure. The residue was separated by preparative chromatography (eluent: petroleum ether) to obtain the target compound WX028-2. $^1$H NMR (400 MHz, CDCl$_3$) δ: 7.99 (s, 1H), 7.72-7.69 (m, 1H), 7.69 (d, J=2.0 Hz, 1H), 7.64-7.61 (m, 1H), 6.80 (d, J=1.2 Hz, 1H), 1.39 (s, 12H).

Step 2: Synthesis of Compound WX028-3

At room temperature, wet palladium carbon (50.00 mg, purity: 10%) was added to a solution of the compound WX028-2 (1.50 g, 6.15 mmol) in methanol (30.00 mL), and the reaction mixture was stirred for 16 hours at room temperature under hydrogen (15 psi) atmosphere. After the reaction was completed, the reaction mixture was filtered, and the solvent of filtrate was removed under reduced pressure to obtain the target compound WX028-3. $^1$H NMR (400 MHz, CDCl$_3$) δ: 7.32 (d, J=7.0 Hz, 1H), 7.21 (m, 2H), 4.55 (t, J=8.5 Hz, 2H), 3.22 (t, J=8.5 Hz, 2H), 1.34 (s, 12H).

Step 3: Synthesis of Compound WX028-4

At room temperature, a solution of potassium carbonate (254.51 mg, 1.84 mmol) in water (2.00 mL) and [(bis(1-adamantyl)-N-n-butylphosphine]-2-(2-amino-biphenyl)dichloropalladium (40.00 mg) were added to a solution of the compound BB-18 (250.00 mg, 613.83 μmol) and the compound WX028-3 (226.60 mg, 920.74 μmol) in dioxane (20.00 mL). The reaction mixture was heated to 60° C. and stirred for 16 hours under nitrogen atmosphere. After the reaction was completed, the mixture was cooled to room temperature, and the solvent was removed under reduced pressure. Then the mixture was added with water (15 mL), adjusted to pH of 4-5 with 1 M dilute hydrochloric acid, and extracted with ethyl acetate (20 mL×3). The organic phases were combined, washed with saturated brine (60 mL), dried over anhydrous sodium sulfate, filtered, and the solvent of filtrate was removed under reduced pressure. The residue was separated by preparative chromatography (eluent: petroleum ether/ethyl acetate=1/1, volume ratio) to obtain the target compound WX028-4. MS-ESI m/z: 447.2 [M+H]$^+$.

Step 4: Synthesis of Compound WX028

At room temperature, a solution of the compound WX028-4 (220.00 mg, 492.70 μmol) in N,N-dimethylformamide and 5-bromo-2-chloropyrimidine (190.61 mg, 985.40 μmol) were added to a mixture of sodium hydride (300.00 mg, 7.50 mmol, purity: 60%) in anhydrous tetrahydrofuran (15.00 mL) in one portion. The reaction mixture was heated to 75° C. and stirred for 1.5 hours under nitrogen atmosphere. After the reaction was completed, the solution was cooled to room temperature, added with saturated ammonium chloride solution (20 mL), adjusted to pH of 4-5 with 1 M dilute hydrochloric acid, and extracted with ethyl acetate (30 mL×3). The organic phases were combined, washed with saturated brine (100 mL), dried over anhydrous sodium sulfate, filtered, and the solvent of filtrate was removed under reduced pressure. The residue was separated by preparative chromatography (eluent: petroleum ether/ethyl acetate=1/1, volume ratio) to obtain the target compound WX028. MS-ESI m/z: 603.1 [M+H]$^+$, 605.1 [M+H+2]$^+$. $^1$H NMR (400 MHz, CDCl$_3$) δ: 8.48 (s, 2H), 8.46 (s, 1H), 7.23 (d, J=7.5 Hz, 1H), 6.99 (s, 1H), 6.69 (d, J=7.5 Hz, 1H), 6.63 (s, 1H), 4.74-4.70 (m, 2H), 4.66-4.64 (m, 2H), 4.63-4.59 (m, 2H), 3.49-3.44 (m, 4H), 3.25 (t, J=8.5 Hz, 2H), 1.48-1.44 (m, 4H), 0.34 (s, 4H).

Referring to the synthesis method in embodiment 28 (BB-18 in step 3 was replaced with the corresponding structure in fragment 2), the embodiments in table 7 were synthesized.

TABLE 7

Embodiments 29-32 structural formula

| Embodiment | Fragment 1 | Fragment 2 | Fragment 3 | Structure | Compound |
|---|---|---|---|---|---|
| 29 | WX028-3 | BB-3 | Br-pyrimidine-Cl | 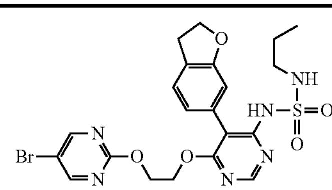 | WX029 |

TABLE 7-continued

Embodiments 29-32 structural formula

| Embodiment | Fragment 1 | Fragment 2 | Fragment 3 | Structure | Compound |
|---|---|---|---|---|---|
| 30 | 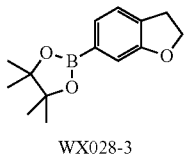 [SMILES: CC1(C)OB(c2ccc3c(c2)OCC3)OC1(C)C]<br>WX028-3 | 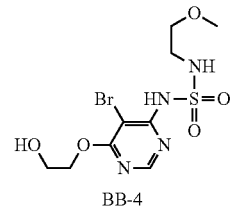<br>BB-4 | 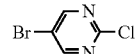 | 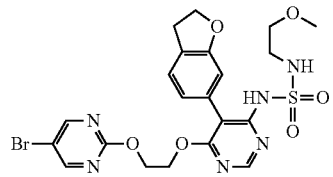 [SMILES: COCCNS(=O)(=O)Nc1ncnc(OCCOc2ncc(Br)cn2)c1-c1ccc2c(c1)OCC2] | WX030 |
| 31 | 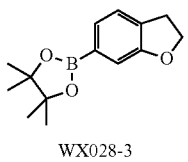 [SMILES: CC1(C)OB(c2ccc3c(c2)OCC3)OC1(C)C]<br>WX028-3 | 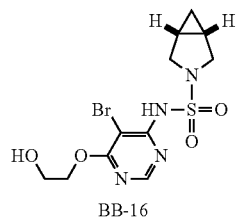<br>BB-16 | 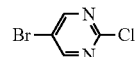 | 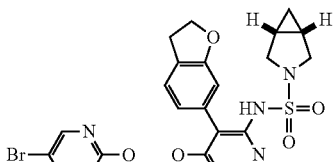 | WX031 |
| 32 | 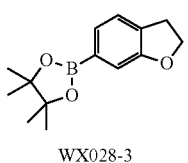<br>WX028-3 | 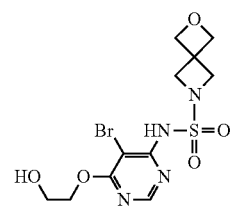<br>BB-17 | 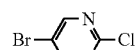 | 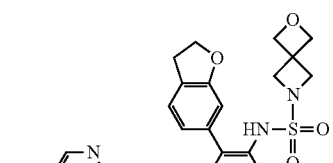 | WX032 |

The LCMS and HNMR data of each embodiments are shown in table 8.

TABLE 8

Embodiments 29-32 NMR and LCMS data

| Embodiment | Compound | ¹HNMR | LCMS |
|---|---|---|---|
| 29 | WX029 | ¹H NMR (400 MHz, DMSO-$d_6$) δ: 9.19 (s, 1H), 8.71 (s, 2H), 8.47 (s, 1H), 7.29 (t, J = 5.9 Hz, 1H), 7.21 (d, J = 7.5 Hz, 1H), 6.64 (dd, J = 1.3, 7.5 Hz, 1H), 6.56 (s, 1H), 4.69-4.61 (m, 2H), 4.61-4.48 (m, 4H), 3.20 (t, J = 8.7 Hz, 2H), 2.80 (q, J = 6.7 Hz, 2H), 1.42 (m, 2H), 0.80 (t, J = 7.4 Hz, 3H). | MS-ESI m/z: 551.1 [M + H]⁺, 553.1 [M + H + 2]⁺. |
| 30 | WX030 | ¹H NMR (400 MHz, DMSO-$d_6$) δ: 9.32 (br s, 1H), 8.72 (s, 2H), 8.47 (br s, 1H), 7.22-7.20 (m, 2H), 6.65 (d, J = 6.5 Hz, 1H), 6.58 (s, 1H), 4.65 (t, J = 3.0 Hz, 2H), 4.61-4.52 (m, 4H), 3.36 (br s, 2H), 3.25-3.16 (m, 2H), 3.13 (s, 3H), 3.03 (t, J = 4.8 Hz, 2H). | MS-ESI m/z: 567.0 [M + H]⁺, 569.0 [M + H + 2]⁺. |
| 31 | WX031 | ¹H NMR (400 MHz, CDCl₃) δ: 8.47 (br s, 3H), 7.21 (d, J = 7.0 Hz, 1H), 7.00 (br s, 1H), 6.68 (d, J = 7.5 Hz, 1H), 6.62 (s, 1H), 4.70 (d, J = 2.5 Hz, 2H), 4.66-4.57 (m, 4H), 3.64 (br s, 4H), 3.24 (t, J = 8.3 Hz, 2H), 1.52 (br s, 2H), 0.65 (q, J = 6.5 Hz, 1H), 0.35 (br s, 1H). | MS-ESI m/z: 574.8 [M + H]⁺, 576.8 [M + H + 2]⁺. |

TABLE 8-continued

Embodiments 29-32 NMR and LCMS data

| Embodiment | Compound | ¹HNMR | LCMS |
|---|---|---|---|
| 32 | WX032 | ¹H NMR (400 MHz, CDCl₃) δ: 8.51 (s, 2H), 8.46 (s, 1H), 7.25 (d, J = 7.3 Hz, 1H), 6.73 (d, J = 7.3 Hz, 1H), 6.68 (br s, 1H), 4.77 (br s, 4H), 4.76-4.72 (m, 2H), 4.66 (t, J = 8.4 Hz, 2H), 4.65-4.57 (m, 2H), 4.39 (br s, 4H), 3.27 (t, J = 8.4 Hz, 2H). | MS-ESI m/z: 590.8 [M + H]⁺, 592.8 [M + H + 2]⁺. |

Embodiment 33: WX033

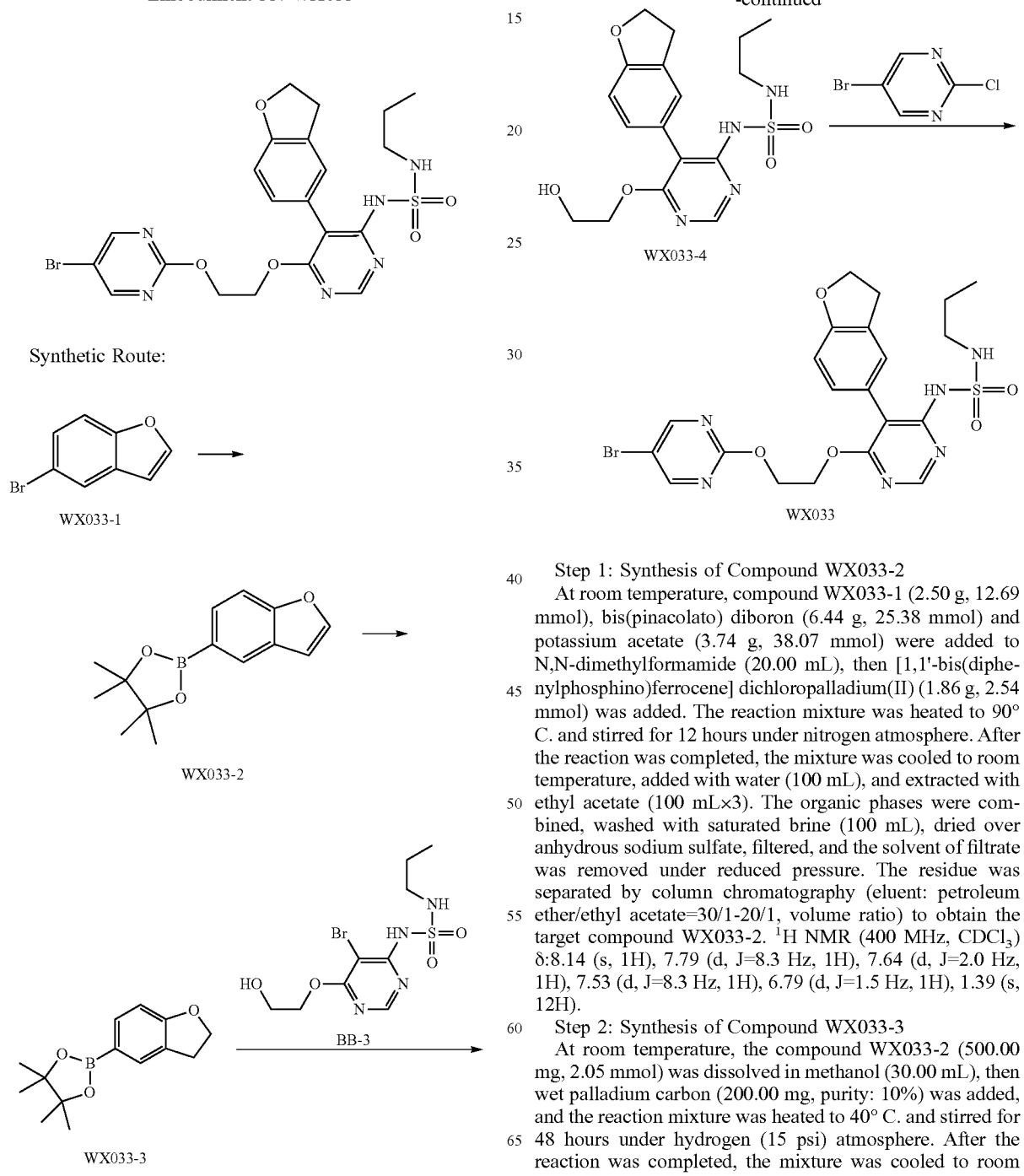

Synthetic Route:

Step 1: Synthesis of Compound WX033-2

At room temperature, compound WX033-1 (2.50 g, 12.69 mmol), bis(pinacolato) diboron (6.44 g, 25.38 mmol) and potassium acetate (3.74 g, 38.07 mmol) were added to N,N-dimethylformamide (20.00 mL), then [1,1'-bis(diphenylphosphino)ferrocene] dichloropalladium(II) (1.86 g, 2.54 mmol) was added. The reaction mixture was heated to 90° C. and stirred for 12 hours under nitrogen atmosphere. After the reaction was completed, the mixture was cooled to room temperature, added with water (100 mL), and extracted with ethyl acetate (100 mL×3). The organic phases were combined, washed with saturated brine (100 mL), dried over anhydrous sodium sulfate, filtered, and the solvent of filtrate was removed under reduced pressure. The residue was separated by column chromatography (eluent: petroleum ether/ethyl acetate=30/1-20/1, volume ratio) to obtain the target compound WX033-2. ¹H NMR (400 MHz, CDCl₃) δ:8.14 (s, 1H), 7.79 (d, J=8.3 Hz, 1H), 7.64 (d, J=2.0 Hz, 1H), 7.53 (d, J=8.3 Hz, 1H), 6.79 (d, J=1.5 Hz, 1H), 1.39 (s, 12H).

Step 2: Synthesis of Compound WX033-3

At room temperature, the compound WX033-2 (500.00 mg, 2.05 mmol) was dissolved in methanol (30.00 mL), then wet palladium carbon (200.00 mg, purity: 10%) was added, and the reaction mixture was heated to 40° C. and stirred for 48 hours under hydrogen (15 psi) atmosphere. After the reaction was completed, the mixture was cooled to room temperature, filtered through diatomite, and the solvent of filtrate was removed under reduced pressure to obtain the target compound WX033-3. $^1$H NMR (400 MHz, CDCl$_3$) δ: 7.62 (s, 1H), 7.60-7.50 (m, 1H), 6.78-6.77 (m, 1H), 4.60-4.56 (t, J=8.8 Hz, 2H), 3.22-3.17 (t, J=8.8 Hz, 2H), 1.33 (s, 12H).

Step 3: Synthesis of Compound WX033-4

At room temperature, the compound BB-3 (500.00 mg, 703.81 μmol), the compound WX033-3 (259.82 mg, crude product), potassium carbonate (291.82 mg, 2.11 mmol) and [1,1'-bis(diphenylphosphino)ferrocene]dichloropalladium (II) (103.00 mg, 140.76 μmol) were added to a mixture of dioxane (20.00 mL) and water (2.00 mL). The reaction mixture was heated to 80° C. and stirred for 10 hours under nitrogen atmosphere. After the reaction was completed, the mixture was cooled to room temperature, and the solvent was removed under reduced pressure. The residue was added with water (100 mL), adjusted to pH of 5 with 1M dilute hydrochloric acid, and extracted with ethyl acetate (50 mL×3). The organic phases were combined, washed with saturated brine (50 mL), dried over anhydrous sodium sulfate, filtered, and the solvent of filtrate was removed under reduced pressure. The residue was separated by preparative chromatography (eluent: petroleum ether/ethyl acetate=1/1, volume ratio) to obtain the target compound WX033-4. MS-ESI m/z: 395.0 [M+H]t Step 4: Synthesis of Compound WX033

At room temperature, a solution of the compound WX033-4 (140.00 mg, 314.28 μmol) in N,N-dimethylformamide (2.00 mL) and a solution of 5-bromo-2-chloropyrimidine (121.58 mg, 628.56 μmol) in tetrahydrofuran (1 mL) were sequentially added to a solution of sodium hydride (75.43 mg, 1.89 mmol, purity: 60%) in anhydrous tetrahydrofuran (20.00 mL) in one portion. The reaction mixture was heated to 70° C. and stirred for 2 hours under nitrogen atmosphere. After the reaction was completed, the mixture was cooled to room temperature, added with saturated ammonium chloride aqueous solution (50 mL), adjusted to pH of 4-5 with 1M dilute hydrochloric acid, and extracted with ethyl acetate (50 mL×3). The organic phases were combined, washed with saturated brine (50 mL), dried over anhydrous sodium sulfate, filtered, and the solvent of filtrate was removed under reduced pressure. The residue was separated by preparative chromatography (eluent: petroleum ether/ethyl acetate=1/1, volume ratio) to obtain the target compound WX033. MS-ESI m/z: 551.1 [M+H]$^+$, 553.1 [M+H+2]$^+$. $^1$H NMR (400 MHz, CDCl$_3$) δ: 8.50 (s, 2H), 8.43 (s, 1H), 7.07 (s, 1H), 7.01-6.97 (m, 2H), 6.83-6.78 (m, 1H), 5.65 (s, 1H), 4.73-4.71 (m, 2H), 4.65-4.61 (m, 4H), 3.25-3.20 (m, 2H), 2.98-2.93 (m, 2H), 1.60-1.56 (m, 2H), 0.96 (t, J=7.6 Hz, 3H).

Referring to the synthesis method in embodiment 33 (BB-3 in step 3 was replaced with fragment 2), the embodiment in table 9 were synthesized.

TABLE 9

Embodiment 34 structural formula

| Embodiment | Fragment 1 | Fragment 2 | Fragment 3 | Structure | Compound |
|---|---|---|---|---|---|
| 34 | 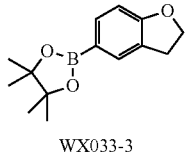 [SMILES: CC1(C)OB(c2ccc3c(c2)CCO3)OC1(C)C] WX033-3 | 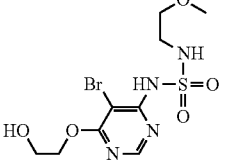 BB-4 | 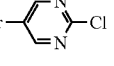 | 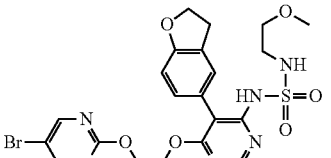 | WX034 |

The LCMS and HNMR data of embodiment are shown in table 10.

TABLE 10

Embodiment 34 NMR and LCMS data

| Embodiment | Compound | HNMR | LCMS |
|---|---|---|---|
| 34 | WX034 | $^1$H NMR (400 MHz, CDCl$_3$) δ: 8.50 (s, 2H), 8.46 (s, 1H), 7.11-6.95 (m, 3H), 6.86-6.80 (m, 1H), 6.07 (t, J = 5.8 Hz, 1H), 4.76-4.70 (m, 2H), 4.67-4.60 (m, 4H), 3.50 (t, J = 5.0 Hz, 2H), 3.30 (s, 3H), 3.24 (t, J = 8.8 Hz, 2H), 3.18 (q, J = 5.1 Hz, 2H). | MS-ESI m/z: 567.0 [M + H]$^+$, 569.0 [M + H + 2]$^+$. |

Experimental Embodiment 1: In Vitro Test of Antagonistic Effect Against Human ET$_A$ Receptor Experimental Purpose:

Antagonistic activity of the compounds against endogenously expressed human ET$_A$ receptors in SK-N-MC cells was evaluated by measuring the effect of compounds on the changes in cytoplasmic Ca$^{2+}$ ion signal induced by human ET$_A$ receptor agonists using fluorescence detection methods. The functional activity of the ET$_A$ receptor antagonistic effect was tested in Eurofins-Cerep SA according to current standard procedures.

Experimental Protocol:

1. Cells were suspended in Dulbecco's modified Eagle medium solution (DMEM, Invitrogen) supplemented with 1% FCSd, then distributed in 384-well plate (100 μL/well) at a density of 5×10⁴ cells/well;

2. Probenecid in Hank's balanced salt solution (HBSS, Invitrogen) supplemented with 20 mM 4-(2-hydroxyethyl)piperazine-1-ethanesulfonic acid (Hepes, Invitrogen) (pH 7.4) was mixed with fluorescent probe (Fluo4 NW, Invitrogen), the mixture was added to each wells, then balanced with cells at 37° C. for 60 minutes, and then balanced with cells at 22° C. for 15 minutes;

3. The test plate was placed in a microplate reader (CellLux, PerkinElmer), a DMSO solution or HBSS buffer with an appropriate concentration of the test compound and the positive control was added, and 1 nM endothelin-1 or HBSS buffer (base control) was added after 5 minutes, and then the change in fluorescence intensity proportional to the concentration of $Ca^{2+}$ ions of free cell lysosomes was measured;

4. Results were shown as the percent inhibition of control response to 1 nM endothelin-1;

5. Standard positive control was BQ-123, several concentrations were tested in each experiments. The data was analyzed using Prism to generate a concentration-response curve, and $IC_{50}$ values of the compounds were calculated.

Experimental Embodiment 2: In Vitro Test of Antagonistic Effects Against Human $ET_A$ Receptor Experimental Purpose:

Antagonist activity of the compound against human $ET_B$ receptors expressed in transfected CHO cells was evaluated by measuring the effect of the compound on the changes in the cytoplasmic $Ca^{2+}$ ion signal induced by human $ET_B$ receptor agonists. The functional activity of the $ET_B$ receptor antagonistic effect was tested in Eurofins-Cerep SA according to current standard procedures.

Experimental Protocol:

1. Cells were suspended in DMEM buffer (Invitrogen) and then distributed in 384-well plate (100 μL/well) at a density of 3×10⁴ cells/well;

2. Probenecid in HBSS buffer (Invitrogen) supplemented with 20 mM Hepes (Invitrogen) (pH 7.4) was mixed with fluorescent probe (Fluo4 NW, Invitrogen), the mixture was added to each wells, then balanced with cells at 37° C. for 60 minutes, and then balanced with cells at 22° C. for 15 minutes;

3. The test plate was placed in a microplate reader (CellLux, PerkinElmer), a DMSO solution or HBSS buffer with an appropriate concentration of the test compound and the positive control was added, and 0.3 nM endothelin-1 or HBSS buffer (base control) was added after 5 minutes, and then the change in fluorescence intensity proportional to the concentration of $Ca^{2+}$ ions of free cell lysosomes was measured;

4. Results were shown as the percent inhibition of control response to 0.3 nM endothelin-1;

5. Standard positive control was BQ-788, several concentrations were tested in each experiments. The data was analyzed using Prism to generate a concentration-response curve, and $IC_{50}$ values of the compounds were calculated.

TABLE 11

In vitro antagonistic activity of the compounds of the present disclosure against human $ET_A$ and $ET_B$ receptors and their selectivity to $ET_B$

| Compound | $ET_A$ $IC_{50}$(nM) | $ET_B$ $IC_{50}$(μM) | $ET_A/ET_B$ selectivity |
|---|---|---|---|
| WX001 | 2.8 | 85 | 30300 |
| WX002 | 2.8 | >300 | >107000 |
| WX003 | 2.6 | 71 | 27300 |
| WX004 | 1.5 | 21 | 14000 |
| WX005 | 1.4 | 110 | 78500 |
| WX006 | 1.3 | >300 | >230700 |
| WX007 | 2.1 | 35 | 16600 |
| WX008 | 0.43 | 280 | 651100 |
| WX009 | 2.3 | 71 | 30800 |
| WX010 | 1.5 | 61 | 40600 |
| WX011 | 1.0 | 22 | 22000 |
| WX012 | 0.17 | 16 | 94100 |
| WX013 | 1.4 | 66 | 47100 |
| WX014 | 1.3 | 35 | 26900 |
| WX015 | 0.86 | >300 | >348800 |
| WX016 | 0.79 | 22 | 27800 |
| WX017 | 0.45 | 16 | 35500 |
| WX018 | 0.76 | 9.6 | 12600 |
| WX019 | 0.44 | >30 | >68100 |
| WX020 | 0.35 | 17 | 48500 |
| WX021 | 0.34 | 46 | 135200 |
| WX022 | 2.1 | 76 | 36100 |
| WX023 | 0.32 | 15 | 46800 |
| WX024 | 0.25 | 6.7 | 26800 |
| WX025 | 3.1 | 61 | 19600 |
| WX026 | 1.1 | 73 | 66300 |
| WX027 | 2.8 | 68 | 24200 |
| WX028 | 2.0 | >100 | >50000 |
| WX029 | 0.65 | 16 | 24600 |
| WX030 | 1.3 | 33 | 25300 |
| WX031 | 1.1 | >100 | >90900 |
| WX032 | 3.0 | >30 | >10000 |
| WX033 | 1.6 | >30 | >18700 |
| WX034 | 3.6 | 200 | 55500 |

Conclusion:

The compounds of the present disclosure all exhibit very high antagonist activity against human $ET_A$ receptors in vitro. The selectivity of the compounds of the present disclosure for $ET_A$ and $ET_B$ is more than 10000-fold.

Experimental Embodiment 3: Human Pregnane X Receptor (PXR) Assay

Experimental Purpose:
The effect of the compounds on the induction of PXR-mediated CYP3A expression was evaluated.
Experimental materials and devices:

| Name | Source | Model |
|---|---|---|
| DPX2 Cell | Puracyp | / |
| Dosing Media | Puracyp | D-500-100 |
| P450-Glo ™ CYP3A4 Assay and Screening System (Luciferin-IPA& Luciferin Detection Reagent) | Promega | V9001 |
| CellTiter-Fluor ™ Kit (CTF buffer & Assay Buffer) | Promega | G6081 |
| One Glo ™ kit (ONE-Glo ™ Luciferase Assay Buffer&ONE-Glo ™ Assay Substrate) | Promega | E6110 |

Experimental Protocol:
1. DPX2 cells were thawn under sterile conditions.
2. DPX2 cell solution was distributed in 96-well plate (100 μL/well), and the plate was placed in a 5% $CO_2$/37° C. incubator overnight.

3. Quantitative feeding medium was thawn in a 37° C. water bath. Positive control rifampin was thawn at room temperature. A series of test compounds and positive control dilutions were prepared in quantitative feeding medium. The cells were carefully aspirated from each wells without disturbing the cells during aspiration and the medium was discarded. 100 μL of each test compound concentration was transferred to pre-labeled wells. The operation of the positive control group and the blank group were the same. The plate was placed back into the incubator for 24 hours exposure.

4. Enzyme activity test:

(1) 7 μL of Luciferin-IPA was added to 7 μL of quantitative feeding medium, the mixture was mixed by inverting, and poured into a Luciferin-IPA reagent tank.

(2) The 96-well plate was taken out from the incubator, and the media was carefully aspirated from each wells. 50 μL of the Luciferin-IPA reagent was added to each wells, and the cell plate was placed back into the incubator for 60 minutes.

(3) During incubation, the P450-Glo buffer was poured into the Luciferin detection reagent, and the mixture was mixed by inverting.

(4) The 96-well plate was taken out from the incubator, and 40 μL of solution from each well was transferred into the corresponding white 96-well plate, and the corresponding position of each wells was consistent with the original cell plate.

(5) After transferring the P450-Glo™ solution to the replica plate, 10 mL of cell titration buffer (CTF buffer) was transferred to a 15 mL sterile conical tube, followed by addition of 5 μL CellTiter-Fluor™ reagent, and the mixture was mixed by inverting.

(6) A multi-channel liquid pipetter was used, 100 μL of CellTiter-Fluor™ reagent was gently added to the 96-well plate where the cells were originally cultured, and then the cell plate was placed back to the incubator for 60 minutes.

(7) Each wells of the replica plate was added with 40 μL of Luciferin detection reagent/P450-Glo buffer, stirred, and incubated for 20 minutes at room temperature.

(8) After incubation with Luciferin detection reagent for 20 minutes, a photometer (set 1-5 seconds. Readout Time) was used to measure the luminescence of each wells of the white 96-well plate. A relatively high gain setting should be used.

(9) ONE-Glo™ luciferase detection buffer was added to the ONE-Glo™ detection reagent, and the mixture was mixed by inverting.

(10) After incubating for 60 minutes at 37° C., the original 96-well plate was taken out of the incubator. The reader was set to the fluorescence mode, the excitation wavelength was set to 380-400 nm, the emission wavelength was set to 505 nm, and the fluorescence intensity of each wells was measured.

(11) The cell plate was taken out of the enzyme reader, and 100 μL of ONE-Glo™ detection reagent was added to each wells. The mixture was mixed by shaking plates and incubated at room temperature for 5 minutes

(12) The enzyme reader was set to 5 seconds for preshaking and 5 seconds for wells reading, and the fluorescence intensity in each hole was measured. High instrument gain (sensitivity) settings should be used.

5. The activation effect of the drug on PXR was reflected by the fold induction, that is, the fold induction of each group=luciferase activity value of the drug treatment group/luciferase activity value of the solvent control group, and the fold induction was used to predict the induction effect on CYP3A4.

The positive control was rifampicin, six concentrations were tested in each experiment. The data was analyzed using Prism to generate a concentration-response curve and the $EC_{50}$ value of the compound was calculated.

Experimental Results:

The test results are shown in table 12.

TABLE 12

Results of the induction effect of compound of the present disclosure on PXR-mediated CYP3A expression

| Test compound | WX013 | Control compound (macitentan) |
|---|---|---|
| $EC_{50}$ (μM) | 27.6 ± 1.33* | 6.34 ± 0.170* |

*Calculation error of simulation curve

Conclusion:

The compound WX013 of the present disclosure has a relatively weak induction effect on PXR-mediated CYP3A expression, and the compound macitentan has a relatively strong induction effect on PXR-mediated CYP3A expression. Therefore, in the characterization experiment of PXR-mediated induction of CYP3A expression, WX013 is superior to macitentan.

Experimental Embodiment 4: Human Liver Microsomal Cytochrome P450 Isozyme Inhibition Assay Experimental Purpose:

The purpose of the assay was to evaluate the inhibitory activity of the samples against human liver microsomal cytochrome P450 isozyme (CYP1A2, CYP2C9, CYP2C19, CYP2D6 and CYP3A4) using the 5-in-1 probe substrate of the CYP isozyme.

Experimental Protocol:

Mixed human liver microsomes (HLM) were purchased from Corning Inc. (Steuben, N.Y., USA) and stored below −80° C. before use. The test compound working solution which has been diluted into serial concentrations was added to an incubation system containing human liver microsomes, probe substrates and circulating system cofactors, and a control containing solvent without the test compound was used as the enzyme activity control (100%). The concentration of the metabolite produced by the probe substrate in the sample was determined using a liquid chromatography-tandem mass spectrometry (LC-MS/MS) method. Nonlinear regression analysis was performed on the average percent activity versus concentration of subjects using SigmaPlot (V.11). The $IC_{50}$ value was calculated by a three-parameter or four-parameter inverse-logarithmic equation.

Experimental Results:
The test results were shown in table 13.

TABLE 13

Inhibition results of compounds of the present disclosure on human liver microsomal cytochrome P450 isozyme

| Compound | P450 isozyme inhibition IC$_{50}$ (μM) | | | | |
| --- | --- | --- | --- | --- | --- |
| | CYP1A2 | CYP2C9 | CYP2C19 | CYP2D6 | CYP3A4-M |
| Control compound (macitentan) | 37 | 7.5 | 31 | >50 | 23 |
| WX005 | >50 | >50 | >50 | >50 | >50 |
| WX013 | 47 | >50 | >50 | >50 | 18 |
| WX025 | >50 | 35 | >50 | >50 | >50 |

Conclusion:

The compounds WX005, WX013 and WX025 of the present disclosure have very weak inhibitory effects on five main isozymes of CYP. Macitentan has weak inhibitory effects on four main isozymes of CYP, and the inhibitory effects on the isozymes CYP2C9 are moderate. Therefore, WX005, WX013, and WX025 were superior to macitentan in the characterization experiment on the inhibition of five major isozymes of human liver microsomal cytokine P450.

Experimental Embodiment 5: Inhibition Test of Compound on Bile Salt Transfer Pump (BSEP)

Experimental Purpose:

This experiment evaluates whether the test compound has an inhibitory effect during the transport process of the bile salt transfer pump (BSEP) by using LC/MS/MS to detect the absorption capacity of bile salt transfer pump (BSEP) to the substrate taurine TCA.

Experimental Materials:

| Name | Source |
| --- | --- |
| BSEP-Hi5-VT | Solvo Biotechnology Cat#: SB-BSEP-Hi5-VT |
| 1.0M TRIS Buffer pH 7.4 | Invitrogen Cat#: 15567-027 |
| Sucrose | Sigma Cat#: 84100 |
| Tris Base | Sigma Cat#: T1503 |
| Taurocholic Acid | Sigma Cat#: T4009 |
| ATP (disodium salt) | Sigma Cat#: A-2383 |
| 1M HEPES | Gibco Cat#: 15630-080 |
| AMP (disodium salt) | Sigma Cat#: 01930 |
| 0.5M EDTA | Biosolution Cat#: BIO260-15 |
| Methanol | Sigma Cat#: 494437 |
| Multiscreen 384-well FC filter plates - 1.2 micron glass fiber | Millipore Cat#: MZFCN0W10 |
| ECHO LDV plate | LabCYTE Cat#: LP-0200 |
| 384-well polypropylene plate | Costar Cat#: 3656 |
| ECHO 550 | LabCYTE |
| Internal standard | HDBiosciences |

Solution Preparation:

1. Buffer A:

50 mM HEPES pH 7.4, 100 mM KNO$_3$, 10 mM Mg (NO$_3$)$_2$, 50 mM sucrose.

2. Buffer B:

10 mM TRIS pH 7.4, 100 mM KNO$_3$, 10 mM Mg (NO$_3$)$_2$, 50 mM sucrose.

3. ATP buffer:

Prepared with buffer A, 8.16 mM ATP and 4.08 μM taurocholic acid were contained in 12 mL buffer A.

4. AMP buffer:

Prepared with buffer A, 8.16 mM AMP, 4.08 μM taurocholic acid 12 mL buffer A were contained in buffer A.

5. BSEP-Hi5-VT Vesicle solution:

A solution containing BSEP-Hi5-VT 5 μg/μL was prepared with buffer A.

Sample Preparation:

1. The compound was diluted to 100 mM with DMSO; then serially diluted 3-fold for an 11-point dilution; the minimum concentration was 0.169 μM.

2. Positive reference Glyburide was diluted to 20 mM with DMSO; then serially diluted 2-fold for an 11-point dilution; the minimum concentration was 19.5

Experimental Protocol:

1. 0.3 μL of a solution of the compound in DMSO or a diluted DMSO solution were transferred into corresponding wells of the compound plate using ECHO, respectively.

2. 14.7 μL of ATP buffer was added to the compound and the corresponding wells of zero percent effect (ZPE), respectively.

3. 14.7 μL of AMP buffer was added to the corresponding wells of 100% effect (HPE), respectively.

4. The plate was shaked for 10 minutes at 25° C.

5. 15 μL of BSEP-H15-VT Vesicle solution was added to all wells, respectively, and the plate was shaked for another 40 minutes at 25° C.

6. 5 μL 0.5 M ethylenediaminetetraacetic acid (EDTA) solution was added to all wells immediately, followed by addition of 65 μL of buffer B, and the whole reaction was completed.

7. 95 μL of liquid was transferred to the filter plate from the compound plate at the end of the reaction using an instrument.

8. After placing the liquid receiving plate under the filter plate, the liquid was removed using a centrifuge and the receiving plate liquid was discarded.

9. 90 μL of buffer B was added to the filter plate. After placing the liquid receiving plate under the filter plate, the liquid was removed using a centrifuge, and the receiving plate liquid was discarded, and filter plate was washed for three times in total.

10. The filter plate was dried overnight.

11. On the next day, 80 μL of methanol/water (80/20, volume ratio) solution was added to the filter plate.

12. The plate was shaked for 15 minutes after the filter plate was attached to the membrane.

13. A new liquid receiving plate was placed under the filter plate, and the filter plate was centrifuged for 5 minutes, and all liquids in the filter plate were filtrated into the receiving plate.

14. 15 μL of internal standard solution was added to each wells in the liquid receiving plate, and the plate was sealed with a membrane.

15. The content of taurocholic acid in the receiving plate was detected using LC/MS/MS.

Several concentrations were tested in each experiments. The data were analyzed using Prism to generate a concentration-response curve, and $IC_{50}$ values of the compounds were calculated.

Experimental Results:

The experimental results were shown in table 14.

TABLE 14

Inhibitory effect of the compound of the present disclosure on the bile salt transport pump (BSEP)

| Compound | Glibenclamide | Macitentan | WX013 |
|---|---|---|---|
| $IC_{50}$ (μM) | 1.489 | 0.2809 | 43.77 |

Conclusion:

The inhibitory effect of the compound WX013 of the present disclosure on the bile salt transport pump (BSEP) was extremely weak, but the inhibitory effect of macitentan was strong. Therefore, the inhibitory effect of WX013 on the bile salt transport pump was much weaker than that of macitentan, thereby significantly reducing the risk of developing hepatotoxicity.

Experimental Embodiment 6: Evaluation on the Pharmacokinetic of the Compounds in Rats Experimental Purpose:

SD male rats were selected as the test animals in this study, and the drug concentration in plasma of the rats at different time points via intravenous injection or oral gastric administration of the test compound was quantitatively measured using LC/MS/MS method to evaluate the pharmacokinetic characteristics of the test compounds in rats.

Experimental Materials:

Sprague Dawley (SD) rats (male, 200-300 g, 7-10 weeks old, Beijing Viton Lihua or Shanghai Slake).

Experimental Protocol:

A clear solution of the test compound was injected into SD rats via the tail vein (overnight fasting), or administrated orally by gavage (overnight fasting). For intravenous administration, 200 μL of jugular blood was collected via vein puncture at 0 hour (pre-dosing) and at 0.0833, 0.25, 0.5, 1, 2, 4, 6, 8 and 24 hours after dosing, which was then placed in an anticoagulation tube supplemented with EDTA-K2 (Suzuki Healthcare Medical Co., Ltd.). The mixture in the anticoagulation tube was vortexed to mix thoroughly at 4° C., and then centrifuged at 13000 rpm for 10 minutes to collect the plasma. For oral gavage administration, 200 μL of jugular blood was collected via vein puncture at 0 hour (pre-dosing) and at 0.5, 1, 2, 4, 6, 8 and 24 hours after dosing, which was then placed in an anticoagulation tube supplemented with EDTA-K2 (Suzuki Healthcare Medical Co., Ltd.). The mixture in the anticoagulation tube was vortexed to mix thoroughly, and then centrifuged at 13000 rpm for 10 minutes to collect the plasma. Plasma drug concentration was measured by LC/MS/MS method, and related pharmacokinetic parameters were calculated using WinNonlin™ Version 6.3 (Pharsight, Paul View, Calif.) pharmacokinetics software in non-room model linear logarithmic trapezoids method.

Experimental Results:

The experimental results were shown in table 15.

TABLE 15

Pharmacokinetic parameters of compounds of the disclosure in rats

| | 2. Intravenous injection (2 mg/kg) | | | 3. Oral administration (10 mg/kg) | | | |
|---|---|---|---|---|---|---|---|
| 1. Pharmacokinetic parameters in rats | 4. Plasma clearance rate (mL/min/kg) | 5. Half-life (h) | 6. The area under the plasma concentration time curve (μM · h) | 7. Peak concentration (μM) | 8. Peak time (h) | 9. The area under the plasma concentration time curve (μM · h) | 10. Bioavailability (%) |
| 11. WX001 | 12. 3.19 | 13. 1.26 | 14. 20.51 | 15. 37.45 | 16. 0.38 | 17. 117.67 | 18. 114.8 |
| 19. WX013 | 20. 3.71 | 21. 1.14 | 22. 16.09 | 23. 31.99 | 24. 0.25 | 25. 60.22 | 26. 74.9 |

Conclusion:

The compounds WX001 and WX013 of the present disclosure have a low plasma clearance rate (<5 mL/min/kg) and a high oral bioavailability (>70%) in rats.

Experimental embodiment 7: Evaluation on the pharmacokinetic of compounds in beagle dogs Experimental Purpose:

Male beagle dogs were selected as the tested animals in this study, and the drug concentration in plasma of beagle dogs at different time points via intravenous injection or oral perfusion gastric administration of the test compounds was quantitatively measured using LC/MS/MS method to evaluate the pharmacokinetic characteristics of the test compounds in beagle dogs.

Experimental Materials:

Beagle dog (male, 6-15 kg, more than 6 months old, Beijing Marshall Biotechnology Co., Ltd.).

Experimental Protocol:

A clear solution of the test compound was injected intravenously into beagle dogs (overnight fasting), or administrated orally to beagle dogs by gavage (overnight fasting). For intravenous administration, 500 μL of blood was collected from peripheral vessels at 0 hour (pre-dosing) and at 0.0833, 0.25, 0.5, 1, 2, 4, 6, 8 and 24 hours after dosing, which was then placed in an anticoagulation tube supplemented with EDTA-K2 (Suzuki Healthcare Medical Co., Ltd.). For oral gastric administration, 500 μL of blood was collected from peripheral vessels at 0 hour (pre-dosing) and at 0.25, 0.5, 1, 2, 4, 6, 8 and 24 hours after dosing, which was then placed in an anticoagulation tube supplemented with EDTA-K2. The mixture in the anticoagulation tube was vortexed to mix thoroughly, and then centrifuged at 13000 rpm for 10 minutes to collect the plasma. Plasma drug concentration was measured by LC/MS/MS method, and related pharmacokinetic parameters were calculated using WinNonlin™ Version 6.3 (Pharsight, Paul View, Calif.) pharmacokinetics software in non-room model linear logarithmic trapezoids method.

Experimental Results:

The experimental results were shown in table 16.

TABLE 16

Pharmacokinetic parameters of the compounds of the present disclosure in beagle dogs

| Pharmacokinetic parameters in beagle dogs | Intravenous injection (1 mg/kg) | | | Oral administration (3 mg/kg) | | | |
|---|---|---|---|---|---|---|---|
| | Plasma clearance rate (mL/min/kg) | half-life (h) | The area under the plasma concentration time curve (μM · h) | Peak concentration (μM) | Peak time (h) | The area under the plasma concentration time curve (μM · h) | Bioavailability F (%) |
| WX001 | 0.81 | 2.31 | 46.94 | 16.20 | 0.38 | 73.77 | 52.4 |
| WX013 | 4.79 | 0.86 | 7.56 | 12.75 | 0.38 | 33.40 | 147 |

Conclusion:

The compounds WX001 and WX013 of the present disclosure have a low plasma clearance rate (<5 mL/min/kg) and a high oral bioavailability (>50%) in beagle dogs.

What is claimed is:

1. A compound of formula (I), an (R)-isomer thereof, an (S)-isomer thereof, or a pharmaceutically acceptable salt thereof,

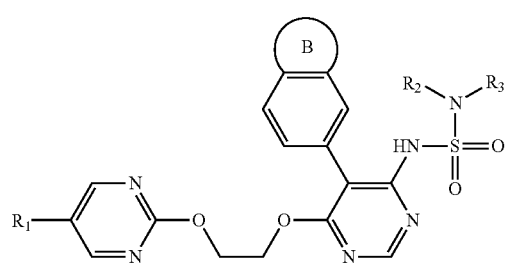

(I)

wherein, $R_1$ is selected from H, F, Cl, Br, I, OH and $NH_2$;

$R_2$ is selected from H and $C_{1-3}$ alkyl, wherein the $C_{1-3}$ alkyl is optionally substituted by one, two or three R;

$R_3$ is selected from H, $C_{1-6}$ alkyl, $C_{1-6}$ heteroalkyl, —$C_{1-3}$ alkyl-$C_{3-6}$ cycloalkyl, $C_{3-6}$ cycloalkyl and —$C_{1-3}$ alkyl-3-7 member heterocycloalkyl, wherein the $C_{1-6}$ alkyl, $C_{1-6}$ heteroalkyl, —$C_{1-3}$ alkyl-$C_{3-6}$ cycloalkyl, $C_{3-6}$ cycloalkyl or —$C_{1-3}$ alkyl-3-7-membered heterocycloalkyl is optionally substituted by one, two or three R;

or, $R_2$ and $R_3$ are connected to form a 3-8 membered ring optionally substituted by one, two or three R;

ring B is selected from 3-7 membered heterocycloalkyl and 5-6 membered heteroaryl, wherein the 3-7 membered heterocycloalkyl or 5-6 membered heteroaryl is optionally substituted by one, two or three R;

R is independently selected from H, F, Cl, Br, I, OH, $NH_2$, CN, $C_{1-6}$ alkyl and $C_{1-6}$ heteroalkyl, wherein the $C_{1-6}$ alkyl or $C_{1-6}$ heteroalkyl is optionally substituted by one, two or three R';

R' is independently selected from F, Cl, Br, I, OH, $NH_2$, CN, Me, $CH_2F$, $CHF_2$, $CF_3$ and Et;

each of the $C_{1-6}$ heteroalkyl, 3-7 membered heterocycloalkyl and 5-6 membered heteroaryl contains one, two, three or four heteroatoms or heteroatom groups independently selected from N, —O—, —S—, —NH—, —S(=O)$_2$— and —S(=O)—.

2. The compound, the (R)-isomer thereof, the (S)-isomer thereof, or the pharmaceutically acceptable salt thereof as defined in claim 1, wherein, R is selected from H, F, Cl, Br, I, OH, $NH_2$, CN, $C_{1-3}$ alkyl, $C_{1-3}$ alkyl-S(=O)$_2$— and $C_{1-3}$ alkyl-O—, wherein the $C_{1-3}$ alkyl, $C_{1-3}$ alkyl-S(=O)$_2$— or $C_{1-3}$ alkyl-O— is optionally substituted by one, two or three R'.

3. The compound, the (R)-isomer thereof, the (S)-isomer thereof, or the pharmaceutically acceptable salt thereof as defined in claim 2, wherein, R is selected from H, F, Cl, Br, I, OH, $NH_2$, CN, Me, Et,

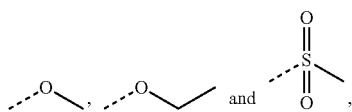

wherein the Me, Et,

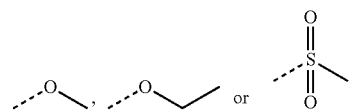

is optionally substituted by one, two or three R'.

4. The compound, the (R)-isomer thereof, the (S)-isomer thereof, or the pharmaceutically acceptable salt thereof as defined in claim 3, wherein, R is selected from H, F, Cl, Br, I, OH, $NH_2$, CN, Me, $CH_2F$, $CHF_2$, $CF_3$, Et,

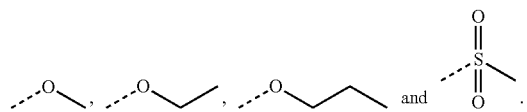

5. The compound, the (R)-isomer thereof, the (S)-isomer thereof, or the pharmaceutically acceptable salt thereof as defined in claim 1, wherein, $R_2$ is selected from H and Me.

6. The compound, the (R)-isomer thereof, the (S)-isomer thereof, or the pharmaceutically acceptable salt thereof as defined in claim 1, wherein, $R_3$ is selected from H, $C_{1-4}$ alkyl, $C_{1-4}$ alkyl-O—$C_{1-4}$ alkyl, cyclobutyl, —$C_{1-3}$ alkyl-cyclobutyl, —$C_{1-3}$ alkyl-cyclopropyl, —$C_{1-3}$ alkyl-tetrahydrofuranyl and —$C_{1-3}$ alkyl-tetrahydropyranyl, wherein the $C_{1-4}$ alkyl, $C_{1-4}$ alkyl-O—$C_{1-4}$ alkyl, cyclobutyl, —$C_{1-3}$ alkyl-cyclobutyl, —$C_{1-3}$ alkyl-cyclopropyl, —$C_{1-3}$ alkyl-tetrahydrofuranyl or —$C_{1-3}$ alkyl-tetrahydropyranyl is optionally substituted by one, two or three R.

7. The compound, the (R)-isomer thereof, the (S)-isomer thereof, or the pharmaceutically acceptable salt thereof as defined in claim 6, wherein, $R_3$ is selected from H, Me, Et,

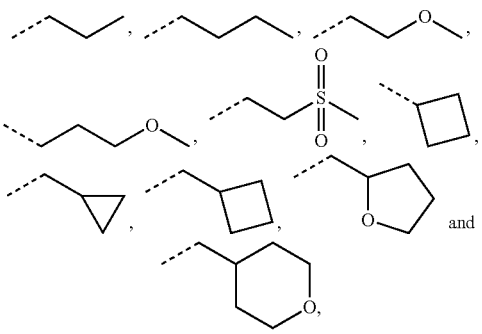

wherein the Me, Et,

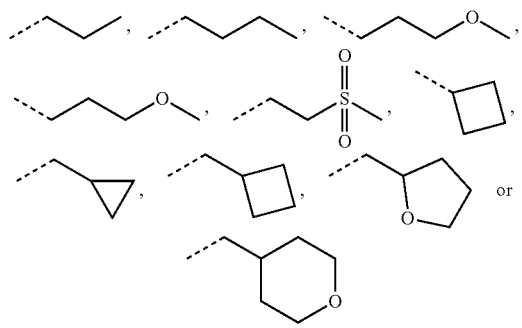

is optionally substituted by one, two or three R.

8. The compound, the (R)-isomer thereof, the (S)-isomer thereof, or the pharmaceutically acceptable salt thereof as defined in claim 7, wherein, $R^3$ is selected from H, Me, Et,

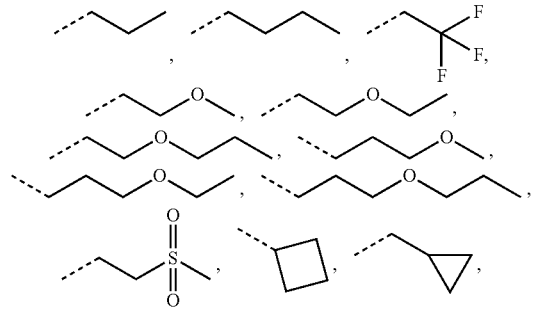

-continued

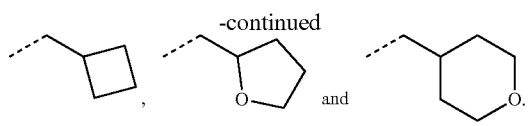

9. The compound, the (R)-isomer thereof, the (S)-isomer thereof, or the pharmaceutically acceptable salt thereof as defined in claim 1, wherein, $R_2$ and $R_3$ are connected to form a 6-8 membered heterocycloalkyl optionally substituted by one, two or three R.

10. The compound, the (R)-isomer thereof, the (S)-isomer thereof, or the pharmaceutically acceptable salt thereof as defined in claim 9, wherein, the structural unit

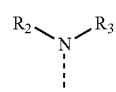

is selected from

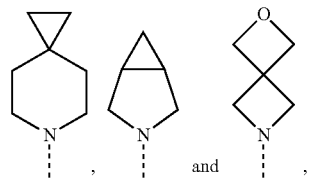

wherein the

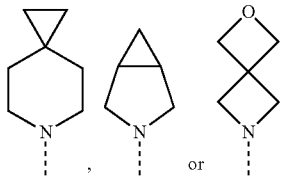

is optionally substituted by one, two or three R.

11. The compound, the (R)-isomer thereof, the (S)-isomer thereof, or the pharmaceutically acceptable salt thereof as defined in claim 10, wherein, the structural unit

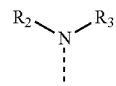

is selected from

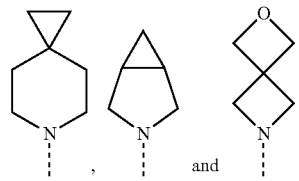

12. The compound, the (R)-isomer thereof, the (S)-isomer thereof, or the pharmaceutically acceptable salt thereof as defined in claim 1, wherein, ring B is selected from tetrahydrofuranyl, tetrahydrothienyl, 1,3-dioxolanyl, pyrrolidinyl, thiazolyl, pyrazolyl and imidazolyl, wherein the tetrahydrofuranyl, tetrahydrothienyl, 1,3-dioxolanyl, pyrrolidinyl, thiazolyl, pyrazolyl or imidazolyl is optionally substituted by one, two or three R.

13. The compound, the (R)-isomer thereof, the (S)-isomer thereof, or the pharmaceutically acceptable salt thereof as defined in claim 12, wherein, the structural unit

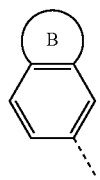

is selected from

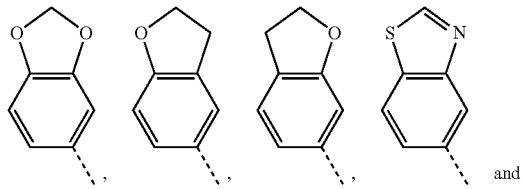

and

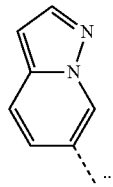

14. The compound, the (R)-isomer thereof, the (S)-isomer thereof, or the pharmaceutically acceptable salt thereof as defined in claim 1, which is selected from (I-1)

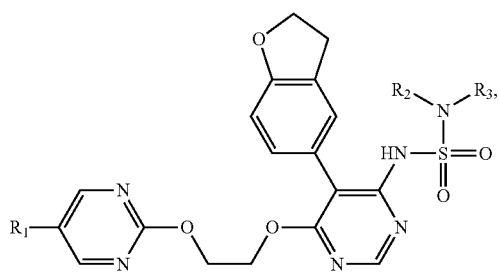

(I-2)

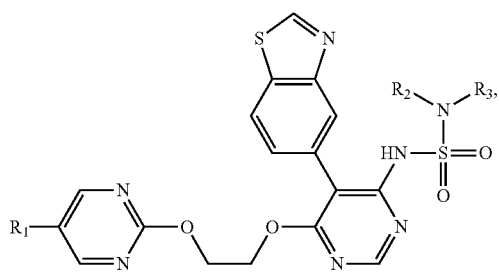

(I-3)

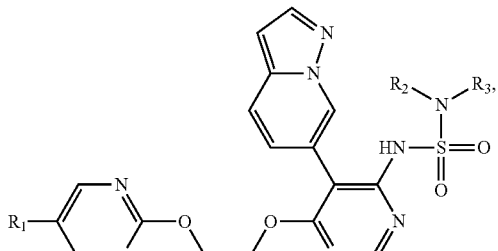

(I-4)

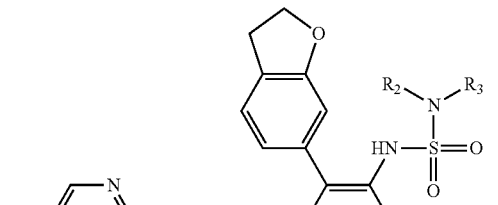

and (I-5)

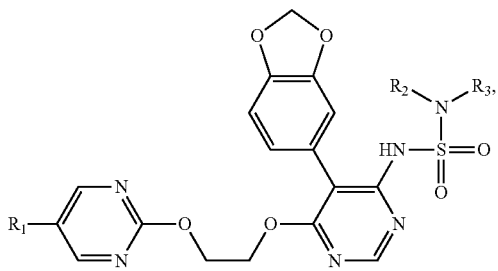

wherein,

R, R₁ or R₂ is as defined in claim 1.

15. A pharmaceutical composition, which comprises a therapeutically effective amount of the compound or the pharmaceutically acceptable salt as defined in claim 1 as an active ingredient, and a pharmaceutically acceptable carrier.

16. A method for treating pulmonary artery hypertension, primary hypertension, refractory hypertension, diabetic nephropathy and intracranial vasospasm in a subject in need thereof, comprising administering a therapeutically effective amount of the pharmaceutical composition as defined in claim 1 to the subject.

17. A method for treating pulmonary artery hypertension, primary hypertension, refractory hypertension, diabetic nephropathy and intracranial vasospasm in a subject in need thereof, comprising administering a therapeutically effective amount of the pharmaceutical composition as defined in claim 15 to the subject.

18. The compound, the (R)-isomer thereof, the (S)-isomer thereof, or the pharmaceutically acceptable salt thereof as defined in claim 1, wherein the compound is selected from

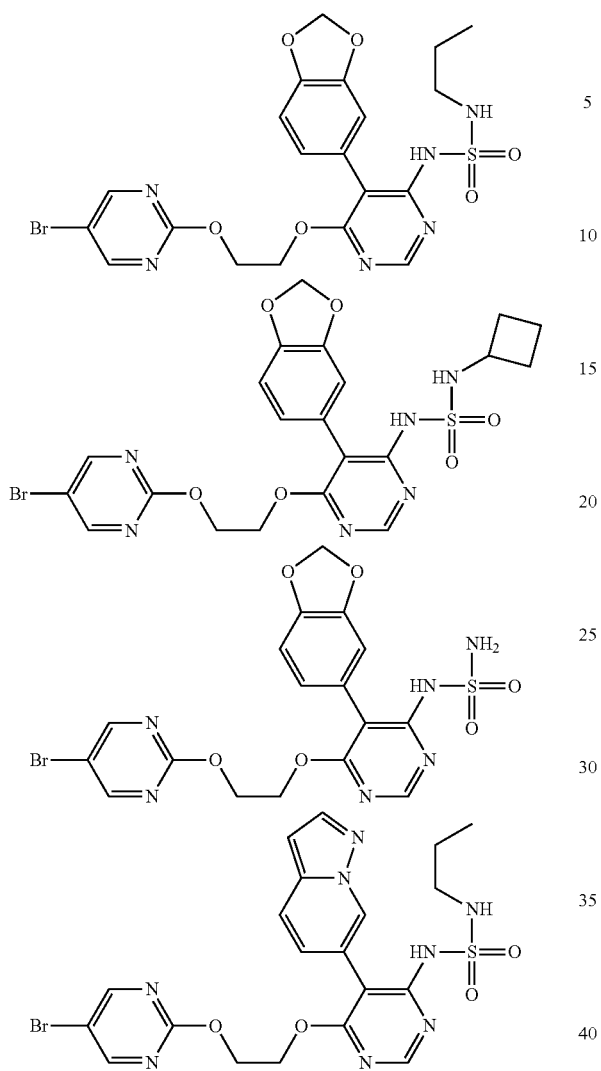
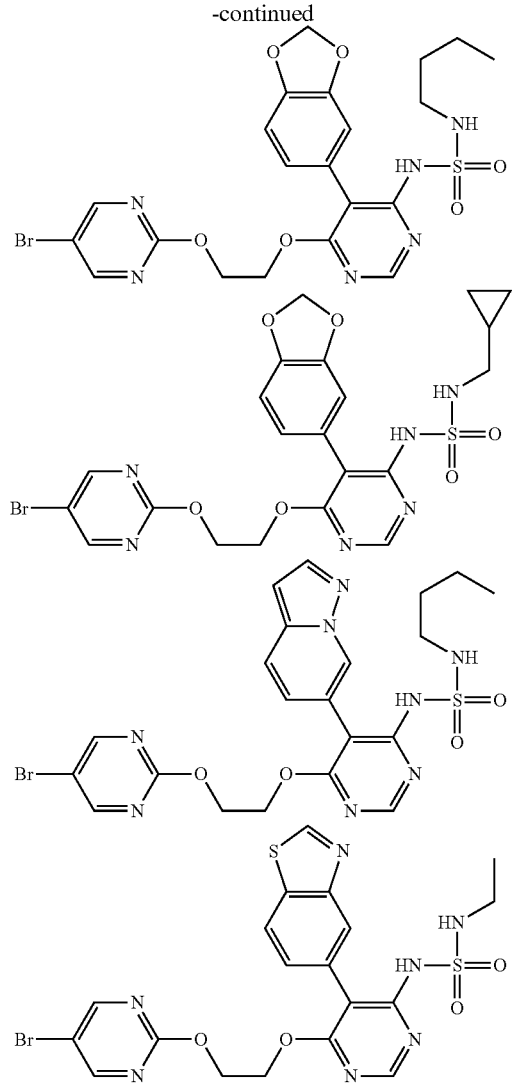
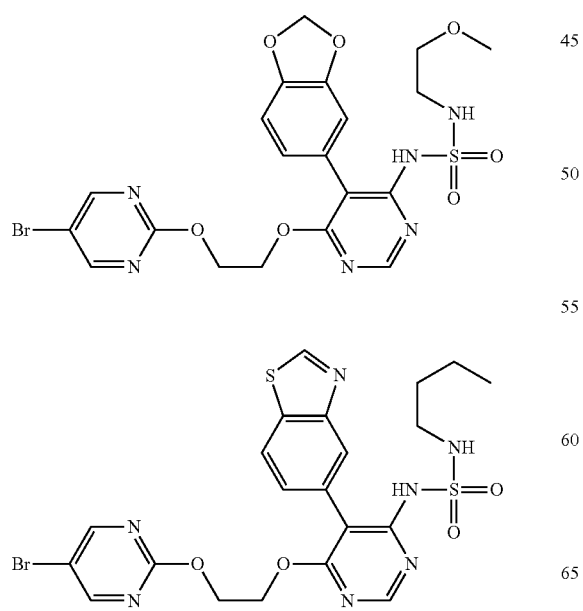
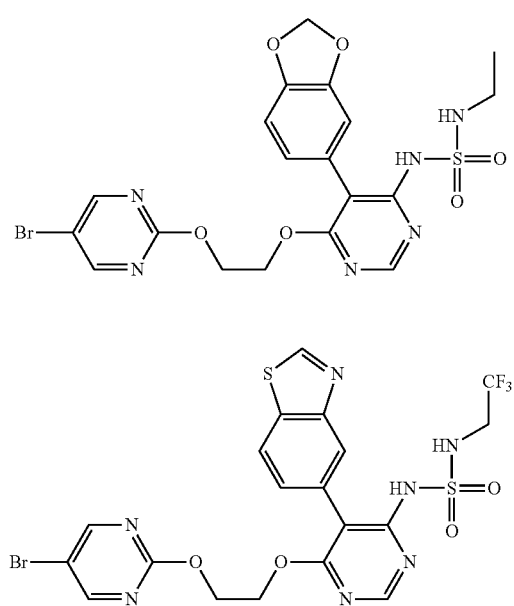

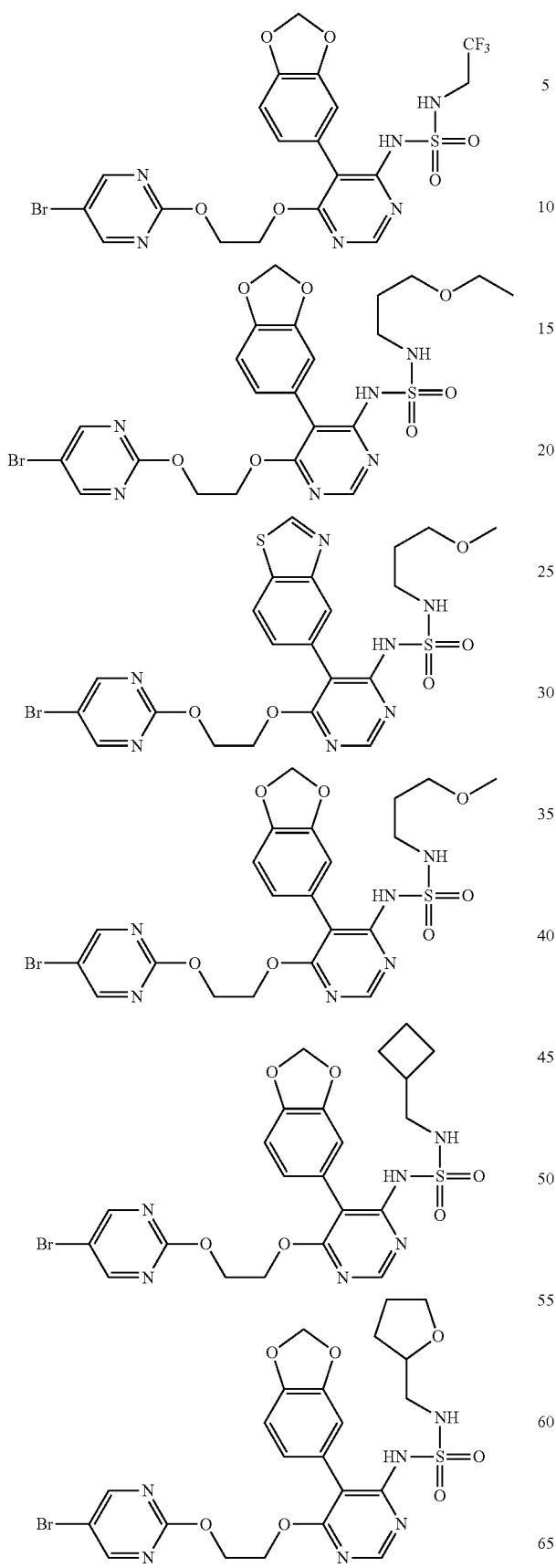
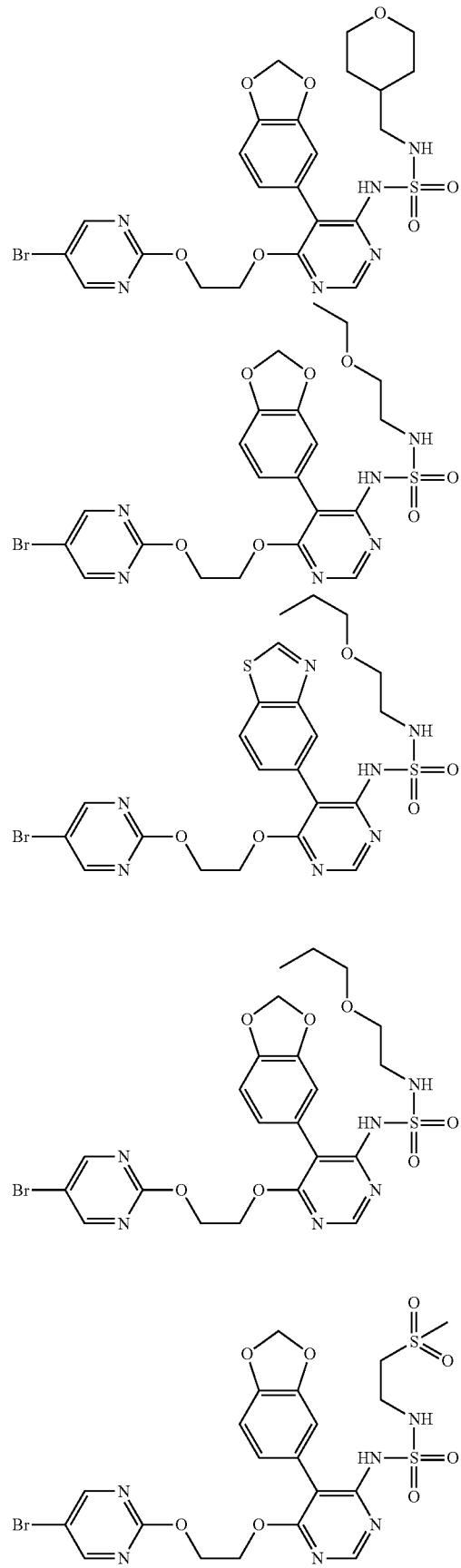

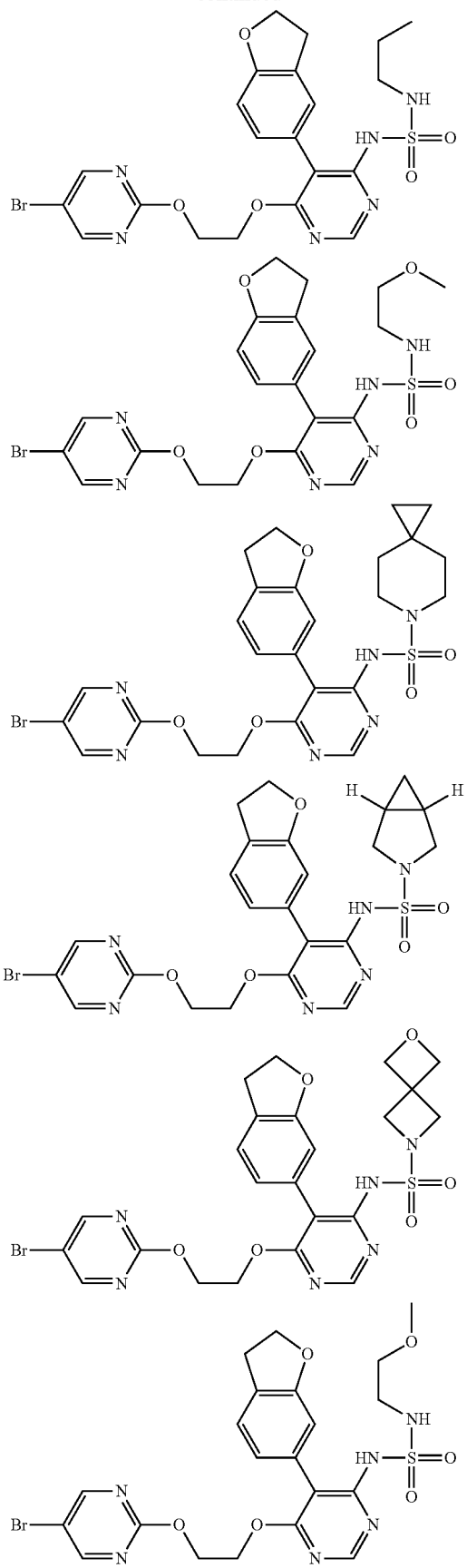
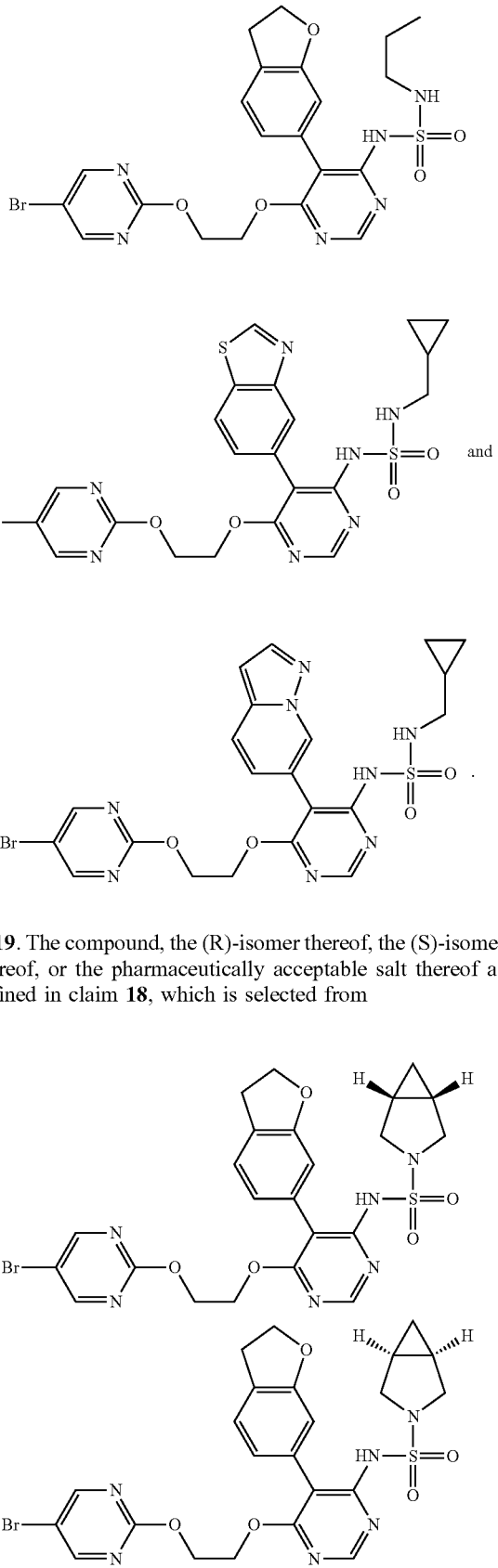
19. The compound, the (R)-isomer thereof, the (S)-isomer thereof, or the pharmaceutically acceptable salt thereof as defined in claim 18, which is selected from -continued
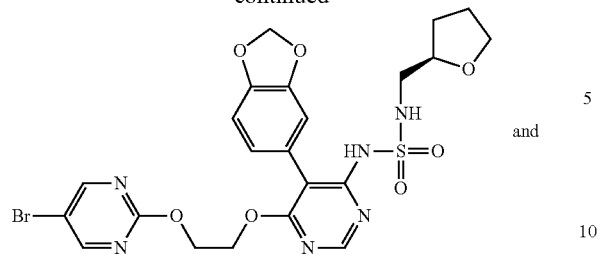
and
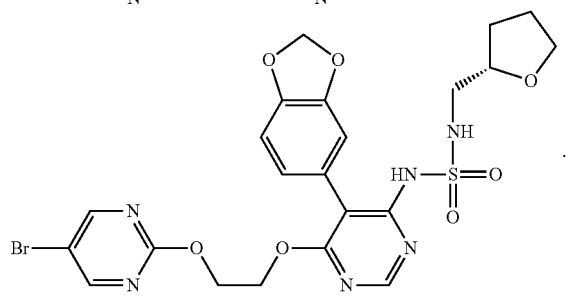
* * * * *